(12) United States Patent
Giasolli et al.

(10) Patent No.: US 10,779,969 B2
(45) Date of Patent: Sep. 22, 2020

(54) ENDOVASCULAR IMPLANT AND DEPLOYMENT DEVICES

(71) Applicant: Intact Vascular, Inc., Wayne, PA (US)

(72) Inventors: Robert Giasolli, Orange, CA (US); Peter Schneider, Honolulu, HI (US)

(73) Assignee: Intact Vascular, Inc., Wayne, PA (US)

( * ) Notice: Subject to any disclaimer, the term of this patent is extended or adjusted under 35 U.S.C. 154(b) by 0 days.

(21) Appl. No.: 16/426,627

(22) Filed: May 30, 2019

(65) Prior Publication Data

US 2019/0282381 A1    Sep. 19, 2019

Related U.S. Application Data

(63) Continuation of application No. 15/921,459, filed on Mar. 14, 2018, now Pat. No. 10,390,977, and a
(Continued)

(51) Int. Cl.
A61F 2/848    (2013.01)
A61F 2/844    (2013.01)
(Continued)

(52) U.S. Cl.
CPC .............. *A61F 2/848* (2013.01); *A61F 2/844* (2013.01); *A61F 2/86* (2013.01); *A61F 2/915* (2013.01);
(Continued)

(58) Field of Classification Search
CPC .. A61F 2/848; A61F 2/844; A61F 2/86; A61F 2/915; A61F 2/95; A61F 2/88;
(Continued)

(56) References Cited

U.S. PATENT DOCUMENTS 3,221,746 A    12/1965   Noble
3,635,223 A     1/1972   Klieman
(Continued)

FOREIGN PATENT DOCUMENTS

AU    2008335140    11/2012
AU    2011274392    11/2013
(Continued)

OTHER PUBLICATIONS

U.S. Appl. No. 15/921,459, filed Mar. 14, 2018, Endovascular Implant.
(Continued)

*Primary Examiner* — Katrina M Stransky
(74) *Attorney, Agent, or Firm* — Knobbe Martens Olson & Bear, LLP

(57) ABSTRACT

A plaque tack can be used for holding plaque against blood vessel walls such as in treating atherosclerotic occlusive disease. The plaque tack can be formed as a thin, annular band for holding loose plaque under a spring or other expansion force against a blood vessel wall. Focal elevating elements and/or other features, such as anchors, can be used to exert a holding force on a plaque position while minimizing the amount of material surface area in contact with the plaque or blood vessel wall and reducing the potential of friction with the endoluminal surface. This approach offers clinicians the ability to perform a minimally invasive post-angioplasty treatment and produce a stent-like result without using a stent.

21 Claims, 28 Drawing Sheets

Related U.S. Application Data continuation of application No. 15/640,095, filed on Jun. 30, 2017, application No. 15/921,459, which is a continuation of application No. 15/170,772, filed on Jun. 1, 2016, now Pat. No. 10,278,839, application No. 15/650,095, which is a continuation of application No. 15/170,772, filed on Jun. 1, 2016, now Pat. No. 10,278,839, which is a continuation of application No. 13/153,257, filed on Jun. 3, 2011, now Pat. No. 9,375,327.

(51) Int. Cl.
| | | |
|---|---|---|
| A61F 2/915 | (2013.01) | |
| A61F 2/86 | (2013.01) | |
| A61F 2/95 | (2013.01) | |
| A61F 2/966 | (2013.01) | |
| A61F 2/82 | (2013.01) | |
| A61F 2/958 | (2013.01) | |
| A61F 2/91 | (2013.01) | |
| A61F 2/89 | (2013.01) | |
| A61F 2/88 | (2006.01) | |
| A61F 2/92 | (2013.01) | |
| A61L 31/16 | (2006.01) | |

(52) U.S. Cl.
CPC ............... *A61F 2/95* (2013.01); *A61L 31/16* (2013.01); *A61F 2/88* (2013.01); *A61F 2/89* (2013.01); *A61F 2/91* (2013.01); *A61F 2/92* (2013.01); *A61F 2/958* (2013.01); *A61F 2002/823* (2013.01); *A61F 2002/825* (2013.01); *A61F 2002/826* (2013.01); *A61F 2002/8483* (2013.01); *A61F 2002/8486* (2013.01); *A61F 2002/91508* (2013.01); *A61F 2002/91575* (2013.01); *A61F 2002/91583* (2013.01); *A61F 2002/9665* (2013.01); *A61F 2220/0016* (2013.01); *A61F 2220/0066* (2013.01); *A61F 2230/0054* (2013.01); *A61F 2250/0067* (2013.01); *A61F 2250/0098* (2013.01)

(58) Field of Classification Search
CPC ...... A61F 2/89; A61F 2/91; A61F 2/92; A61F 2/958; A61F 2002/825; A61F 2002/823; A61F 2002/826; A61F 2002/8483; A61F 2002/8486; A61F 2002/91508; A61F 2002/91583; A61F 2002/91575; A61F 2002/9665
See application file for complete search history.

(56) References Cited

U.S. PATENT DOCUMENTS

| | | |
|---|---|---|
| 4,292,974 A | 10/1981 | Fogarty et al. |
| 4,446,867 A | 5/1984 | Leveen et al. |
| 4,465,072 A | 8/1984 | Taheri |
| 4,515,587 A | 5/1985 | Schiff |
| 4,545,367 A | 10/1985 | Tucci |
| 4,545,390 A | 10/1985 | Leary |
| 4,552,127 A | 11/1985 | Schiff |
| 4,576,591 A | 3/1986 | Kay et al. |
| 4,589,412 A | 5/1986 | Kensey |
| 4,641,654 A | 2/1987 | Samson et al. |
| 4,651,738 A | 3/1987 | Demer et al. |
| 4,687,465 A | 8/1987 | Prindle et al. |
| 4,723,550 A | 2/1988 | Bales et al. |
| 4,723,936 A | 2/1988 | Buchbinder et al. |
| 4,723,938 A | 2/1988 | Goodin et al. |
| 4,726,374 A | 2/1988 | Bales et al. |
| 4,758,223 A | 7/1988 | Rydell |
| 4,762,130 A | 8/1988 | Fogarty et al. |
| 4,781,192 A | 11/1988 | Demer |
| 4,784,636 A | 11/1988 | Rydell |
| 4,846,174 A | 7/1989 | Willard et al. |
| 4,848,342 A | 7/1989 | Kaltenbach |
| RE33,166 E | 2/1990 | Samson |
| 5,009,659 A | 4/1991 | Hamlin et al. |
| 5,024,668 A | 6/1991 | Peters et al. |
| 5,042,707 A | 8/1991 | Taheri |
| 5,047,015 A | 9/1991 | Foote et al. |
| 5,102,390 A | 4/1992 | Crittenden et al. |
| 5,196,024 A | 3/1993 | Barath |
| 5,201,757 A | 4/1993 | Heyn et al. |
| 5,242,452 A | 9/1993 | Inoue |
| 5,246,420 A | 9/1993 | Kraus et al. |
| 5,250,029 A | 10/1993 | Lin et al. |
| 5,250,060 A | 10/1993 | Carbo et al. |
| 5,263,962 A | 11/1993 | Johnson et al. |
| 5,269,758 A | 12/1993 | Taheri |
| 5,304,121 A | 4/1994 | Sahatjian |
| 5,318,529 A | 6/1994 | Kontos |
| 5,336,234 A | 8/1994 | Virgil et al. |
| 5,344,397 A | 9/1994 | Heaven et al. |
| 5,383,890 A | 1/1995 | Miraki et al. |
| 5,397,305 A | 3/1995 | Kawula et al. |
| 5,397,355 A | 3/1995 | Marin et al. |
| 5,421,955 A | 6/1995 | Lau et al. |
| 5,423,851 A | 6/1995 | Samuels |
| 5,423,885 A | 6/1995 | Williams |
| 5,501,689 A | 3/1996 | Green et al. |
| 5,534,007 A | 7/1996 | St. Germain et al. |
| 5,536,252 A | 7/1996 | Imran et al. |
| 5,540,659 A | 7/1996 | Teirstein |
| 5,545,135 A | 8/1996 | Iacob et al. |
| 5,562,728 A | 10/1996 | Lazarus et al. |
| 5,569,272 A | 10/1996 | Reed et al. |
| 5,571,135 A | 11/1996 | Fraser et al. |
| 5,591,197 A | 1/1997 | Orth et al. |
| 5,593,417 A | 1/1997 | Rhodes |
| 5,616,149 A | 4/1997 | Barath |
| 5,634,928 A | 6/1997 | Fischell et al. |
| 5,643,312 A | 7/1997 | Fischell et al. |
| 5,665,116 A | 9/1997 | Chaisson et al. |
| 5,681,346 A | 10/1997 | Orth et al. |
| 5,704,913 A | 1/1998 | Abele et al. |
| 5,725,572 A | 3/1998 | Lam et al. |
| 5,728,158 A | 3/1998 | Lau et al. |
| 5,743,874 A | 4/1998 | Fischell et al. |
| 5,746,716 A | 5/1998 | Vigil et al. |
| 5,746,764 A | 5/1998 | Green et al. |
| 5,776,161 A | 7/1998 | Globerman |
| 5,797,951 A | 8/1998 | Mueller |
| 5,800,526 A | 9/1998 | Anderson et al. |
| 5,813,977 A | 9/1998 | Hinchliffe et al. |
| 5,817,152 A | 10/1998 | Birdsall et al. |
| 5,829,662 A | 11/1998 | Allen et al. |
| 5,833,694 A | 11/1998 | Poncet |
| 5,843,033 A | 12/1998 | Ropiak |
| 5,911,725 A | 6/1999 | Boury |
| 5,925,061 A | 7/1999 | Ogi et al. |
| 5,928,247 A | 7/1999 | Barry et al. |
| 5,954,742 A | 9/1999 | Osypka |
| 5,957,949 A | 9/1999 | Leonhardt et al. |
| 5,968,068 A | 10/1999 | Dehdashtian et al. |
| 5,968,088 A | 10/1999 | Hansen et al. |
| 5,972,023 A | 10/1999 | Tanner et al. |
| 5,980,552 A | 11/1999 | Pinchasik et al. |
| 6,004,328 A | 12/1999 | Solar |
| 6,007,543 A | 12/1999 | Ellis et al. |
| 6,009,614 A | 1/2000 | Morales |
| 6,013,854 A | 1/2000 | Moriuchi |
| 6,022,374 A | 2/2000 | Imran |
| 6,036,725 A | 3/2000 | Avellanet |
| 6,048,360 A | 4/2000 | Khosravi et al. |
| 6,053,941 A | 4/2000 | Lindenberg et al. |
| 6,053,943 A | 4/2000 | Edwin et al. |
| 6,080,177 A | 6/2000 | Igaki |
| 6,090,135 A | 7/2000 | Plaia et al. |
| 6,110,198 A | 8/2000 | Fogarty et al. |

(56) References Cited

U.S. PATENT DOCUMENTS

| | | |
|---|---|---|
| 6,123,722 A | 9/2000 | Fogarty et al. |
| 6,126,685 A | 10/2000 | Lenker et al. |
| 6,129,754 A | 10/2000 | Kanesaka et al. |
| 6,139,573 A | 10/2000 | Sogard et al. |
| 6,143,016 A | 11/2000 | Bleam et al. |
| 6,146,358 A | 11/2000 | Rowe |
| 6,152,937 A | 11/2000 | Peterson et al. |
| 6,157,852 A | 12/2000 | Selmon et al. |
| 6,165,199 A | 12/2000 | Barbut |
| 6,187,034 B1 | 2/2001 | Frantzen |
| 6,197,013 B1 | 3/2001 | Reed |
| 6,197,103 B1 | 3/2001 | Davies et al. |
| 6,200,336 B1 | 3/2001 | Pavcnik et al. |
| 6,203,568 B1 | 3/2001 | Lombardi et al. |
| 6,203,569 B1 | 3/2001 | Wijay |
| 6,221,102 B1 | 4/2001 | Baker et al. |
| 6,241,667 B1 | 6/2001 | Vetter et al. |
| 6,254,628 B1 | 7/2001 | Wallace et al. |
| 6,258,117 B1 | 7/2001 | Camrud et al. |
| 6,266,550 B1 | 7/2001 | Selmon et al. |
| 6,270,524 B1 | 8/2001 | Kim |
| 6,273,909 B1 | 8/2001 | Kugler et al. |
| 6,290,728 B1 | 9/2001 | Phelps et al. |
| 6,312,444 B1 | 11/2001 | Barbut |
| 6,312,460 B2 | 11/2001 | Drasler et al. |
| 6,325,824 B2 | 12/2001 | Limon |
| 6,344,053 B1 | 2/2002 | Boneau |
| 6,364,901 B1 | 4/2002 | Inoue |
| 6,364,904 B1 | 4/2002 | Smith |
| 6,371,962 B1 | 4/2002 | Ellis et al. |
| 6,387,113 B1 | 5/2002 | Hawkins et al. |
| 6,402,777 B1 | 6/2002 | Globerman |
| 6,409,863 B1 | 6/2002 | Williams et al. |
| 6,425,915 B1 | 7/2002 | Khosravi et al. |
| 6,428,550 B1 | 8/2002 | Vargas et al. |
| 6,428,566 B1 | 8/2002 | Holt |
| 6,475,237 B2 | 11/2002 | Drasler et al. |
| 6,485,510 B1 | 11/2002 | Camrud et al. |
| 6,491,707 B2 | 12/2002 | Makower et al. |
| 6,508,822 B1 | 1/2003 | Peterson et al. |
| 6,517,573 B1 | 2/2003 | Pollock et al. |
| 6,520,984 B1 | 2/2003 | Garrison et al. |
| 6,527,800 B1 | 3/2003 | McGuckin, Jr. et al. |
| 6,547,817 B1 | 4/2003 | Fischell et al. |
| 6,551,353 B1 | 4/2003 | Baker et al. |
| 6,599,296 B1 | 7/2003 | Gillick et al. |
| 6,623,521 B2 | 9/2003 | Steinke et al. |
| 6,629,994 B2 | 10/2003 | Gomez et al. |
| 6,635,083 B1 | 10/2003 | Cheng et al. |
| 6,648,911 B1 | 11/2003 | Sirhan et al. |
| 6,660,031 B2 | 12/2003 | Tran et al. |
| 6,676,698 B2 | 1/2004 | McGuckin, Jr. et al. |
| 6,692,504 B2 | 2/2004 | Kurz et al. |
| 6,699,274 B2 | 3/2004 | Stinson |
| 6,699,277 B1 | 3/2004 | Freidberg et al. |
| 6,706,061 B1 | 3/2004 | Fischell et al. |
| 6,716,240 B2 | 4/2004 | Fischell et al. |
| 6,719,775 B2 | 4/2004 | Slaker et al. |
| 6,723,119 B2 | 4/2004 | Pinchasik et al. |
| 6,730,116 B1 | 5/2004 | Wolinsky et al. |
| 6,746,475 B1 | 6/2004 | Rivelli, Jr. |
| 6,752,828 B2 | 6/2004 | Thornton |
| 6,755,854 B2 | 6/2004 | Gillick et al. |
| 6,786,922 B2 | 9/2004 | Schaeffer |
| 6,790,221 B2 | 9/2004 | Monroe et al. |
| 6,790,227 B2 | 9/2004 | Burgermeister |
| 6,810,882 B2 | 11/2004 | Langberg et al. |
| 6,814,752 B1 | 11/2004 | Chuter |
| 6,827,731 B2 | 12/2004 | Armstrong et al. |
| 6,843,400 B1 | 1/2005 | Lee |
| 6,846,323 B2 | 1/2005 | Yip et al. |
| 6,849,087 B1 | 2/2005 | Chuter |
| 6,863,685 B2 | 3/2005 | Davila et al. |
| 6,896,697 B1 | 5/2005 | Yip et al. |
| 6,899,718 B2 | 5/2005 | Gifford, III et al. |
| 6,899,914 B2 | 5/2005 | Schaldach et al. |
| 6,913,600 B2 | 7/2005 | Valley et al. |
| 6,942,680 B2 | 9/2005 | Grayzel et al. |
| 6,942,689 B2 * | 9/2005 | Majercak ................ A61F 2/91 623/1.15 |
| 6,945,992 B2 | 9/2005 | Goodson, IV et al. |
| 6,951,554 B2 | 10/2005 | Johansen et al. |
| 6,986,784 B1 | 1/2006 | Weiser et al. |
| 7,001,422 B2 | 2/2006 | Escamilla et al. |
| 7,001,424 B2 | 2/2006 | Patel et al. |
| 7,007,698 B2 | 3/2006 | Thornton |
| 7,018,402 B2 | 3/2006 | Vito et al. |
| 7,025,791 B2 | 4/2006 | Levine et al. |
| 7,037,330 B1 | 5/2006 | Rivelli, Jr. et al. |
| 7,041,130 B2 | 5/2006 | Santini, Jr. et al. |
| 7,052,511 B2 | 5/2006 | Weldon |
| 7,087,088 B2 | 8/2006 | Berg et al. |
| 7,105,016 B2 | 9/2006 | Shiu et al. |
| 7,122,043 B2 | 10/2006 | Greenhalgh et al. |
| 7,137,993 B2 | 11/2006 | Acosta et al. |
| 7,147,655 B2 | 12/2006 | Chermoni |
| 7,147,656 B2 | 12/2006 | Andreas et al. |
| 7,147,661 B2 | 12/2006 | Chobotov et al. |
| 7,150,745 B2 | 12/2006 | Stern et al. |
| 7,160,312 B2 | 1/2007 | Saadat |
| 7,163,552 B2 | 1/2007 | Diaz |
| 7,166,125 B1 | 1/2007 | Baker et al. |
| 7,169,158 B2 | 1/2007 | Sniffin et al. |
| 7,169,163 B2 | 1/2007 | Becker |
| 7,179,284 B2 | 2/2007 | Khosravi et al. |
| 7,192,440 B2 | 3/2007 | Andreas et al. |
| 7,201,770 B2 | 4/2007 | Johnson et al. |
| 7,208,002 B2 | 4/2007 | Shelso |
| 7,211,101 B2 | 5/2007 | Carley et al. |
| 7,243,408 B2 | 7/2007 | Vietmeier |
| 7,258,697 B1 | 8/2007 | Cox et al. |
| 7,261,731 B2 | 8/2007 | Patel et al. |
| 7,267,684 B2 | 9/2007 | Rolando et al. |
| 7,270,673 B2 | 9/2007 | Yee et al. |
| 7,273,492 B2 | 9/2007 | Cheng et al. |
| 7,279,007 B2 | 10/2007 | Nikolic et al. |
| 7,294,146 B2 | 11/2007 | Chew et al. |
| 7,296,577 B2 | 11/2007 | Lashinski et al. |
| 7,300,456 B2 | 11/2007 | Andreas et al. |
| 7,303,572 B2 | 12/2007 | Meisheimer et al. |
| 7,306,617 B2 | 12/2007 | Majercak |
| 7,309,341 B2 | 12/2007 | Ortiz et al. |
| 7,309,350 B2 | 12/2007 | Landreville et al. |
| 7,316,711 B2 | 1/2008 | Allen et al. |
| 7,320,702 B2 | 1/2008 | Hammersmark et al. |
| 7,323,006 B2 | 1/2008 | Andreas et al. |
| 7,323,007 B2 | 1/2008 | Sano |
| 7,326,236 B2 | 2/2008 | Andreas et al. |
| 7,329,279 B2 | 2/2008 | Haug et al. |
| 7,331,987 B1 | 2/2008 | Cox |
| 7,331,990 B2 | 2/2008 | Gianotti |
| 7,331,992 B2 | 2/2008 | Randall et al. |
| 7,351,255 B2 | 4/2008 | Andreas |
| 7,399,307 B2 | 7/2008 | Evans et al. |
| 7,402,168 B2 | 7/2008 | Sanderson et al. |
| 7,431,729 B2 | 10/2008 | Chanduszko |
| 7,445,631 B2 | 11/2008 | Salaheih et al. |
| 7,476,245 B2 | 1/2009 | Abbate |
| 7,500,986 B2 | 3/2009 | Lye et al. |
| 7,510,575 B2 | 3/2009 | Spenser et al. |
| 7,524,330 B2 | 4/2009 | Berreklouw |
| 7,537,607 B2 | 5/2009 | Gerberding |
| 7,556,647 B2 | 7/2009 | Drews et al. |
| 7,578,840 B2 | 8/2009 | Schaeffer |
| 7,604,662 B2 | 10/2009 | Cambronne et al. |
| 7,617,007 B2 | 11/2009 | Williams et al. |
| 7,618,432 B2 | 11/2009 | Pedersen et al. |
| 7,618,447 B2 | 11/2009 | Case et al. |
| 7,625,399 B2 | 12/2009 | Case et al. |
| 7,628,803 B2 | 12/2009 | Pavcnik et al. |
| 7,637,935 B2 | 12/2009 | Pappas et al. |
| 7,655,034 B2 | 2/2010 | Mitchell et al. |
| 7,658,759 B2 | 2/2010 | Case et al. |
| 7,666,216 B2 | 2/2010 | Hogendijk et al. |

(56) References Cited

U.S. PATENT DOCUMENTS

| | | |
|---|---|---|
| 7,686,824 B2 | 3/2010 | Konstantino et al. |
| 7,695,507 B2 | 4/2010 | Rivelli, Jr. et al. |
| 7,720,521 B2 | 5/2010 | Chang et al. |
| 7,736,387 B2 | 6/2010 | Pollock et al. |
| 7,758,594 B2 | 7/2010 | Lamson et al. |
| 7,758,627 B2 | 7/2010 | Richter |
| 7,758,632 B2 | 7/2010 | Hojeibane et al. |
| 7,763,063 B2 | 7/2010 | Arbefeuille et al. |
| 7,806,918 B2 | 10/2010 | Nissl et al. |
| 7,810,223 B2 | 10/2010 | Hemerick et al. |
| 7,828,834 B2 | 11/2010 | Garbe |
| 7,833,262 B2 | 11/2010 | McGuckin, Jr. et al. |
| 7,842,080 B2 | 11/2010 | Chouinard |
| 7,846,194 B2 | 12/2010 | Hartley et al. |
| 7,867,267 B2 | 1/2011 | Sullivan et al. |
| 7,871,431 B2 | 1/2011 | Gurm et al. |
| 7,883,537 B2 | 2/2011 | Grayzel et al. |
| 7,896,911 B2 | 3/2011 | Schneider et al. |
| 7,905,913 B2 | 3/2011 | Chew et al. |
| 7,922,755 B2 | 4/2011 | Acosta et al. |
| 7,933,660 B2 | 4/2011 | Carr |
| 7,942,920 B2 | 5/2011 | Majercak |
| 7,955,315 B2 | 6/2011 | Feinberg et al. |
| 7,963,987 B2 | 6/2011 | Melsheimer et al. |
| 7,967,855 B2 | 6/2011 | Furst et al. |
| 7,972,373 B2 | 7/2011 | Contiliano et al. |
| 8,002,725 B2 | 8/2011 | Hogendijk |
| 8,024,851 B2 | 9/2011 | Barr et al. |
| 8,034,099 B2 | 10/2011 | Pellegrini |
| 8,043,354 B2 | 10/2011 | Greenberg et al. |
| 8,043,357 B2 | 10/2011 | Hartley |
| 8,048,151 B2 | 11/2011 | O'Brien et al. |
| 8,052,738 B2 | 11/2011 | Craven |
| 8,057,543 B2 | 11/2011 | O'Brien et al. |
| 8,092,468 B2 | 1/2012 | Hansen |
| 8,127,422 B2 | 3/2012 | Wu |
| 8,128,677 B2 | 3/2012 | Schneider et al. |
| 8,157,851 B2 | 4/2012 | Andreas |
| 8,177,831 B2 | 5/2012 | Andreas |
| 8,236,045 B2 | 8/2012 | Benichou et al. |
| 8,292,938 B2 | 10/2012 | Case |
| 8,308,790 B2 | 11/2012 | Arbefeuille et al. |
| 8,317,859 B2 | 11/2012 | Snow et al. |
| 8,323,243 B2 | 12/2012 | Schneider et al. |
| 8,328,864 B2 | 12/2012 | Niermann |
| 8,353,945 B2 | 1/2013 | Andreas et al. |
| 8,366,766 B2 | 2/2013 | Berreklouw |
| 8,394,139 B2 | 3/2013 | Roeder et al. |
| 8,403,978 B2 | 3/2013 | Schlun et al. |
| 8,414,636 B2 | 4/2013 | Nabulsi et al. |
| 8,460,357 B2 | 6/2013 | McGarry et al. |
| 8,474,460 B2 | 7/2013 | Barrett et al. |
| 8,500,787 B2 | 8/2013 | Simpson et al. |
| 8,500,789 B2 | 8/2013 | Wuebbeling et al. |
| 8,540,760 B2 | 9/2013 | Paul, Jr. et al. |
| 8,585,747 B2 | 11/2013 | Andreas et al. |
| 8,740,973 B2 | 6/2014 | Furst et al. |
| 8,745,842 B2 | 6/2014 | Wu |
| 8,771,335 B2 | 7/2014 | Griego et al. |
| 8,778,010 B2 | 7/2014 | Venturelli et al. |
| 8,784,467 B2 | 7/2014 | Connelly et al. |
| 8,864,811 B2 | 10/2014 | Kao |
| 8,888,841 B2 | 11/2014 | Pandelidis et al. |
| 8,900,289 B2 | 12/2014 | Thompson |
| 8,956,398 B2 | 2/2015 | George et al. |
| 8,961,583 B2 | 2/2015 | Hojeibane et al. |
| 8,966,736 B2 | 3/2015 | Wu |
| 8,986,362 B2 | 3/2015 | Snow et al. |
| 9,050,181 B2 | 6/2015 | Hartley |
| 9,101,500 B2 | 8/2015 | Feld et al. |
| 9,101,503 B2 | 8/2015 | Lowe et al. |
| 9,113,999 B2 | 8/2015 | Taylor et al. |
| 9,216,082 B2 | 12/2015 | Von Segesser et al. |
| 9,237,959 B2 | 1/2016 | Cage |
| 9,301,864 B2 | 4/2016 | Kao |
| 9,370,437 B2 | 6/2016 | Chuter et al. |
| 9,375,327 B2 | 6/2016 | Giasolli et al. |
| 9,398,967 B2 | 7/2016 | Cornelius |
| 9,452,067 B2 | 9/2016 | Wu |
| 9,480,826 B2 | 11/2016 | Schneider et al. |
| 9,545,322 B2 | 1/2017 | Schneider et al. |
| 9,585,777 B2 | 3/2017 | Pacetti |
| 9,603,730 B2 | 3/2017 | Giasolli et al. |
| 9,603,980 B2 | 3/2017 | Zhao |
| 9,707,115 B2 | 7/2017 | Masakazu |
| 9,730,818 B2 | 8/2017 | Giasolli et al. |
| 9,737,368 B2 | 8/2017 | Lumauig |
| 9,918,835 B2 | 3/2018 | Guyenot et al. |
| 9,974,670 B2 | 5/2018 | Schneider et al. |
| 10,022,250 B2 | 7/2018 | Giasolli et al. |
| 10,117,762 B2 | 11/2018 | Giasolli et al. |
| 10,137,013 B2 | 11/2018 | Giasolli et al. |
| 10,166,127 B2 | 1/2019 | Giasolli et al. |
| 10,188,533 B2 | 1/2019 | Schneider et al. |
| 10,245,167 B2 | 4/2019 | Longo |
| 10,245,168 B2 | 4/2019 | Amendt et al. |
| 10,271,973 B2 | 4/2019 | Giasolli et al. |
| 10,278,839 B2 | 5/2019 | Giasolli et al. |
| 10,285,831 B2 | 5/2019 | Giasolli et al. |
| 10,292,845 B2 | 5/2019 | Higashi et al. |
| 10,299,945 B2 | 5/2019 | Schneider et al. |
| 10,390,977 B2 | 8/2019 | Giasolli et al. |
| 2002/0120323 A1 | 8/2002 | Thompson |
| 2002/0123790 A1 | 9/2002 | White et al. |
| 2002/0165599 A1 | 11/2002 | Nasralla |
| 2002/0169495 A1 | 11/2002 | Gifford et al. |
| 2003/0055491 A1 | 3/2003 | Schwartz et al. |
| 2003/0069630 A1* | 4/2003 | Burgermeister .......... A61F 2/91 623/1.15 |
| 2003/0130720 A1 | 7/2003 | DePalma et al. |
| 2003/0220683 A1 | 11/2003 | Minasian et al. |
| 2003/0225446 A1 | 12/2003 | Hartley |
| 2003/0225448 A1* | 12/2003 | Gerberding .............. A61F 2/91 623/1.15 |
| 2004/0010307 A1 | 1/2004 | Grad et al. |
| 2004/0186551 A1 | 9/2004 | Kao et al. |
| 2004/0215324 A1 | 10/2004 | Vonderwalde et al. |
| 2004/0267348 A1 | 12/2004 | Gunderson et al. |
| 2005/0010275 A1 | 1/2005 | Sahatjian et al. |
| 2005/0096731 A1 | 5/2005 | Looi et al. |
| 2005/0149163 A1 | 7/2005 | Sahota |
| 2005/0246008 A1 | 11/2005 | Hogendijk et al. |
| 2005/0251164 A1 | 11/2005 | Gifford, III et al. |
| 2005/0278011 A1 | 12/2005 | Peckham |
| 2005/0288764 A1 | 12/2005 | Snow et al. |
| 2005/0288766 A1 | 12/2005 | Plain et al. |
| 2006/0069424 A1 | 3/2006 | Acosta et al. |
| 2006/0074478 A1 | 4/2006 | Feller, III |
| 2006/0111769 A1 | 5/2006 | Murray |
| 2006/0184225 A1 | 8/2006 | Pryor |
| 2006/0184227 A1 | 8/2006 | Rust |
| 2006/0206190 A1 | 9/2006 | Chermoni |
| 2006/0248698 A1 | 11/2006 | Hanson et al. |
| 2006/0282149 A1* | 12/2006 | Kao ........................ A61F 2/91 623/1.11 |
| 2007/0038291 A1* | 2/2007 | Case ..................... A61F 2/2418 623/1.16 |
| 2007/0088420 A1 | 4/2007 | Andreas et al. |
| 2007/0093744 A1 | 4/2007 | Elmaleh |
| 2007/0156223 A1 | 7/2007 | Vaughan |
| 2007/0156225 A1 | 7/2007 | George et al. |
| 2007/0156226 A1 | 7/2007 | Chew et al. |
| 2007/0179587 A1 | 8/2007 | Acosta et al. |
| 2007/0191926 A1 | 8/2007 | Nikanorov et al. |
| 2008/0033522 A1 | 2/2008 | Grewe et al. |
| 2008/0051867 A1 | 2/2008 | Davila et al. |
| 2008/0077229 A1 | 3/2008 | Andres et al. |
| 2008/0082154 A1 | 4/2008 | Tseng et al. |
| 2008/0132999 A1 | 6/2008 | Mericle et al. |
| 2008/0208327 A1 | 8/2008 | Rowe |
| 2008/0221658 A1 | 9/2008 | Martin et al. |
| 2008/0255653 A1 | 10/2008 | Schkolnik |
| 2008/0264102 A1 | 10/2008 | Berra |
| 2008/0269865 A1 | 10/2008 | Snow et al. |

(56) References Cited

U.S. PATENT DOCUMENTS

| | | | |
|---|---|---|---|
| 2008/0319528 A1 | 12/2008 | Yribarren et al. | |
| 2009/0076594 A1 | 3/2009 | Sabaria | |
| 2009/0082841 A1 | 3/2009 | Zacharias et al. | |
| 2009/0149943 A1 | 6/2009 | Tower | |
| 2009/0216284 A1 | 8/2009 | Chin et al. | |
| 2009/0248141 A1 | 10/2009 | Shandas et al. | |
| 2009/0270965 A1 | 10/2009 | Sinha et al. | |
| 2009/0270967 A1 | 10/2009 | Fleming, III et al. | |
| 2009/0276031 A1 | 11/2009 | Kao | |
| 2010/0131045 A1 | 5/2010 | Globerman et al. | |
| 2010/0137966 A1* | 6/2010 | Magnuson | A61F 2/95 623/1.11 |
| 2010/0228333 A1 | 9/2010 | Drasler et al. | |
| 2010/0318173 A1 | 12/2010 | Kolandaivelu et al. | |
| 2011/0077731 A1 | 3/2011 | Lee et al. | |
| 2011/0230954 A1 | 9/2011 | Schneider et al. | |
| 2012/0016457 A1 | 1/2012 | Chobotov et al. | |
| 2012/0191176 A1 | 7/2012 | Nagl et al. | |
| 2014/0194967 A1 | 7/2014 | Schneider et al. | |
| 2017/0181873 A1 | 6/2017 | Schneider et al. | |
| 2017/0296366 A1 | 10/2017 | Giasolli et al. | |
| 2017/0319364 A1 | 11/2017 | Jung et al. | |
| 2017/0367856 A1 | 12/2017 | Tanaka et al. | |
| 2018/0200086 A1 | 7/2018 | Giasolli et al. | |
| 2018/0207008 A1 | 7/2018 | Giasolli et al. | |
| 2019/0192319 A1 | 6/2019 | Giasolli et al. | |
| 2019/0192321 A1 | 6/2019 | Schneider et al. | |

FOREIGN PATENT DOCUMENTS

| | | |
|---|---|---|
| AU | 2014201067 | 3/2014 |
| AU | 2010259907 | 8/2015 |
| AU | 2013212056 | 7/2016 |
| AU | 2015207895 | 5/2017 |
| AU | 2014280976 | 7/2017 |
| CA | 2705275 | 7/2013 |
| CN | 1856280 | 11/2006 |
| CN | 101102728 | 1/2008 |
| CN | 101262835 | 9/2008 |
| CN | 101754727 | 6/2010 |
| CN | 101909552 | 12/2010 |
| CN | 102292036 | 12/2011 |
| CN | 102724931 | 10/2012 |
| CN | 103313682 | 8/2016 |
| CN | 104220026 | 9/2016 |
| CN | 106466205 | 3/2017 |
| CN | 106473786 | 3/2017 |
| CN | 106473849 | 3/2017 |
| CN | 107028691 | 8/2017 |
| CN | 107157632 | 9/2017 |
| CN | 107205834 | 9/2017 |
| CN | 104887365 | 12/2017 |
| DE | 60030705 | 5/2007 |
| DE | 10 2009 041 025 | 3/2011 |
| DE | 20 2011 107 781 | 12/2011 |
| DE | 20 2011 110 714 | 12/2015 |
| DE | 10 2014 016 588 | 5/2016 |
| DE | 20 2011 110 818 | 9/2016 |
| DK | 2775968 | 12/2017 |
| EP | 0497620 | 8/1992 |
| EP | 0714640 | 6/1996 |
| EP | 0855883 | 8/1998 |
| EP | 0812580 | 2/2004 |
| EP | 1393766 | 3/2004 |
| EP | 1236446 | 8/2005 |
| EP | 1803423 | 7/2007 |
| EP | 1894545 | 3/2008 |
| EP | 1452151 | 10/2008 |
| EP | 1378212 | 9/2009 |
| EP | 2219535 | 8/2010 |
| EP | 2440155 | 4/2012 |
| EP | 1786367 | 4/2013 |
| EP | 1973502 | 4/2014 |
| EP | 2806826 | 12/2014 |
| EP | 2881086 | 6/2015 |
| EP | 2699207 | 10/2015 |
| EP | 2590602 | 12/2015 |
| EP | 3015078 | 5/2016 |
| EP | 3058900 | 8/2016 |
| EP | 1689327 | 9/2016 |
| EP | 3072463 | 9/2016 |
| EP | 2775968 | 9/2017 |
| EP | 3217927 | 9/2017 |
| FR | 2714816 | 7/1995 |
| GB | 201106757 | 6/2011 |
| JP | H06-000221 | 1/1994 |
| JP | H08-332229 | 12/1996 |
| JP | H11-501526 | 2/1999 |
| JP | H11-506665 | 6/1999 |
| JP | 2007-503923 | 3/2007 |
| JP | 2008-504078 | 2/2008 |
| JP | 2008-246214 | 10/2008 |
| JP | 2008-537891 | 10/2008 |
| JP | 2010-516333 | 5/2010 |
| JP | 2016-135278 | 7/2016 |
| JP | 6006808 | 10/2016 |
| KR | 10-2017-0084214 | 7/2017 |
| WO | WO 1996/009013 | 3/1996 |
| WO | WO 1996/037167 | 11/1996 |
| WO | WO 1999/048440 | 9/1999 |
| WO | WO 1999/049440 | 9/1999 |
| WO | WO 2000/066034 | 11/2000 |
| WO | WO 2001/076509 | 10/2001 |
| WO | WO 2002/034163 | 5/2002 |
| WO | WO 2003/047651 | 6/2003 |
| WO | WO 2003/101310 | 12/2003 |
| WO | WO 2004/006983 | 1/2004 |
| WO | WO 2004/032799 | 4/2004 |
| WO | WO 2006/005082 | 1/2006 |
| WO | WO 2006/026371 | 3/2006 |
| WO | WO 2007/088549 | 8/2007 |
| WO | WO 2007/109621 | 9/2007 |
| WO | WO 2009/076517 | 6/2009 |
| WO | WO 2010/037141 | 4/2010 |
| WO | WO 2010/118432 | 10/2010 |
| WO | WO 2010/144845 | 12/2010 |
| WO | WO 2011/153110 | 12/2011 |
| WO | WO 2012/006602 | 1/2012 |
| WO | WO 2012/143731 | 10/2012 |
| WO | WO 2013/068127 | 5/2013 |
| WO | WO 2013/112768 | 8/2013 |
| WO | WO 2016/074799 | 5/2016 |

OTHER PUBLICATIONS

Bosiers, M. et al., "Results from the Tack Optimized Balloon Angioplasty (TOBA) study demonstrate the benefits of minimal metal implants for dissection repair after angioplasty", Journal of Vascular Surgery, vol. 64, Jul. 2016, in 8 pages.
Colombo, A. et al., "Intravascular Ultrasound-Guided Percutaneous Transluminal Coronary Angioplasty With Provisional Spot Stenting for Treatment of Long Coronary Lesions", Journal of the American College of Cardiology, vol. 38, No. 5, Nov. 1, 2001, in 9 pages.
Kokkinidis, D. et al., "Emerging and Future Therapeutic Options for Femoropopliteal and Infrapopliteal Endovascular Intervention", Interventional Cardiology Clinics, vol. 6, 2017, in 17 pages.
Mosseri, M. et al., "New Indicator for Stent Covering Area", in Catheterization and Cardiovascular Diagnosis, 1998, vol. 44, in 5 pages.
Shishehbor, M. et al., "Endovascular Treatment of Femoropopliteal Lesions", Journal of the American College of Cardiology, vol. 66, 2015, in 4 pages.
Zeller, T. et al., "Novel Approaches to the Management of Advanced Peripheral Artery Disease: Perspectives on Drug-Coated Balloons, Drug-Eluting Stents, and Bioresorbable Scaffolds", Current Cardiology Reports, vol. 17, Sep. 2015, in 6 pages.
Australian Office Action (Notice of Acceptance), re AU Application No. 2011274392, dated Nov. 14, 2013, including accepted (allowed) claims.

(56) References Cited

OTHER PUBLICATIONS

Australian Office Action, re AU Application No. 2008335140, dated Apr. 21, 2011.
Australian Office Action, re AU Application No. 2008335140, dated Mar. 15, 2011.
Australian Office Action, re AU Application No. 2011274392, dated May 3, 2013.
English translation of the first Office Action and Search Report in Chinese Application No. 201610546800.2 in 5 pages dated Sep. 28, 2017.
English translation of the first Office Action and Search Report in Chinese Application No. 201610546643.5 in 5 pages dated Oct. 17, 2017.
European Office Action and Supplementary Partial European Search Report, re EP Application No. 08858824.9, dated Sep. 27, 2012.
International Preliminary Report on Patentability, re PCT Application No. PCT/US2008/086396, dated Jun. 15, 2010.
International Preliminary Report on Patentability, re PCT Application No. PCT/US2011/038468, dated Dec. 13, 2012.
International Preliminary Report on Patentability, re PCT Application No. PCT/US2011/043471, dated Jan. 17, 2013.
International Preliminary Report on Patentability, re PCT Application No. PCT/US2013/023030, dated Aug. 7, 2014.
International Search Report and Written Opinion, re PCT Application No. PCT/US2010/038379, dated Feb. 25, 2011.
International Search Report and Written Opinion, re PCT Application No. PCT/US2011/038468, dated Jan. 18, 2012.
International Search Report and Written Opinion, re PCT Application No. PCT/US2013/023030, dated Apr. 16, 2013.
International Search Report and Written Opinion, re PCT Application PCT/US2008/086396, dated Jul. 27, 2009.
International Search Report and Written Opinion, re PCT Application PCT/US2011/043471, dated Feb. 9, 2012.
U.S. Appl. No. 11/955,331 (U.S. Pat. No. 7,896,911), filed Dec. 12, 2007 (Mar. 1, 2011), Device and Method for Tacking Plaque to Blood Vessel Wall.
U.S. Appl. No. 15/375,026, filed Dec. 9, 2016, Device and Method for Tacking Plaque to Blood Vessel Wall.
U.S. Appl. No. 13/038,175 (U.S. Pat. No. 9,545,322), filed Mar. 1, 2011 (Jan. 17, 2017), Device and Method for Tacking Plaque to Blood Vessel Wall.
U.S. Appl. No. 12/483,193 (U.S. Pat. No. 8,128,677), filed Jun. 11, 2009 (Mar. 6, 2012), Device and Method for Tacking Plaque to a Blood Vessel Wall.
U.S. Appl. No. 13/246,776 (U.S. Pat. No. 9,974,670), filed Sep. 27, 2011 (May 22, 2018), Method of Treating Atherosclerotic Occlusive Disease.
U.S. Appl. No. 15/984,111 (U.S. Pat. No. 10,299,945), filed May 18, 2018 (May 28, 2019), Method of Treating Atherosclerotic Occlusive Disease.
U.S. Appl. No. 14/102,411, filed Dec. 10, 2013, Method of Treating Atherosclerotic Occlusive Disease.
U.S. Appl. No. 12/790,819 (U.S. Pat. No. 10,188,533), filed May 29, 2010 (Jan. 29, 2019), Minimal Surface Area Contact Device for Holding Plaque to Blood Vessel Wall.
U.S. Appl. No. 16/259,146, filed Jan. 28, 2019, Minimal Surface Area Contact Device for Holding Plaque to Blood Vessel Wall.
U.S. Appl. No. 13/118,388, filed May 28, 2011, Stent Device Having Focal Elevating Elements for Minimal Surface Area Contact With Lumen Walls.
U.S. Appl. No. 13/179,458 (U.S. Pat. No. 10,022,250), filed Jul. 8, 2011 (Jul. 17, 2018), Deployment Device for Placement of Multiple Intraluminal Surgical Staples.
U.S. Appl. No. 15/815,515, filed Nov. 16, 2017, Deployment Device for Placement of Multiple Intraluminal Surgical Staples.
U.S. Appl. No. 15/921,464, filed Mar. 14, 2018, Deployment Device for Placement of Multiple Intraluminal Surgical Staples.
U.S. Appl. No. 13/153,257 (U.S. Pat. No. 9,375,327), filed Jun. 3, 2011 (Jun. 28, 2016), Endovascular Implant.
U.S. Appl. No. 15/170,772 (U.S. Pat. No. 10,278,839), filed Jun. 1, 2016 (May 7, 2019), Endovascular Implant.
U.S. Appl. No. 15/640,095, filed Jun. 30, 2017, Endovascular Implant.
U.S. Appl. No. 15/921,448 (U.S. Pat. No. 10,285,831), filed Mar. 14, 2018 (May 14, 2019), Endovascular Implant.
U.S. Appl. No. 15/921,459 (U.S. Pat. No. 10,390,977) filed Mar. 14, 2018 (Aug. 27, 2019), Endovascular Implant.
U.S. Appl. No. 15/921,477 (U.S. Pat. No. 10,271,973), filed Mar. 14, 2018 (Apr. 30, 2019), Endovascular Implant.
U.S. Appl. No. 13/749,643 (U.S. Pat. No. 9,730,818), filed Jan. 24, 2013 (Aug. 15, 2017), Endoluminal Device and Method.
U.S. Appl. No. 14/089,703 (U.S. Pat. No. 9,603,730), filed Nov. 25, 2013 (Mar. 28, 2017), Endoluminal Device and Method.
U.S. Appl. No. 15/472,215, filed Mar. 28, 2017, Endoluminal Device and Method.
U.S. Appl. No. 15/654,586 (U.S. Pat. No. 10,117,762), filed Jul. 19, 2017 (Nov. 6, 2018), Endoluminal Device and Method.
U.S. Appl. No. 15/837,870 (U.S. Pat. No. 10,137,013), filed Dec. 11, 2017 (Nov. 27, 2018), Endoluminal Device and Method.
U.S. Appl. No. 15/921,541 (U.S. Pat. No. 10,166,127), filed Mar. 14, 2018 (Jan. 1, 2019), Endoluminal Device and Method.
U.S. Appl. No. 16/225,528, filed Dec. 19, 2018, Endoluminal Device and Method.
U.S. Appl. No. 13/939,019, filed Jul. 10, 2013, Systems and Methods for Attaching Radiopaque Markers to a Medical Device.
U.S. Appl. No. 14/746,636 (U.S. Pat. No. 9,192,500), filed Jun. 22, 2015 (Nov. 24, 2015), Delivery Device and Method of Delivery.
U.S. Appl. No. 14/885,295 (U.S. Pat. No. 9,375,337), filed Oct. 16, 2015 (Jun. 28, 2016), Delivery Device and Method of Delivery.
U.S. Appl. No. 15/133,709, filed Apr. 20, 2016, Delivery Device and Method of Delivery.
U.S. Appl. No. 14/935,087 (U.S. Pat. No. 9,345,603), filed Nov. 6, 2015 (May 24, 2016), Delivery Device and Method of Delivery.
U.S. Appl. No. 15/133,751 (U.S. Pat. No. 9,602,786), filed Apr. 20, 2016 (Mar. 21, 2017), Delivery Device and Method of Delivery.
U.S. Appl. No. 14/935,121 (U.S. Pat. No. 9,320,632), filed Nov. 6, 2015 (Apr. 26, 2016), Delivery Device and Method of Delivery.
U.S. Appl. No. 15/133,158 (U.S. Pat. No. 9,584,777), filed Apr. 19, 2016 (Feb. 28, 2017), Delivery Device and Method of Delivery.
U.S. Appl. No. 15/011,321 (U.S. Pat. No. 9,456,914), filed Jan. 29, 2016 (Oct. 4, 2016), Delivery Device and Method of Delivery.
U.S. Appl. No. 15/134,315 (U.S. Pat. No. 9,585,782), filed Apr. 20, 2016 (Mar. 7, 2017), Delivery Device and Method of Delivery.
U.S. Appl. No. 15/415,167, filed Jan. 25, 2017, Delivery Device and Method of Delivery.
U.S. Appl. No. 14/656,462 (U.S. Pat. No. 9,375,336), filed Mar. 12, 2015 (Jun. 28, 2016), Delivery Device and Method of Delivery.
U.S. Appl. No. 14/935,154 (U.S. Pat. No. 9,445,929), filed Nov. 6, 2015 (Sep. 20, 2016), Delivery Device and Method of Delivery.
U.S. Appl. No. 15/194,410, filed Jun. 27, 2016, Delivery Device and Method of Delivery.
U.S. Appl. No. 15/000,437 (U.S. Pat. No. 9,433,520), filed Jan. 19, 2016 (Sep. 6, 2016), Delivery Device and Method of Delivery.
U.S. Appl. No. 15/227,757 (U.S. Pat. No. 10,245,167), filed Aug. 3, 2016 (Apr. 2, 2019), Delivery Device and Method of Delivery.
U.S. Appl. No. 16/372,224, filed Apr. 1, 2019, Delivery Device and Method of Delivery.
U.S. Appl. No. 16/067,082, filed Jun. 28, 2018, Delivery Device and Method of Delivery.
U.S. Appl. No. 15/705,793, filed Sep. 15, 2017, Delivery Device and Method of Delivery.

* cited by examiner

FEE

FEE

ENDOVASCULAR IMPLANT AND DEPLOYMENT DEVICES

CROSS-REFERENCE TO RELATED APPLICATIONS

This application is a continuation of U.S. patent application Ser. No. 15/640,095, filed on Jun. 30, 2017, which is a continuation of U.S. patent application Ser. No. 15/170,772, filed on Jun. 1, 2016 and issued as U.S. Pat. No. 10,278,839 on May 7, 2019, which is a continuation of U.S. patent application Ser. No. 13/153,257, filed on Jun. 3, 2011 and issued as U.S. Pat. No. 9,375,327 on Jun. 28, 2016, and this application is a continuation of U.S. patent application Ser. No. 15/921,459, filed on Mar. 14, 2018, which is a continuation of U.S. patent application Ser. No. 15/170,772, filed on Jun. 1, 2016 and issued as U.S. Pat. No. 10,278,839 on May 7, 2019, which is a continuation of U.S. patent application Ser. No. 13/153,257, filed on Jun. 3, 2011 and issued as U.S. Pat. No. 9,375,327 on Jun. 28, 2016. U.S. patent application Ser. No. 13/153,257 is a continuation-in-part of U.S. patent application Ser. No. 12/790,819, filed on May 29, 2010 and issued as U.S. Pat. No. 10,188,533 on Jan. 29, 2019, which is a continuation-in-part of U.S. patent application Ser. No. 12/483,193, filed on Jun. 11, 2009 and issued as U.S. Pat. No. 8,128,677 on Mar. 6, 2012, which is a continuation-in-part of U.S. patent application Ser. No. 11/955,331, filed on Dec. 12, 2007 and issued as U.S. Pat. No. 7,896,911 on Mar. 1, 2011. All of the above applications are incorporated by reference herein and made a part of this specification.

BACKGROUND OF THE INVENTION

Field of the Invention

This invention relates to treatment of atherosclerotic occlusive disease by intravascular procedures for pushing and holding plaque accumulated on the blood vessel walls out of the way for reopened blood flow.

Atherosclerotic occlusive disease is the primary cause of stroke, heart attack, limb loss, and death in the US and the industrialized world. Atherosclerotic plaque forms a hard layer along the wall of an artery and is comprised of calcium, cholesterol, compacted thrombus and cellular debris. As the atherosclerotic disease progresses, the blood supply intended to pass through a specific blood vessel is diminished or even prevented by the occlusive process. One of the most widely utilized methods of treating clinically significant atherosclerotic plaque is balloon angioplasty.

Balloon angioplasty is an accepted method of opening blocked or narrowed blood vessels in every vascular bed in the body. Balloon angioplasty is performed with a balloon angioplasty catheter. The balloon angioplasty catheter consists of a cigar shaped, cylindrical balloon attached to a catheter. The balloon angioplasty catheter is placed into the artery from a remote access site that is created either percutaneously or through open exposure of the artery. The catheter is passed along the inside of the blood vessel over a wire that guides the way of the catheter. The portion of the catheter with the balloon attached is placed at the location of the atherosclerotic plaque that requires treatment. The balloon is inflated to a size that is consistent with the original diameter of the artery prior to developing occlusive disease. When the balloon is inflated, the plaque is broken. Cleavage planes form within the plaque, permitting the plaque to expand in diameter with the expanding balloon. Frequently, a segment of the plaque is more resistant to dilatation than the remainder of the plaque. When this occurs, greater pressure pumped into the balloon results in full dilatation of the balloon to its intended size. The balloon is deflated and removed and the artery segment is reexamined. The process of balloon angioplasty is one of uncontrolled plaque disruption. The lumen of the blood vessel at the site of treatment is usually somewhat larger, but not always and not reliably.

Some of the cleavage planes created by fracture of the plaque with balloon angioplasty can form a dissection. A dissection occurs when a portion of the plaque is lifted away from the artery, is not fully adherent to the artery and may be mobile or loose. The plaque that has been disrupted by dissection protrudes into the flow stream. If the plaque lifts completely in the direction of blood flow, it may impede flow or cause acute occlusion of the blood vessel. There is evidence that dissection after balloon angioplasty must be treated to prevent occlusion and to resolve residual stenosis. There is also evidence that in some circumstances, it is better to place a metal retaining structure, such as stent to hold open the artery after angioplasty and force the dissected material back against the wall of the blood vessel to create an adequate lumen for blood flow.

The clinical management of dissection after balloon angioplasty is currently performed primarily with stents. As illustrated in FIG. 1, a stent 3 is a tube having a diameter that is sized to the artery 7. A stent is placed into the artery at the location of a dissection to force the dissection flap against the inner wall of the blood vessel. Stents are usually made of metal alloys. They have varying degrees of flexibility, visibility, and different placement techniques. Stents are placed in every vascular bed in the body. The development of stents has significantly changed the approach to minimally invasive treatment of vascular disease, making it safer and in many cases more durable. The incidence of acute occlusion after balloon angioplasty has decreased significantly with stents.

However, stents have significant disadvantages and much research and development is being done to address these issues. Stents induce repeat narrowing of the treated blood vessel (recurrent stenosis). Recurrent stenosis is the "Achilles heel" of stenting. Depending on the location and the size of the artery, in-growth of intimal hyperplastic tissue from the vessel wall in between struts or through openings in the stent may occur and cause failure of the vascular reconstruction by narrowing or occlusion of the stent. This may occur any time after stent placement. In many cases, the stent itself seems to incite local vessel wall reaction that causes stenosis, even in the segment of the stent that was placed over artery segments that were not particularly narrowed or diseased during the original stent procedure. This reaction of the blood vessel to the presence of the stent is likely due to the scaffolding effect of the stent. This reaction of recurrent stenosis or tissue in growth of the blood vessel is in response to the stent. This activity shows that the extensive use of metal and vessel coverage in the artery as happens with stenting is contributing to the narrowing. The recurrent stenosis is a problem because it causes failure of the stent and there is no effective treatment. Existing treatment methods that have been used for this problem include; repeat angioplasty, cutting balloon angioplasty, cryoplasty, atherectomy, and even repeat stenting. None of these methods have a high degree of long-term success.

Stents may also fracture due to material stress. Stent fracture may occur with chronic material stress and is associated with the development of recurrent stenosis at the site of stent fracture. This is a relatively new finding and it may require specialized stent designs for each application in each vascular bed. Structural integrity of stents remains a current issue for their use. Arteries that are particularly mobile, such as the lower extremity arteries and the carotid arteries, are of particular concern. The integrity of the entire stent is tested any time the vessel bends or is compressed anywhere along the stented segment. One reason why stent fractures may occur is because a longer segment of the artery has been treated than is necessary. The scaffolding effect of the stent affects the overall mechanical behavior of the artery, making the artery less flexible. Available stenting materials have limited bending cycles and are prone to failure at repeated high frequency bending sites.

Many artery segments are stented even when they do not require it, thereby exacerbating the disadvantages of stents. There are several reasons for this. Many cases require more than one stent to be placed and often several are needed. Much of the stent length is often placed over artery segments that do not need stenting and are merely adjoining an area of dissection or disease. Stents that are adjusted to the precise length of the lesion are not available. When one attempts to place multiple stents and in the segments most in need of stenting, the cost is prohibitive since installation and material is required per stent. The time it takes to do this also adds to the cost and risk of the procedure. The more length of artery that receives a stent that it does not need, the more stiffness is conferred to the artery, and the more scaffolding affect occurs. This may also help to incite the arterial reaction to the stent that causes recurrent stenosis.

SUMMARY OF THE INVENTION

There exists a continuing need to develop new and improved devices to assist in the treatment of vascular disease, including atherosclerotic occlusive disease, among other conditions, and such as for the purposes outlined above. Some embodiments of an endoluminal staple or tack device can include one or more of the following features: a single column cell design, controlled angle of struts, tapered struts, struts having more than one sinusoidal pattern amplitude, a row of anchors, anchors in the middle of the device, flat midline markers, simultaneous device placement, and a force curve with a slope of about −0.3 N/mm or less. In certain embodiments, an endoluminal staple is provided with a force curve having a slope within a range of about −0.1 to about −0.3 N/mm. In other embodiment, an endoluminal staple is provided with a force curve having a slope within a range of about −0.06 to about −0.1 N/mm. In other embodiment, an endoluminal staple is provided with a force curve having a slope within a range of about −0.006 to about −0.06 N/mm.

Some embodiments of a catheter based endoluminal staple device, or plaque tack, can have a single column cell design.

A catheter based endoluminal staple can include proximal and distal circumferential members. The proximal circumferential member can be disposed at a proximal end of the endoluminal staple. The distal circumferential member can be disposed at a distal end of the endoluminal staple. In some embodiments, the distal circumferential member is the distal most aspect of the endoluminal staple and the proximal circumferential member is the proximal most aspect of the endoluminal staple. The proximal and distal circumferential members can be connected by bridge members. The bridge members can divide an outer surface of the endoluminal staple into cells bounded by the bridge members and a portion of each of the proximal and distal circumferential members.

A catheter based endoluminal staple can include proximal and distal circumferential members. The proximal circumferential member can be disposed at a proximal end of the endoluminal staple, the proximal circumferential member having a sinusoidal configuration. The distal circumferential member can be disposed at a distal end of the endoluminal staple, the distal circumferential member having a sinusoidal configuration. In some embodiments, the distal circumferential member is the distal most aspect of the endoluminal staple and the proximal circumferential member is the proximal most aspect of the endoluminal staple.

In some embodiments, the endoluminal staple can include a first plurality of distally extending apices having a first amplitude and a second plurality of distally extending apices having a second amplitude greater than the first amplitude. It may also, or alternatively, have a first plurality of proximally extending apices having a first amplitude and a second plurality of proximally extending apices having a second amplitude greater than the first amplitude.

In some embodiments, the endoluminal staple can include a bridge member connecting each apex of the second plurality of apices of the proximal circumferential member to each apex of the second plurality of apices of the distal circumferential member. In addition, or alternatively, at an axially aligned position, each apex of the first plurality of apices of the proximal circumferential member can be unconnected to each apex of the first plurality of apices of the distal circumferential member at a corresponding circumferential position.

In certain embodiments, a staple is configured with a plurality of struts on a circumferential member and one or more angles between the struts is controlled. In particular, the angles of the outward apexes of the circumferential member can be controlled. By controlling these angles in particular, production run quality can be improved and the staple is better able to distribute stresses evenly along the circumferential member.

In other embodiments, an endoluminal staple is provided that includes a plurality of circumferential members, at least one of which comprises a plurality of struts. The struts can be configured with a taper along their length, to control the manner in which the struts are loaded. The taper can be the same or different along each strut or along each type of strut. For example, each circumferential member can be made up of a pattern of repeating struts, with each type of strut having a particular taper. In some embodiments, the struts can alternate from a wider end to a shorter end and then the next strut can have a shorter end followed by a wider end. Other configurations are also possible, increasingly wider struts being just one additional example.

As another example, a circumferential member with a plurality of struts can be on a distal end of an endoluminal staple. A first strut can be tapered such that a proximal portion of the strut is narrower than a distal portion of the strut. A second strut is connected to the first strut at distal ends of the first and second struts. The second strut can have the same or a different taper. For example, the second strut can also have a proximal portion narrower than a distal portion of the second strut, while also being narrower overall than the first strut. A third strut can be connected to the second strut at proximal ends of the second and third struts. The third strut can have a proximal portion of the strut that is wider than a distal portion of the strut. A fourth strut can be connected to the third strut at distal ends of the third and fourth struts. The fourth strut can have a proximal portion of the strut that is wider than a distal portion of the strut. The fourth strut can have the same or a different taper from the third strut. For example, the fourth strut can wider overall than the third strut.

In certain embodiments, an endoluminal staple has a first circumferential member disposed at a distal end of the endoluminal staple, the first circumferential member comprising a repeating pattern of first and second outward apices spaced apart by first and second inward apices. The amplitude of the second outward apices can be less than the amplitude of the first apices. The endoluminal staple can also have a second circumferential member disposed at a proximal end. The second circumferential member can be a mirror image of the first circumferential member.

In certain embodiments, an endoluminal staple has a first circumferential member disposed at a distal end of the endoluminal staple and a second circumferential member disposed at a proximal end. The second circumferential member can be a mirror image of the first circumferential member. The first and second circumferential members can be connected by a plurality of bridge members. In some embodiments, the bridge members can include one or more anchors configured to engage the plaque and/or the blood vessel wall.

In certain embodiments, an endoluminal staple can be configured for simultaneous deployment wherein the entire staple is released from the delivery catheter prior to the staple contacting the blood vessel lumen where it is to be placed. Simultaneous deployment is most likely in larger vessels, for example, vessels larger than (e.g., having a diameter that is larger than) 80% of the length of the staple will generally permit simultaneous deployment. For one embodiment of the endoluminal staple, such vessels include superficial femoral artery, iliac, popliteal, and tibial.

In certain embodiments, an endoluminal staple is provided with features that allow the staple to remain in a delivery catheter after a delivery sheath has been withdrawn releasing at least part of, or an entire circumferential member. The circumferential member can make up almost one half of an axial length of the staple. The staple can also be configured for simultaneous deployment when released.

In certain embodiments, an endoluminal staple can have a force curve with an extended area having a low slope. A force curve plots the amount of expansive force exerted, e.g., radially outwardly directed, by a self expanding staple or stent when moving from a compressed state to an expanded state. In some embodiments, the low slope of the force curve can be over a 2.5 mm outer diameter expansion range with a change in force of less than 1 N. In some embodiments, the slope can be less than −0.3 N/mm.

A tack device can be used in a method to treat any plaque dissection in the blood vessel after balloon angioplasty by installing the tack with an expansion force against the plaque to hold it against the blood vessel walls. One method encompasses one wherein balloon angioplasty is first performed, and if there is any damage, disruption, dissection, or irregularity to the blood vessel caused by the balloon angioplasty mechanism, one or more tack devices may be used to tack down the damaged, disrupted, dissected, or irregular blood vessel surface, so as to avoid the need to install a stent and thereby maintain a "stent-free" environment.

BRIEF DESCRIPTION OF THE DRAWINGS

These and other features, aspects and advantages are described below with reference to drawings of preferred embodiments, which are intended to illustrate but not to limit the present invention.

DETAILED DESCRIPTION OF THE PREFERRED EMBODIMENT

The subject matter of this application is directed to the improvement of a plaque tack or staple device. The plaque tack or staple device can be used for treating atherosclerotic occlusive disease. The plaque tack can be used to hold loose plaque against a blood vessel wall. The plaque tack can include an annular member configured to apply an expansion force to the loose plaque.

I. Overview of Endolumenal Tack Treatment

Figure 1:
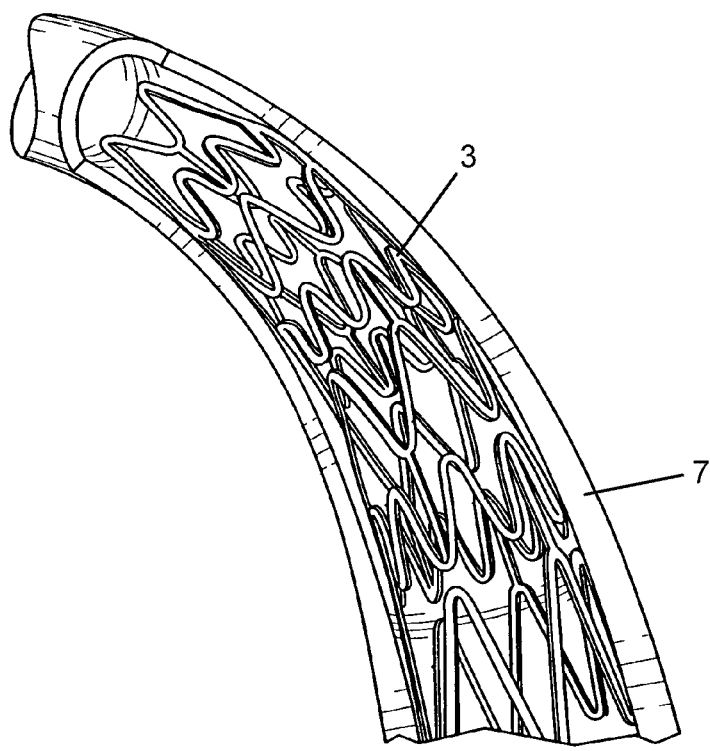
FIG. 1 illustrates the use of a stent installed after angioplasty as conventionally practiced in the prior art.
Figure 2:
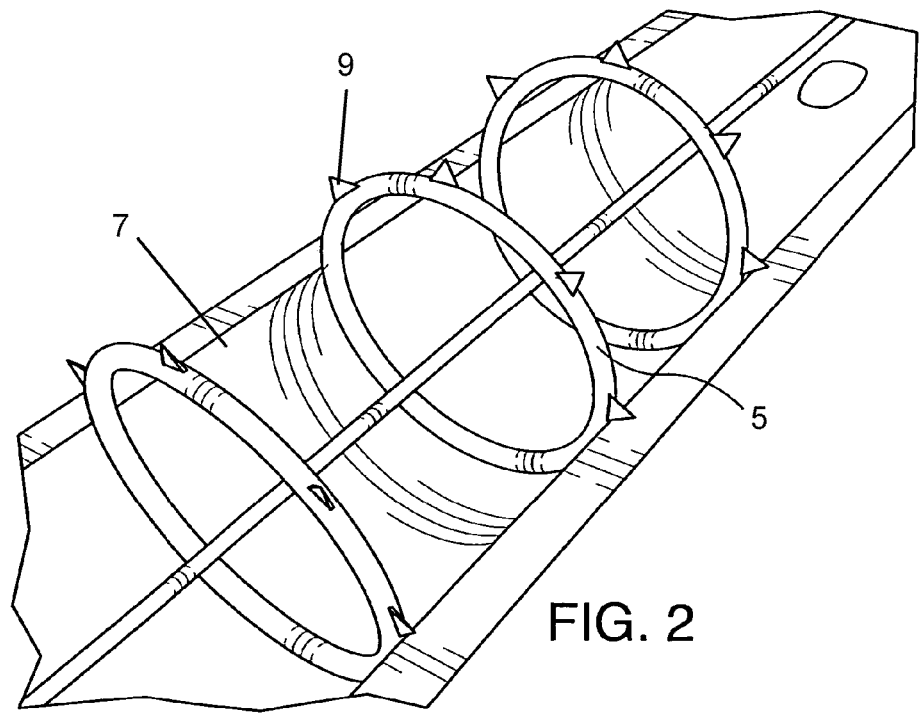
FIG. 2 illustrates the use of plaque tacks installed after an endolumenal procedure demonstrating advantages over the prior art.

FIG. 2 shows one embodiment of a plaque tack or staple device 5 that includes a thin, annular band or ring of durable, flexible material. The tack device can be inserted into a blood vessel in a compressed state and installed in an expanded state against the blood vessel wall using a catheter delivery mechanism at one or more specific positions of loose plaque. The plaque tack 5 can be deployed after or as part of an angioplasty procedure. The plaque tack 5 is adapted to apply an expansion force against the plaque in the blood vessel 7 to press and hold the plaque against the blood vessel walls. The tack device can be radially outwardly expandable under a spring or other expansion force. Preferably the fully expanded diameter of the tack 5 is greater than the transverse size of the vessel to be treated. As discussed below, the tack 5 advantageously can be deployed in a surprising large range of blood vessel sizes.

The plaque tack 5 can include a plurality of plaque anchors 9 on its outer annular periphery. The plaque anchors 9 can be embedded into or at least placed in physical contact with plaque by expanding up against the plaque. In certain embodiments, the plaque anchors 9 are adapted to elevate adjacent sections of the tack 5 relative to the wall of the vessel. In at least this sense, the anchors 9 may have some of the advantages of focal elevating elements that are discussed in SECTION III below. The anchors 9 exert a holding force on the plaque while minimizing the amount of material surface area in contact with the plaque or blood vessel wall. As another feature, the plaque tack 5 can extend over only a small area in the axial direction of the vessel wall, in order to minimize the amount of foreign structure placed in the blood vessel. For example, each plaque tack 5 can have an axial length L that is only a small fraction of the axial length of a typical stent.

The plaque tack devices of the present application are designed as a minimally invasive approach to tacking loose or dissected atherosclerotic plaque to the wall of the artery, as illustrated in FIG. 2. The plaque tack may be used to treat either de novo atherosclerotic lesions or the inadequate results of balloon angioplasty. The plaque tack is designed to maintain adequate lumen in a treated artery without the inherent disadvantages of vascular stents. The device may also be used to administer medications, fluid, or other treatment ("eluting") agents into the atherosclerotic plaque or the wall of the blood vessel or into the bloodstream.

One or more plaque tacks 5 can be accurately deployed in positions along the length of a plaque accumulation site where specific holding forces are needed to stabilize the site and/or hold pieces of plaque out of the way of blood flow.

FIG. 2 shows that in various plaque tack treatments, a plurality of plaque tacks 5 can be deployed to treat locations that are axially spaced along the vessel 7. In this way, targeted treatments can be provided to hold loose plaque against a vessel wall without over-scaffolding as discussed below. The plaque tack 5 and installation procedure may be designed in a number of ways that share a common methodology of utilizing the outward force of a spring-like annular band to enable the tack to be compressed, folded, or plied to take up a small-diameter volume so that it can be moved into position in the blood vessel on a sheath or catheter, then released, unfolded or unplied to an expanded state within the blood vessel.

The plaque tack device can be delivered into the blood vessel from endovascular insertion. SECTION IV below discusses a variety of delivery methodologies and devices that can be used to deploy plaque tacks. The delivery device for the different embodiments can be the same, or can be different with features specifically designed to deliver the specific tack. The plaque tack and installation procedure may be designed in a number of ways that share a common methodology of utilizing an expansion force of the delivery mechanism (such as balloon expansion) and/or the expansion force of a compressible annular band to enable the tack to be moved into position in the blood vessel, then released, unfolded or unplied to an expanded state within the blood vessel.

II. Further Embodiments of Endoluminal Staples

Variations of the plaque tack 5 can have a mesh-like configuration and can be arranged with one or more circumferential members formed with discrete struts, such as in open and closed cell constructions, among other designs.

A. Plaque Tack with Metallic Mesh Construction

Figure 3A:
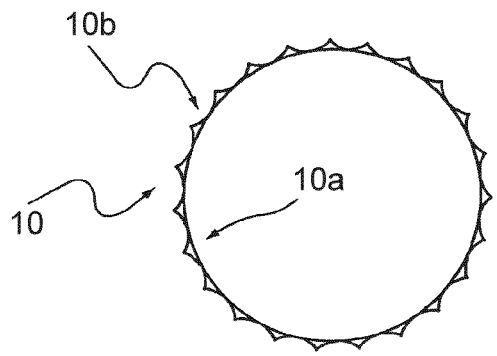
FIG. 3A shows an embodiment of a plaque tack in end view.
Figure 3B:
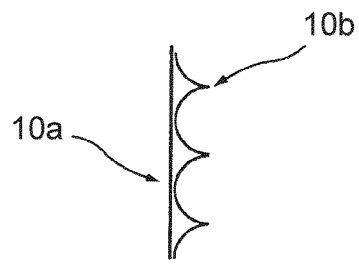
FIG. 3B shows it in side view.
Figure 3C:
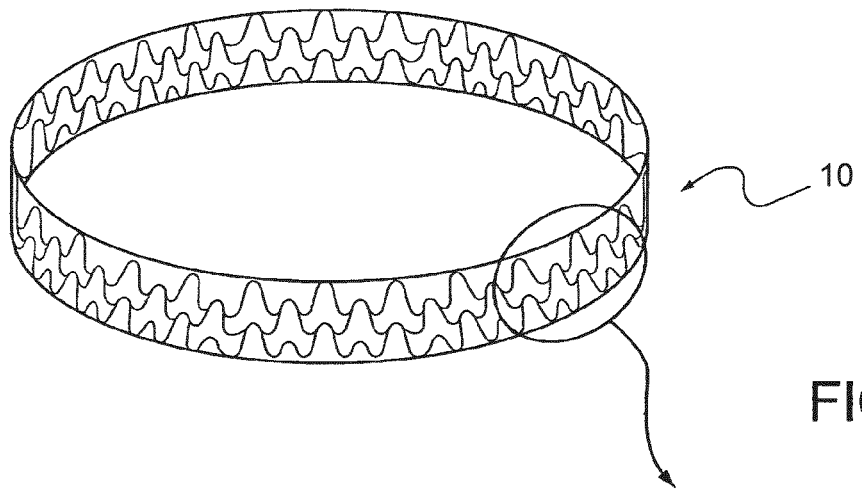
FIG. 3C shows the plaque tack in perspective.
Figure 3D:
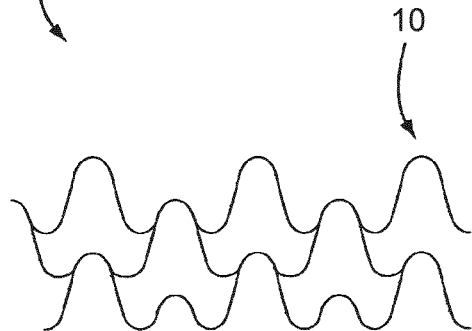
FIG. 3D shows a section of the plaque tack in a flat or rolled-out view.

An embodiment of a plaque tack 10 in the form of a metallic mesh construction is illustrated in FIGS. 3A-D, and 4. The plaque tack 10 is shown having a closed cell construction with an annular band 10a formed of interleaved mesh, and radially outwardly extending projections 10b. The plaque tack 10 may be laser cut or etched out of a metal tube form or made of thin metal wire which is looped and interleaved in a mesh that is welded, soldered, looped and/or linked together into the desired mesh shape as can be seen in FIGS. 3C-D. The projections 10b can project out from the annular band 10a. The projections 10b can be on an outer surface of the tack and can contact and/or embed into the wall of a blood vessel.

The annular band of the plaque tack 10 can have a dimension in the axial direction of the vessel walls (sometimes referred to herein as length) that is about equal to or less than its expanded diameter, in order to minimize the emplacement of foreign scaffolding structure in the blood vessel. Expanded diameter means final diameter in an unconstrained expansion. One or more tacks can be applied only in positions along the length of a plaque accumulation site where specific holding forces are needed to stabilize the site and/or hold pieces of plaque out of the way of blood flow.

The mesh pattern can be designed so that the plaque tack 10 can be compressed radially inward to a smaller-volume size. This can allow the plaque tack 10 to be loaded onto or within a catheter delivery device to be inserted into the blood vessel. For example, the tack 10 can have an overall circular shape with bends, such as inner V bends, that allow it to be folded in zig-zag fashion to a compressed smaller-volume form for loading in a delivery catheter, such as a deployment tube.

At the desired position in the blood vessel, the compressed plaque tack 10 is released from the delivery catheter. The mesh combined with an annular, ring shape can allow the plaque tack 10 to spring back to its expanded shape. Alternatively, the tack 10 can be expanded by another device, such as by a balloon. FIG. 3C shows the plaque tack 10 at rest in its fully expanded state and FIG. 3D shows a detail of a section of the metallic mesh.

Figure 4:
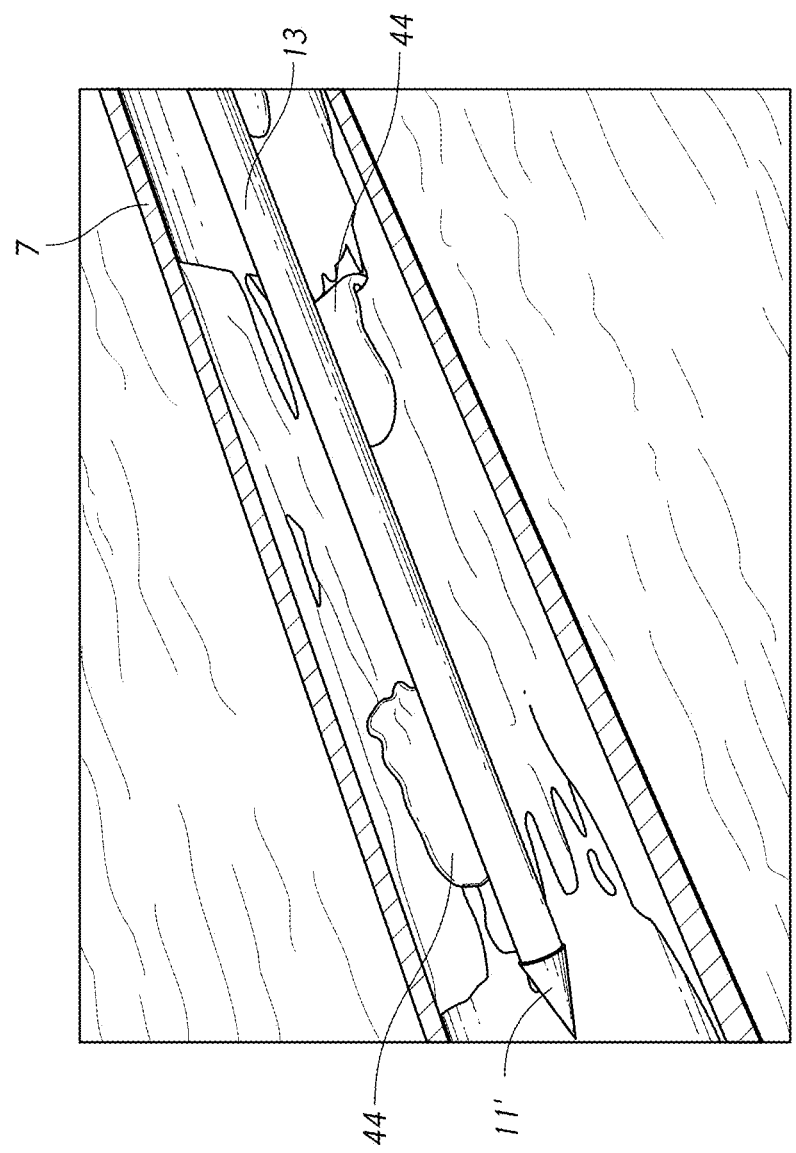
FIG. 4 is a schematic representation of a distal portion of a delivery device that has been advanced to a treatment site expanded in the blood vessel.
Figure 4A:
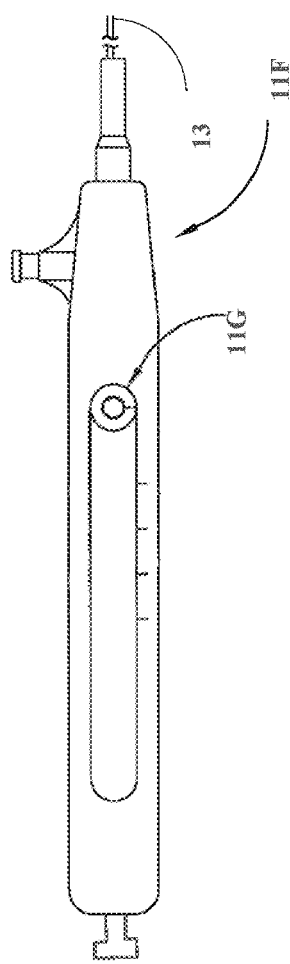
FIG. 4A illustrates the proximal end of one embodiment of a delivery device.
Figure 4B:
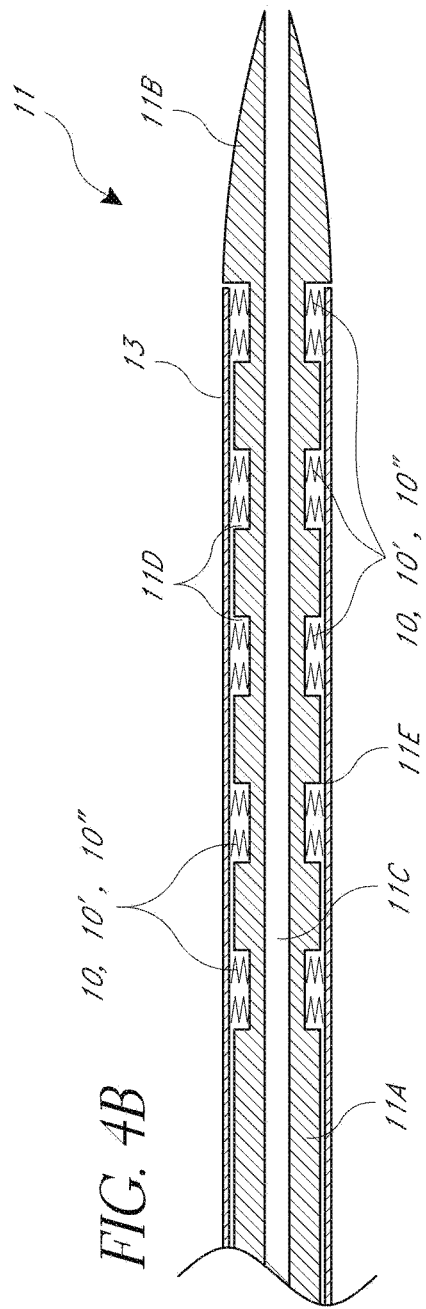
FIG. 4B is a plan view of the distal portion of the delivery device shown in FIG. 4.
Figure 4C:
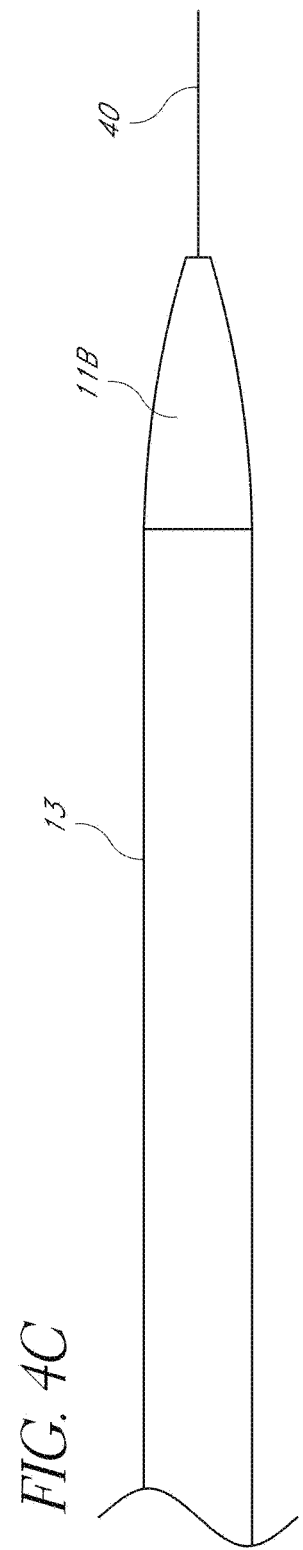
FIG. 4C is a cross-sectional view of the distal portion of FIG. 4B showing a plurality of tack devices prepared for implantation.
Figure 4D:
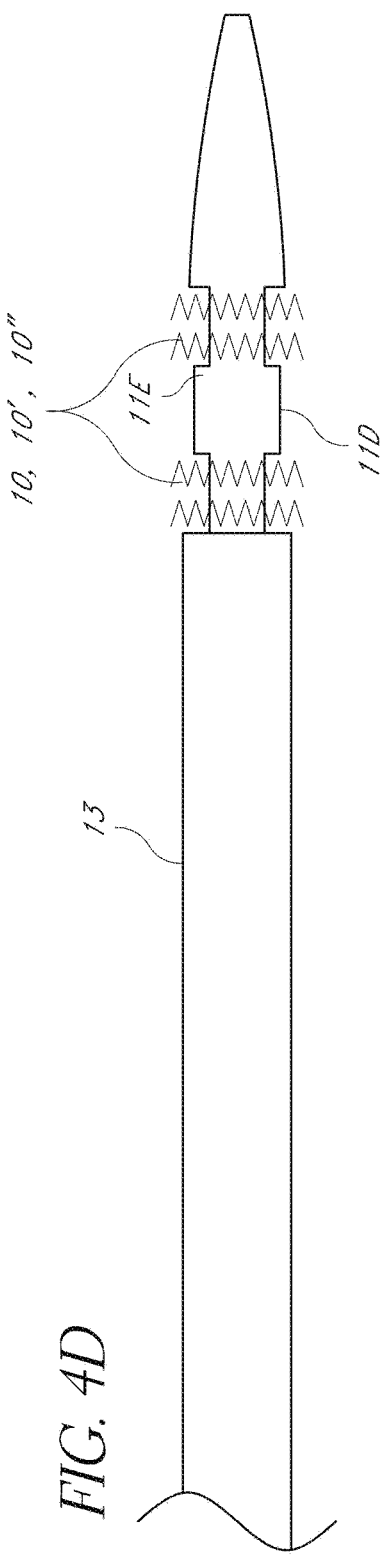
FIG. 4D shows the deployment of two tack devices upon retraction of a sheath.

FIGS. 4-4D show that one or more plaque tacks 10 can be positioned in a patient's vasculature at a treatment site by a delivery device 11 with an outer sheath 13 and thereafter expanded. The tack 10 can be expanded in any suitable way, such as by being configured to self-expand or to be balloon expanded. In the illustrated embodiment, a plurality of self-expanding tacks 10 (or variants, such as tack 10' or tack 10") is disposed inside the sheath 13. The delivery device 11 includes an elongate body 11A that is disposed at least partially within the sheath 13. The delivery device 11 also includes a dilating structure 11B that atraumatically displaces tissue and helps to guide the delivery device 11 through the vasculature. The body 11A can be configured with a lumen 11C extending therethrough for receipt and slideable advancement of a guidewire 40 therein. In the illustrated embodiment, the sheath 13 and the dilating structure 11B meet to provide a smooth outer surface to the delivery device 11, e.g. having the same outside diameter where they meet. The body 11A can be configured with a plurality of annular recesses 11D in which tacks 10, 10', 10" can be disposed. The annular recesses 11D can be defined between one or more shoulders 11E that prevent proximal or distal slippage of the tacks along the elongate body 11A. The recesses 11D could be eliminated by providing another structure for axially fixing the tacks 10, 10', 10" along the elongate body 10A.

FIGS. 4A and 4D show a proximal end of the device 11 and a manner of deploying the tacks 10, 10', 10". In particular, the proximal end of the device 11 includes a handle 11F and an actuator 11G. The actuator 11G is coupled with a proximal end of the sheath 13 such that proximal and distal movement of the actuator 11G cause proximal and distal movement of the sheath 13. FIG. 4A illustrates a distal positioning of the actuator 11G which corresponds to a forward position of the sheath 13 relative to the elongate body 11A and the recesses 11D. In this position the recesses 11D and the tacks 10, 10', 10" are covered by the sheath. Movement of the actuator 11G proximally relative to the handle 11F causes the sheath 13 to move proximally, e.g., to the position of FIG. 4D. In this position, the distal most two tacks 10, 10', 10" are uncovered and are permitted to self-expand in the manner discussed herein.

Returning now to FIGS. 3A-B, the projections 10b on the surface of the tack 10 can act as anchors or elevating elements to embed into or press against the plaque. An array of anchors or elevating elements can be used for linking the annular band of the tack with the plaque mass or blood vessel wall. The projections 10b can be made of a sufficiently rigid material to sustain a locking or engaging relationship with the blood vessel tissue and/or to pierce or engage the plaque and maintain the locking or engaging relationship therewith. The projections 10b may project at an angle of 90 degrees to the tangent of the annular band, or an acute angle may also be used.

The plaque tack may be made of a material such as a corrosion-resistant metal, polymer, composite or other durable, flexible material. A preferred material is a metal having "shape memory" (such as Nitinol). In some embodiments, a tack may have an axial length of about 0.1 to 6 mm, an expanded diameter of about 1 to 10 mm, and an anchor height from 0.01 to 5 mm. In general, the annular band of the plaque tack has a length in the axial direction of the vessel walls that is about equal to or less than its diameter, in order to minimize the amount of foreign structure to be emplaced in the blood vessel. The annular band can have a ratio of axial length to diameter as low as 1/100.

B. Plaque Tack with Open Cell Construction

Figure 5A:
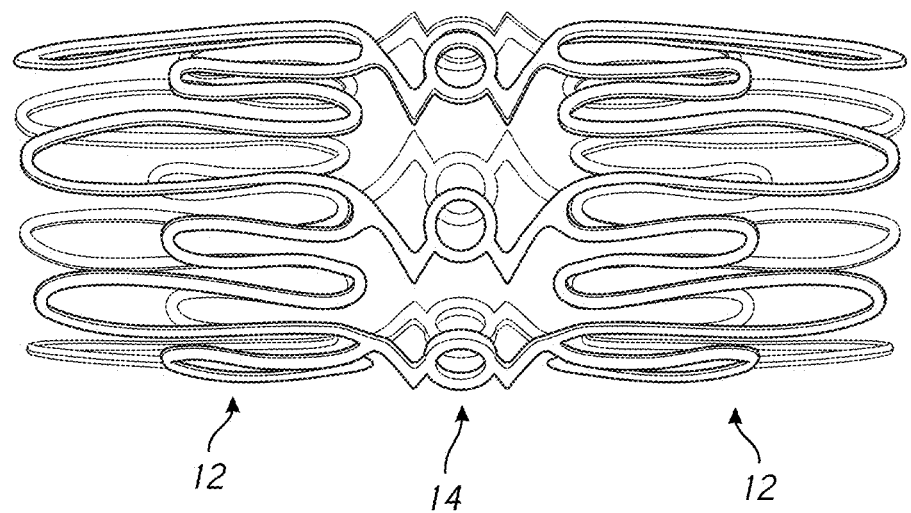
FIGS. 5A and 5B show another embodiment of a plaque tack in a collapsed state and in an expanded state, respectively.
Figure 5B:
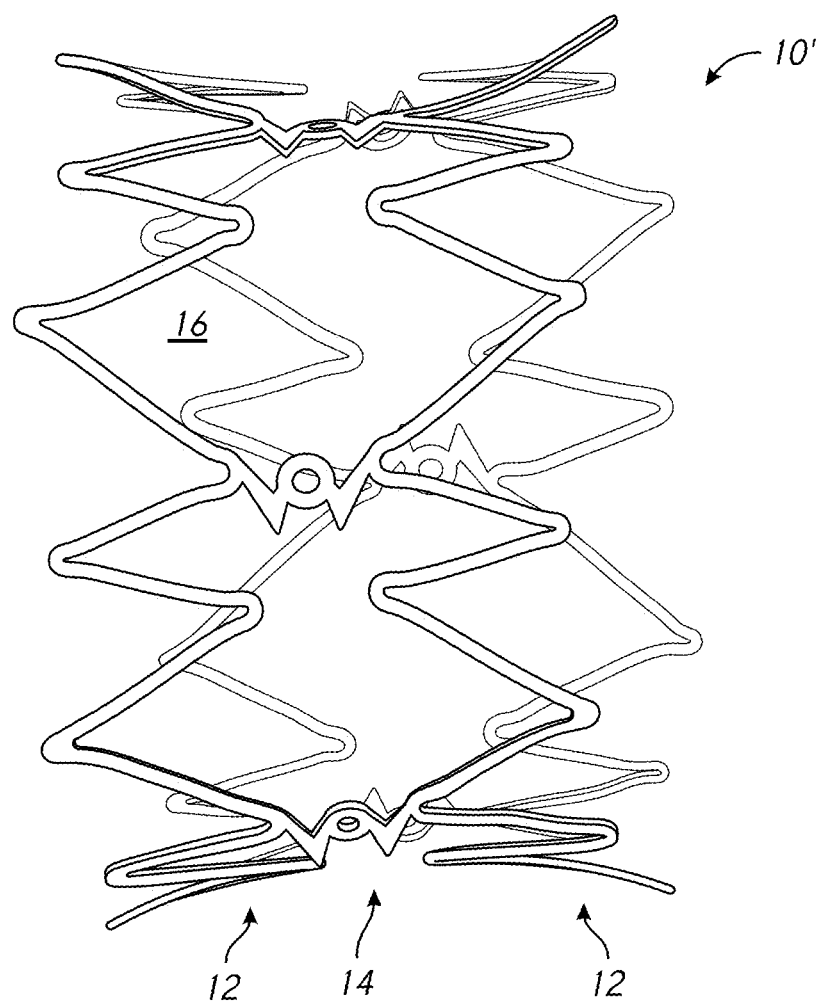
Figure 5C:
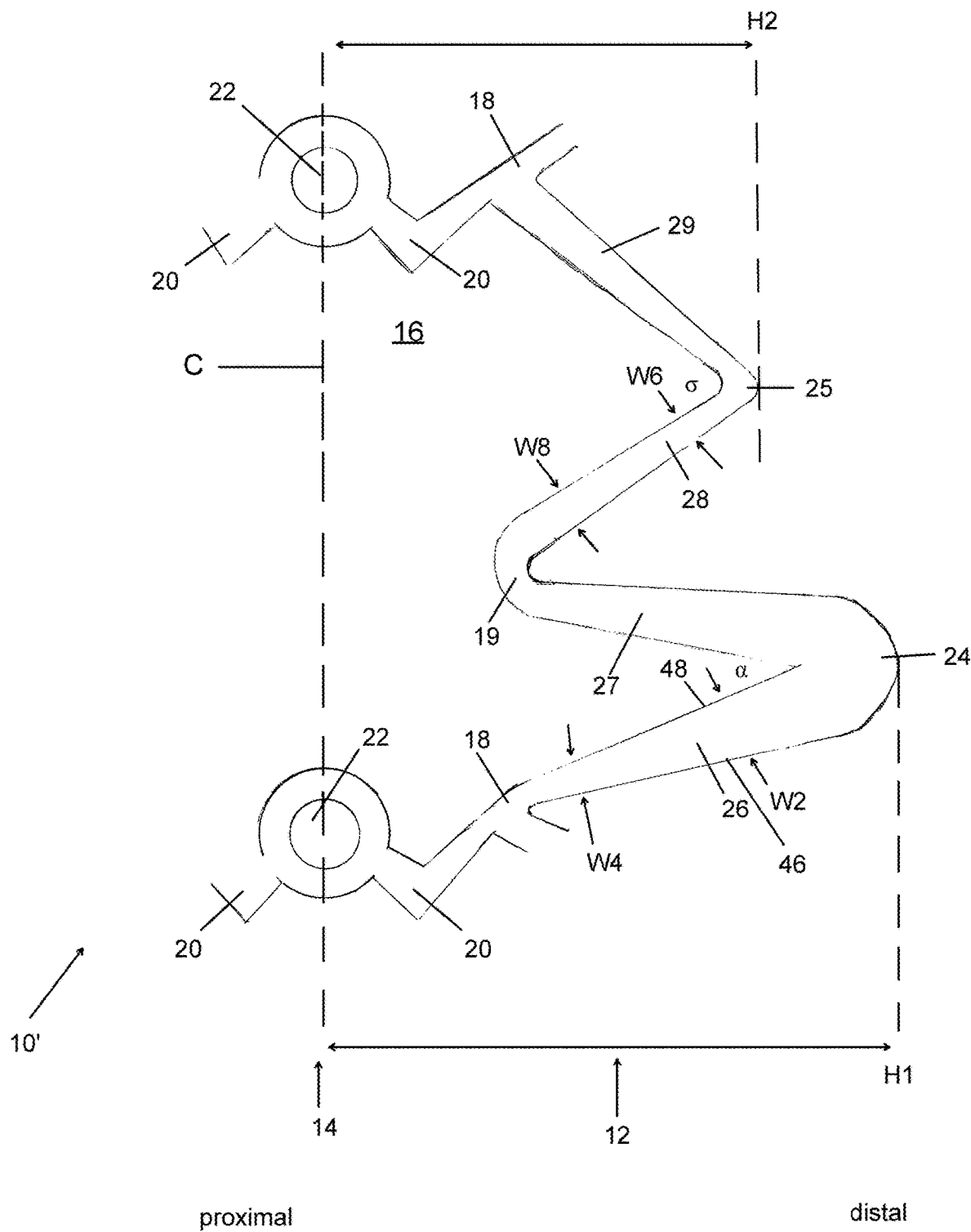
FIG. 5C shows a detail view of a section of the plaque tack of FIG. 5A-B.

FIGS. 5A-5C illustrate that in certain embodiments, a plaque tack 10' can be configured with an open cell structure. The plaque tack 10' can include one or more circumferential members that have undulating, e.g. sinusoidal, configurations and that are spaced apart in the axial direction. The circumferential members can be coupled together at one or more circumferentially spaced locations by axially extending members, sometimes referred to herein as bridge members. These embodiments are expandable over a wide range of diameters and, as discussed below, can be deployed in a variety of different vessels.

The plaque tack 10' can have features similar to those described above with respect to the plaque tack 10. For example, the plaque tack 10' may also be laser cut or etched out of a metal tube form. Similarly, the plaque tack 10' may be made of a material such as a corrosion-resistant metal (e.g., certain coated or uncoated stainless steel or cobalt-chromium alloys), polymer, composite or other durable, flexible material. A preferred material is a metal having "shape memory" (such as Nitinol).

FIGS. 5A-B show the overall structure of the plaque tack 10' with an open cell arrangement. The plaque tack 10' is shown having two circumferential members 12, which can be rings formed by a plurality of zig-zag struts, joined by bridges 14 that extend between the rings 12. The rings and bridges define a column of bounded cells 16 along an outer surface of the tack. The outer surface extends about an outer periphery, e.g., an outer circumference of the tack 10'. The boundary of each of the cells 16 is made up of a number of members or struts. As shown, the second ring is a mirror image of the first ring, though the first and second rings may be circumferential members with different configurations. Also, the bridges 14 can be symmetrical across a transverse plane extending through the axial mid-point thereof, though other configurations are also possible. The rings 12 can be considered coaxial, where that term is defined broadly to include two spaced apart rings, or structures, having centers of rotation or mass that are disposed along a common axis, e.g., the central longitudinal axis of the tack 10'.

FIG. 5C is a schematic flat depiction of a portion of a tack 10' illustrating a portion of the cell 16 and a portion of a boundary thereof. The portion illustrated to the right of the midline C is one half of the cell 16 in one embodiment. The other half can be a mirror image, as shown in FIGS. 5A-B, an inverted mirror image, or some other configuration. The portion of the ring 12 that is part of an individual cell 16 can define a portion that is repeated in a pattern along the ring. In some embodiments, the ring 12 can have portions that are repeated in a pattern that extends across cells, such as across 1.5 cells, 2 cells, 3, cells, etc. The pattern of the rings 12 combined with other features of the tack 10' can enable it to be circumferentially compressible. The difference between the compressed and expanded states can be seen by comparing the compressed view shown in FIG. 5A and the expanded view shown in FIG. 5B.

The cells 16 of the tack 10' can be bounded by portions of two rings 12, which can be mirror images of each other. Thus, some embodiments can be fully described by reference to only one side of the tack 10' and of the cell 16. The ring 12, a portion of which is illustrated in FIG. 5C, has an undulating sinusoidal pattern. The undulating pattern can have one or more amplitudes, such as the dual amplitude configuration shown.

The rings 12 can have a plurality of struts or structural members 26, 27, 28, 29. The plurality of struts can repeat about the circumference of the ring 12. The struts can be many different shapes and sizes. The struts can extend in various different configurations. In some embodiments, the plurality of struts 26, 27, 28, 29 extend between inward 18, 19 and outward apices 24, 25.

In some embodiments, the outward apices 24, 25 extend axially different distances as measured from a central zone or midline C of the tack 10'. In particular, the apex 24 can be considered a high apex and the apex 25 can be considered a low apex in this regard. The inward apices 18, 19 may be axially aligned, e.g., being positioned at the same axial distance from the midline C. Thus, the outward apex 24 is disposed farther away from the bridge and inward apices than the outward apex 25. In some embodiments, the axial length of the tack 10' is measured from the top of the outward apex 24 on one side of the cell 16 to the corresponding top of the outward apex 24 on the other side of the cell. Put another way, the first outward apex 24 extends a first axial distance from the midline C of the tack 10' and the second outward apex 25 extends a second axial distance from the central zone C of the tack 10', the first distance being greater than the second distance. Each side of the cell 16 as shown has one high outward apex 24 and one low outward apex 25.

The bridge 14 can be connected to the one or more of the inward apices 18, 19. The bridge 14 can join the two rings 12 together. The bridge 14 can have many different shapes and configurations. Some embodiments of the tack 10' have a proximal ring and a distal ring with the bridge disposed between and connecting them. As mentioned above, the bridge 14 can be located at the central zone or midline C of the tack 10'. In FIG. 5C, the word "proximal" refers to a location on the tack 10' that would be closest to vascular access site than the portion labeled "distal". However, the tack 10' can also be thought of as having a medial portion that corresponds to the midline C and lateral portions extending in both directions therefrom. As such, the location labeled "proximal" is also a medial location and the location labeled "distal" is also a lateral position. All of these terms may be used herein.

As shown, the bridge 14 is connected to each ring at the inward apex 18. In some embodiments, a bridge is connected to every inward apex, forming a closed cell construction. In other embodiments, the bridge 14 is connected to every other inward apex, every third inward apex, or spaced farther apart by as needed, forming a variety of open cell configurations. The number of bridges 14 can be chosen depending upon the application. For example, six or fewer bridges 14 may be used between the two rings 12 when desired for limiting neointimal hyperplasia.

One technique for enhancing the plaque holding capability of the bridges 14 is to align plaque holding structures (such as the barb 9, projections 10b, or the anchors discussed below) with a force application location or direction of the ring 12. In some embodiments, at least a portion of the bridge 14 can be aligned, with one of the struts of the ring 12. For example, where the bridge 14 connects to the ring 12, whether at an inward apex or at a strut, that connecting portion of the bridge can extend therefrom in a manner that is aligned, partially or substantially aligned with a strut. FIG. 5C shows that the bridge 14 is connected to the inward apex 18 and that the connecting portion of the bridge is substantially aligned with the strut 26. In one technique, a plaque holding structure of the bridge 14 is disposed on a projection of a longitudinal axis $L_A$ of the strut 26. As discussed below, the tack 10' has a plurality of anchors 20. The axis $L_A$ intersects a portion of an anchor 20 to maximize a torque effect from the expanded strut 26 to the anchor 20. In the arrangement of FIG. 5C, an anchor on an opposite side of the centerline C is disposed on the projection of the axis $L_A$ and the projection of a longitudinal axis $L_A$ of a mirror image strut 26 intersects the anchor 20 of the strut on the same side of the centerline C as the strut 26 shown in FIG. 5C. In another technique, the projection of the strut 26 and its mirror image strut can be aligned with the centerline C, which is rigidly coupled with the anchors 20. The bridge 14 also is aligned with a high amplitude sinusoidal section of the tack 10'.

A series of unique design features can be integrated into the tack 10' for various purposes as will be discussed in more detail in the sections below. For example, the tack 10' can include one or more of anchors, markers and focal elevating elements, among other features. As discussed above, FIG. 5C shows that the plaque tack 10' can include a plurality of (e.g., two) anchors 20. The tack 10' also can include a position marker 22 on each bridge 14. The position markers 22 can be fluoroscopically opaque and in one arrangement are generally flat. As used in this context, flat markers are arranged to have a planar outer face that is tangential to a cylinder that extends through an outer surface of the tack 10' or that is concentric with the outer surface but disposed radially inside the outer surface. The anchors 20 can similarly be configured to be tangential to a cylinder that extends through an outer surface of the tack 10'.

As another example, a series of unique design features can be integrated into the tack 10' for dynamic distribution of stresses within the tack 10'. These design features can enable the uniform control of the tack 10' during compression, expansion, delivery, and catheter release. The design features can also individually and/or collectively manage the stresses throughout the bulk of the tack, along the struts, and at the interface of the tack and the blood vessel lumen. Better control of the distribution of stresses within the tack has the benefit of reducing cellular response and tack fracture by limiting strut fatigue and the associated micro-rubbing at the tack-blood vessel interface. Micro-rubbing includes a variety of small scale adverse interactions between implants and patient tissue, such as abrasion or friction that occurs on a cellular or intercellular level between the tack and the blood vessel lumen.

A reduction in cellular response is believed to be achieved partly through a reduction of surface area contact between the tack and the blood vessel lumen and partly by maximizing alignment of the contact points or structures with the blood vessel cells' natural orientation. Thus, the tack is able to move with the blood vessel while decreasing the micro-rubbing. Other devices, such as stents, contact the blood vessel cells in ways that may extend across, e.g., transversely to, multiple cells increasing micro rubbing at the stent-blood vessel interface.

1. Single Column Cell Design

One characteristic of the embodiment the tack 10' of FIGS. 5A-C is that it includes a single column open cell design contained between two zig-zag rings. This arrangement provides minimal (if any) scaffolding of a vessel. In one sense, a ratio of the vessel contact area to the total treatment zone of the plaque tack 10' is small. In this context, vessel contact area is the sum of the area of outer portions of the tack 10' that may come into contact with the vessel wall. More particularly, the vessel contact area may be calculated as a summation for all of the struts of the length of each strut times the average transverse dimension (width) of the radially outer surface of each strut. If the struts of the zig-zag rings are laser cut, the width of the radially outer surface of the strut may be less than that of the radially inner surface. The vessel contact area may also include the radially outer surface of the bridges 14. The total treatment zone of the plaque tack 10' can be defined with respect to the fully expanded configuration in a best fit cylinder. A best fit cylinder is one that has an inner circumference that equal to the unconstrained circumference of the plaque tack 10'. The total treatment zone has an area that is defined between the proximal and distal ends (or the lateral edges) of the plaque tack 10'. The total treatment zone can be calculated as the length between the proximal and distal ends (or lateral edges) in the best fit cylinder times the inner circumference of the best fit cylinder. In the illustrated embodiment, the length for purposes of determining the total footprint can be the distance at the same circumferential position between high outward apices of the rings 12.

In various embodiments, the ratio of the vessel contact area to total treatment zone is less than 50%. In some embodiments, the ratio of the vessel contact area to total treatment zone is even less, e.g., 40% or less. The ratio of the vessel contact area to total treatment zone can be as small as 20% or less. In specific examples, the ratio of the vessel contact area to total treatment zone is 5% or even 2% or less. As discussed below, focal elevating elements can augment this advantageous feature, even further lowering the ratio of the vessel contact area to total treatment zone by providing separation between the vessel wall and at least a portion the circumferential members 12.

In certain methods, a vessel can be treated by implanting a plurality of structures, e.g., plaque tack 10'. The structures have a total contact area with the vessel wall. The total contact area may be the sum of the vessel contact area of the individual structures. In the method, a total treatment zone area can be defined as the surface area between the proximal end of the most proximal structure and the distal end of the distal most structure. In one method, the total contact area is no more than about 55% of the total treatment zone area. More typically, the total contact area is between about 10% and about 30% of the total treatment zone area. In specific examples, the total contact area is no more than 5-10% of the total treatment zone area.

The tack 10' can also be understood to provide a relatively high open area within its lateral edges compared to stents. Distinct from traditional stents, the track 10' need not include sufficient metal to provide a scaffolding function, to hold a vessel open. To accomplish many of the contemplated treatments, the tack 10' can be configured to limit its contact to only a single point or a plurality of discrete points, for example at one or more axial locations. The discrete points can be widely spaced apart, such as by being points on a circumference that are separated by spaces or, when applied, vascular tissue.

In some embodiments, the open area bounded by lateral edges of the tack 10' dominates the total footprint, as defined above. The open area of the tack 10' can be defined as the sum of the areas of the cells 16 when the tack 10' is in the fully expanded configuration, as defined above. The open area should be calculated at the outer circumference of the tack 10', for example the area extending between the internal lateral edges of each of the struts. In this context, internal lateral edges are those that form at least a part of the boundary of the cells 16. In various embodiments, the sum of the radially outwardly facing surface of the struts of the tack 10' can be no more than about 25% of the open area of the tack 10'. More typically, the sum of the radially outwardly facing surface of the struts of the tack 10' is between about 10% to about 20% of the open area of the tack 10'. In other examples, the sum of the radially outwardly facing surface of the struts of the tack 10' is less than about 2% of the open area of the tack 10'.

A single column design includes arrangements in a plurality of tack cells are oriented circumferentially about a central axis of the tack 10'. Tack cells can come in many configurations, but generally include spaces enclosed by struts and are disposed in the wall surface of the tack. Open cell designs include arrangements in which at least some of a plurality of internally disposed struts of proximal and distal circumferential members are not connected by bridges or axial connectors. FIG. 5C shows that the inward apex 19 is unconnected to a corresponding inward apex on a mirror image ring 12. Thus, a portion of the cell 16 disposed above the inward apex 19 in FIG. 5C is open to another portion of the cell 16 disposed below the inward apex 19. Open cell designs have increased flexibility and expandability compared to closed cell designs, in which each internally disposed struts of a proximal circumferential member is connected to a corresponding internally disposed struts of an adjacent circumferential member. The cell 16 would be divided into two closed cells by connecting the inward apex 19 to a corresponding inward apex on the mirror image ring 12. As discussed above, closed cell plaque tacks can be suitable for certain indications and can include other features described herein. As shown, the single column open cell design extends along the midline C of the bridge (and also, in this embodiment, along the circumference of the tack 10').

In one embodiment the cell 16 is identical to a plurality of additional cells 16 that would be disposed circumferentially about the central axis of the tack 10'. The number of cells can vary depending on factors such as the size of the vessel(s) for which the tack 10' is configured, the preferred arrangements of the rings 12, the number of bridges 14 to be provided and other factors.

As discussed above, the tack 10' can include proximal and distal rings 12 connected by bridges 14. The proximal ring 12 can be disposed at a proximal end of the tack 10'. The distal ring can be disposed at a distal end of the tack 10'. In some embodiments, the distal ring is the distal most aspect of the tack 10' and the proximal circumferential member is the proximal most aspect of the tack 10'. The bridges 14 can divide an outer surface of the tack 10' into cells 16 bounded by the bridges 14 and a portion of each of the proximal and distal rings 12. In the embodiment of FIGS. 5A-5C, the single column design is provided by providing bridges at only one axial position and only a pair of circumferential members or rings 12. FIG. 5C includes the terms "distal" and "proximal" for reference purposes related to this and other examples, thus the ring 12 shown is the distal ring. In other embodiments, the ring 12 shown can be the proximal ring.

As discussed above, the cells 16 can have one of many different shapes and configurations. FIG. 5B shows that, the cells 16 are aligned as a repeating pattern forming a single column open cell design along the circumference of the tack 10'.

Conventional stent designs are generally relatively long (e.g., 4 cm and even up to 20 cm when used in peripheral vasculature) from their distal to proximal ends. Where arranged with circumferentially disposed cells, conventional stents have a large number of columns of cells. These designs are burdened with repeating points of weakness and can generate stresses that become difficult to manage. As the device is put under stress and strain, these conventional stents must find regions of greater pliability within the strut matrix. These strut regions absorb the load throughout the system and under periods of repeated external forces begin to fail, such as through metallurgical friction loading.

The single column configuration of the tack 10' is not subject to repeated weak point loading due to movement of remote stent portions because the tack does not have to be axially elongated to provide effective tacking treatment. Other benefits that derive from the shortness include reduced friction at the interface with the catheter sheath during delivery and with the blood vessel wall. As discussed above, the stress at the blood vessel wall interface is reduced due to the lack of cell-to-cell dragging or pulling which in turn reduces the potential that the tack will pull or drag adjacent cells increasing cellular inflammation or histological response along the lumen wall. A single column or other axial short configuration also reduces the stress along each strut because the overall length of single column or other axial short structures or configurations are less affected by the anatomical motion (e.g., bending, twisting, and rotating). This results, at least in part, from the anatomy shifting around short structures while longer structures do not allow the anatomy to shift and thus longer structures absorb more forces resulting from this anatomical motion.

Any motion between the surfaces of the tack and the blood vessel can cause rubbing and friction. If the motion is very small it can be described as micro-rubbing, as discussed above. Even micro-rubbing produces a negative effect on both the tack 10' and the biological cells of the blood vessel. For example, friction occurs when a portion of an implanted object moves while another portion is stationary or moving by a smaller amount. Differential amounts of moving over time weakens the material leading to fracture by processes such as work hardening. The biological cells become irritated by the friction and can respond by producing an inflammation response. Inflammation can drive a variety of undesired histological responses including neointimal hyperplasia and restenosis.

2. Controlled Angle of Struts

FIG. 5C shows that the tack 10' has two circumferential members or rings 12 which each have a plurality of internal angles, including α, and σ. A first angle α is defined at the first outward apex 24 between the struts 26, 27 and a second angle σ is defined at the second outward apex 25 between the struts 28, 29. In some embodiments, the first angle α can be greater than the second angle σ. For example, the first angle α can be between 43° and 53°, or between 45° and 51°. The second angle σ can be between 31° and 41°, or between 33° and 39°. In some embodiments, the first angle α can be about 48°, and the second angle σ can be about 36°.

In a preferred embodiment, the tack 10' has an expanded outer diameter of 7.5 mm and the first angle α can be 47.65° and the second angle σ can be 35.56°. In such an embodiment, the plaque tack 10' can be formed from a tube stock with an initial outer diameter 4 mm. The tube stock can be expanded to 7.5 mm and then heat treated in that shape. In some embodiments, the plaque tack 10' can be made of a shape memory material and the heat treatment step can be to engrain that particular shape into the "memory" of the material. The plaque tack 10' can then be crimped or compressed and flash frozen in the compressed state to then be loaded onto a delivery device.

A beneficial feature of the tack 10' is that the angle of the struts as they meet at each apex can be controlled in at least one of an expanded and a contracted state. For example, the internal angles α, σ of the outward apices 24, 25 can be controlled to be within ±5% of a selected nominal value. This control can be achieved for example, in the expanded state during the heat treatment during the manufacture of the plaque tack 10'.

It has been found that control of the angles can beneficially offer relief from imperfections in the manufacturing process. In some cases, the control of other dimensions can be relaxed if these angles are sufficiently well controlled. By controlling these angles, production run quality can be improved. Such control has been found to enable repeatable, uniform, and balanced compressibility of the tack 10' during the crimping cycle of manufacturing. These factors increase production run repeatability and offer ease of volume manufacturing which results in a reduction in overall cost of the part.

In addition, control of the apex angles allows the plaque tack 10' to better distribute stresses along the circumferential members or rings 12. The control of apex angles can be used to control or distribute stresses within the ring 12, e.g., uniformly along the length of the struts or non-uniformly to a region that can more robustly respond to stress loading. By distributing stress along the strut, the problematic localized stresses on the tack 10', such as at vulnerable spots can be avoided during the expansion and crimping processes of manufacturing.

3. Inverse Tapering Struts

In some embodiments, such as that shown in FIGS. 5A-C, the width of one or more of the struts 26, 27, 28, 29 of the tack 10' can be different at different locations, e.g., can vary along the struts. For example, the struts can be tapered along their length. The taper can be the same or different along each strut or along each type of strut. For example, each circumferential member or ring 12 can be made up of a pattern of repeating struts, with each type of strut having a particular taper.

FIG. 5C shows that the ring 12 has a first strut coupled with a bridge 14 that is tapered such that a portion of the strut closer to the midline C (sometimes referred to herein as a medial portion or location) is narrower than a portion of the strut spaced farther away from the midline C (sometimes referred to herein as a lateral portion). A second strut is connected to the first strut at lateral ends of the first and second struts. The second strut can have the same or a different taper. For example, the second strut can also have a medial portion narrower than a lateral portion of the second strut. In addition, the second strut can be narrower overall than the first strut. A third strut can be connected to the second strut at medial ends of the second and third struts. The third strut can have a medial portion that is wider than a lateral portion thereof. A fourth strut can be connected to the third strut at lateral ends of the third and fourth struts. The fourth strut can have a medial portion that is wider than a lateral portion thereof. The fourth strut can have the same or a different taper from the third strut. For example, the fourth strut can wider overall than the third strut.

FIG. 5C schematically illustrates the differences in the widths of the struts in one embodiment. In some embodiments, the long struts 26 and the long strut 27 have the same width at the same axial position and the short struts 28 and the short strut 29 have the same width at the same axial position. The struts 26 and the strut 27 can have the same shape. The strut 28 and the strut 29 have the same shape in some embodiments. The shape of the struts 26, 27 can be different form the shape of the struts 28, 29. In some embodiments, the long strut 26 and the long strut 27 have different widths at the same axial position and the short strut 28 and the short strut 29 also have different widths at the same axial position.

In a preferred embodiment, the long struts 26, 27 are disposed at a first circumferential location of the tack 10' adjacent to one of the markers 22. In particular, the strut 26 has a medial end connected to or forming a portion of one of the inward apices 18 and a lateral end disposed away from the inward apex 18. The lateral end is coupled to the strut 27 at or adjacent to the outward apex 24. The strut 26 has a width W4 adjacent to the medial end and a width W2 adjacent to the lateral end. In this embodiment, the width of the strut 26 increases along the length thereof from the width W4 to the width W2. The increase in width along the strut 26 preferably is continuous along this length.

Also, the sides of the struts 26 can be sloped relative to a longitudinal axis $L_A$ of the strut 26. For example, a first side 48 disposed between the longitudinal axis of the strut 26 and the strut 27 can be disposed at an angle to (e.g., non-parallel to) the longitudinal axis of the strut 26. In another embodiment, a second side 46 of the strut 26 can be disposed at an angle to (e.g., non-parallel to) the longitudinal axis of the strut 26. In one embodiment, both the first and second sides 46, 48 of the strut can be disposed at angles to the longitudinal axis of the strut 26.

The strut 27 preferably also has different widths at different points along its length. In particular, the strut 27 can be wider in a generally lateral direction adjacent to the outward apex 24 than it is adjacent to the inward apex 19. As discussed above in connection with the strut 26, the strut 27 can have side surfaces that are angled relative to the longitudinal axis of the strut 27. The strut 27 can be tapered between its ends, e.g., having a continuously decreasing width along its length from wider adjacent to the outward apex 24 to narrower adjacent to the inward apex 19.

The strut 28 extends from the strut 27 or inward apex 19. The strut 28 can have a medial end that is wider than a lateral end of the strut 28 and can have different widths at different points along its length. The side surfaces can also be angled relative to the longitudinal axis of the strut 28.

Finally, a strut 29 can be connected to the strut 28 or outward apex 25 at a lateral end of the strut 29. The strut 29 can have a medial end that is wider than the lateral end thereof. The strut 29 can have a taper that is the same or different from the strut 28. For example, the strut 29 can be wider overall than the third strut.

In one embodiment, the strut 26 can have a width $W_2$ of about 0.12 mm at the lateral end near the outward apex 24 and a width $W_4$ of about 0.095 mm at the medial end near the inward apex 18 and the strut 28 can have a width $W_6$ of about 0.082 mm near the outward apex 25 and a width $W_8$ of about 0.092 mm near the inward apex 19. More generally, the change in thickness between W4/W2 expressed as a percentage can be between about 70% and about 90% more typically between about 75% and about 85%, and in certain embodiments about 80%. The tapering can also be inverted, e.g., with the struts tapered from the ends (e.g., lateral edges) toward the medial portion.

Figure 5D:
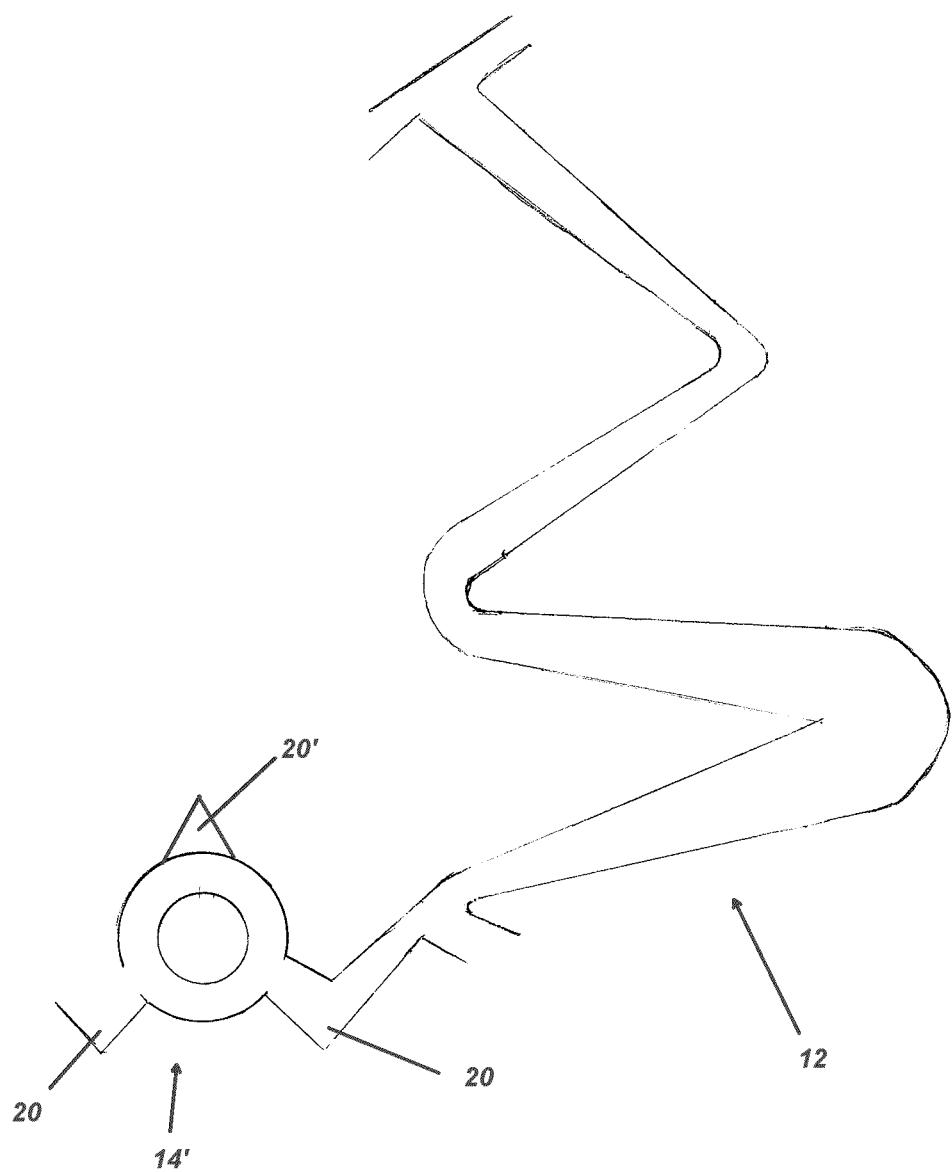
FIG. 5D shows a variation on the embodiment of FIGS. 5A-5C having an anchor disposed on a midline of the tack.
Figure 5E:
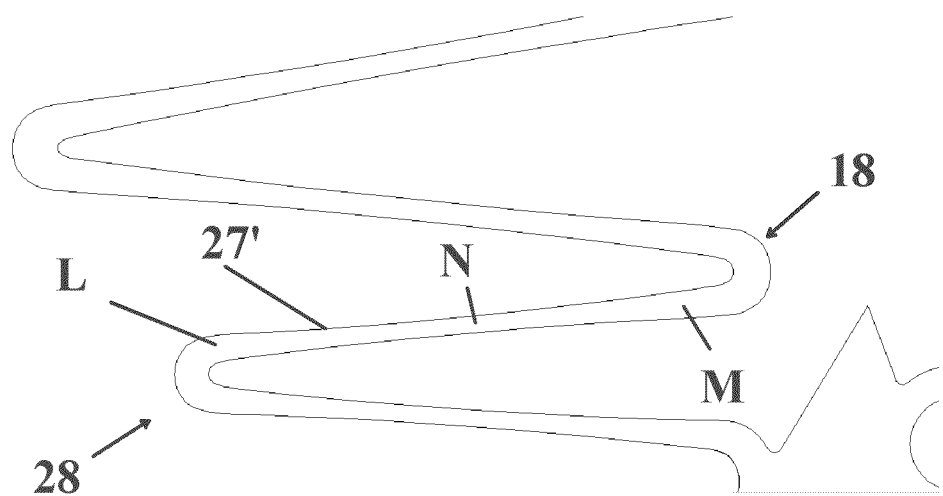
FIG. 5E shows a variation with struts that taper from wider at a lateral edge of a tack to narrower at a mid-section of the strut and/or from narrow at a mid-section of a strut to wider adjacent to a medial location of the tack.

FIG. 5E illustrates another variation in which the width of one or more of the struts of the tack can be different at different locations, e.g., can vary along the struts. For example, a strut 27' can be provided that is similar to the strut 27 except that the strut 27' is narrowest in a mid-section N. The strut 27' can have a lateral wide portion L adjacent to the outward apex 28 and a medial wide portion M adjacent to the inward apex 18. The width of the strut 27' reduces along the length thereof from the lateral wide portion L toward the medial portion M. In one embodiment, the strut 27' is continuously narrower along the length from the lateral end of the strut 27' toward the midline of the strut.

The strut 27' can be narrowed such that the ratio of width at the midline to width at the lateral end of the strut 27', expressed as a percentage, is between about 20% and about 85%. In some embodiments, this percentage is between about 35% and about 75%. The tapering can be such that this percentage is between about 55% and about 70%. From the medial wide portion, the strut 27' can be narrowed along the length thereof. In one embodiment, the strut 27' is continuously narrower along the length from the medial end of the strut 27' toward the midline of the strut. The strut 27' can be narrowed such that the ratio of width at the midline to width at the medial end of the strut 27', expressed as a percentage, is between about 20% and about 85%. In some embodiments, this percentage is between about 35% and about 75%. The tapering can be such that this percentage is between about 55% and about 70%. The embodiment of FIG. 5E provides a greater range for compression and expansion in smaller diameter configurations. Smaller diameter configurations can be used in smaller body lumens, e.g., blood vessels. For example, a tack with this configuration can be formed out of 2.3 mm diameter tubing, whereas the embodiments of FIG. 5C are optimally formed out of 4.5 mm diameter tubing. The configuration of FIG. 5E can be used to make tacks that are suitable for a 4 French delivery device. Tacks configured as in FIG. 5E can have an unconstrained expanded size of between about 4.5 mm and about 6.5 mm. In some embodiments, devices including the configuration of FIG. 5E can have an unconstrained expanded size of between about 5 mm and about 6 mm, e.g., between about 5.5 and about 6.0 mm. One embodiment expands to about 5.7 mm when unconstrained.

A unique inverse taper or variation in width along the strut is achieved by inverting the orientation of the taper between the short struts 28, 29 and the long struts 26, 27. The longer struts 26, 27 go from a narrow width near the inward apices 18, 19 to a broader width near the high outward apex 24. Conversely, the shorter struts 28, 29 are the opposite with a broader width near the inward apices 18, 19 to a narrower width near the low outward apex 25.

Through strategic selection of the width of the struts, as discussed above, the plaque tack can distribute the stresses observed during compression and after deployment. This feature can also contribute to the control of the stress by distributing the region of stress more uniformly along the length of the strut. In some embodiments, it may be desirable to distribute the stress non-uniformly to regions more able to handle the stress.

4. Dual Amplitude Struts

As been discussed above, the ring 12 illustrated in FIGS. 5A-5C has an undulating sinusoidal pattern. The axial extent of the ring 12 can vary about the circumference of the ring 12, for example providing a plurality of amplitudes as measured by the distance from an inward apex to an adjacent outward apex. The undulating pattern can have one or more amplitudes, such as the dual amplitude configuration shown. In the dual amplitude configuration the plurality of struts 26, 27, 28, 29 extend between inward 18, 19 and outward apices 24, 25.

In some embodiments, the outward apices 24, 25 alternate between a high outward apex 24 and a low outward apex 25. In this context "high" corresponds to a larger distance H1 as measured from a central zone or midline C of the tack 10' and "low" corresponds to a smaller distance H2 as measured from the midline C (FIG. 5C).

The varying amplitude of the long and short sinusoidal struts described above can provide additional control of the plaque tack's functionality. In particular, it can enhance compression of the tack 10' to provide a greater change in circumference from the fully expanded configuration to a compressed configuration when crimped during manufacturing. Greater compressibility facilitates delivery in smaller vessels and a greater range of indication that can be treated because it enables a smaller crossing profile delivery system.

The height $H_1$, $H_2$ of the apices is measured from the center line C to the top of the respective outward apices 24, 25. The dual amplitude sinusoidal patterned plaque tack 10', such as that shown in FIGS. 5A-C, enables broad ranging conformable dimensions that can easily be scalable to different outer diameter designs. The open cell single column design allows broad range compression and expansion. This is partly due to the length of strut available for effective expansion. The ease of compression is associated with the position of the apices disposed $H_1$ and $H_2$ from the center of the tack, which permits these apices to compress at a different locations instead of at the same lateral location. If $H_1$ and $H_2$ of the apices are aligned (e.g., at the same axial location) they would press against each other during compression limiting the compression range.

The ranges of compression for the plaque tack 10' have been measured to 0.25 times nominal tube size in combination with ranges of expansion up to 2 times nominal tube size, although these are not the anticipated limits of the device. Combining these ranges the full range of compression has been measured at 0.125 times the heat treated outer diameter. As discussed above in SECTION II.B.2, in some embodiments the nominal tube size is 4.5 mm and the tube is expanded to 7.5 mm in the manufacturing process. According to some embodiments, the distance from the midline C of the device to the apex of the longer struts $H_1$ is approx. 3.0 mm, while the distance $H_2$ to the apex of the shorter struts is approx. 2.6 mm.

In addition to the enhanced compressibility range, the energy stored in the shorter amplitude struts offers additional control of the plaque tack 10' during the release phase of delivery within the blood vessel. As the catheter sheath is retracted, the longer struts are uncovered first followed by the shorter struts (FIG. 5C). This mismatch provides greater retention forces to maintain the plaque tack 10' in the delivery catheter and thus provides greater control of the plaque tack during delivery.

5. Centrally Disposed Anchoring and Elevating Structure

FIGS. 5A-5C illustrate that the plaque tack 10' can include centrally disposed anchors 20. While the anchors 20 are primarily for securing loose plaque, as discussed above, their placement and configuration enhance the control of the deployment and the performance of the tack 10' once placed inside the blood vessel.

As discussed above, the plaque tack 10' can be a self-expanding circumferential structure and the anchors 20 can be disposed on an outer portion of the tack. The anchors 20 can be coupled with any portion of the tack 10' but preferably are disposed adjacent to the midline C of the bridges 14 as discussed above. In one embodiment, the tack 10' includes two anchors disposed on either side of the midline C as illustrated in FIG. 5C. In another embodiment, a single anchor can be provided on the midline C. In a further embodiment, at least three anchors 20 can be provided, such as one on the midline and two on either side thereof as illustrated in FIG. 5C. The bridge 14 can have two anchors on one side and one anchor on the other side connecting the two other anchors, as shown in FIG. 5D. In FIG. 5D, an anchor 20' is located at the center of the tack 10' along its axial direction. This embodiment provides at least one anchor 20' that is located on both sides of the midline C.

Also, the anchor 20' can be located on an opposite side of the marker 22 from the anchors 20. As such, plaque can be anchored from a plurality of directions, e.g., a plurality of circumferential directions. In a further embodiment, the anchors 20 are not present and a single anchor 20' located on the midline C is provided. The embodiment illustrated in FIGS. 5A-C could also be modified to include one or more anchors on either side of the marker 22, where anchors are currently only shown on one side.

In one aspect, the plaque interaction of the tack 10' is primarily provided by the anchors 20 and to a lesser extent the bridges 14. In some embodiments, the anchors can have a preferred penetration length into the plaque of 0.01 mm to 5 mm. In certain variations, the penetration length is within a range of about 0.03 mm to about 1 mm. In other variations, the penetration length is within a range of about 0.05 mm to about 0.5 mm. The bridges 14, which can be disposed at alternating inward apices, as discussed above, can be configured to reside on a tangential plane of a cylinder when the tack 10' is fully expanded and not being deformed by an outward structure. The tangent configuration causes the anchors 20 to project outward toward from the cylindrical surface of the tack 10'. In this outward projecting position, the anchors are adapted to engage plaque or other vascular deposits causing the vessel to vary from its unobstructed fixed state, e.g. to be out-of-round.

The tangential projection of the anchors and bridges also advantageously enhances the control of the tack 10' upon deployment. A technique for deploying the tack 10' involves positioning the tack in a hollow catheter body. When positioned in the catheter body, the tack 10' is compressed to a compressed state. The rings 12 are highly conformal due to their construction, discussed above. As a result, the rings fully appose to the inner luminal surface of the hollow catheter body. In contrast, the bridges 14 and anchors 20 are more rigid and therefore are less conformal and as a result bite into the inner luminal surface of the catheter body. This creates a retention force within the catheter and limits unintended movement of some or all of the tack 10' toward a catheter deployment zone.

In some embodiments, the retention force of the barbs 20 is maintained or increased after partial deployment of the tack 10'. In particular, a region of relatively high flexibility can be provided at the junction of the bridges 14 and the rings 12. While high flexibility sections of stents can be areas of concern, such is not the case in the plaque tack 10' for reasons discussed below. The flexible region can have any material property or structure to enhance its flexibility at least compared to that of the bridges 14 such that upon movement of the ring 12 on the leading edge of deployment, the tangential configuration and tendency of the anchors 20 to bite into the hollow elongate catheter body is not diminished. Such is the case even though the leading edge ring 12 may expand to at least one-half of its fully expanded size.

As shown, the bridge 14 is connected to each ring at the inward apex 18 where at least a portion of the bridge 14 can be aligned, partially or substantially aligned with one of the struts that make up the ring 12 as has been described. For example, as shown, the bridge 14 is aligned with a high amplitude sinusoidal section of the pattern. The region of relatively high flexibility can be disposed between the inward apex 18 and the bridge 14.

In certain embodiments, expansion of the ring 12 may even cause the anchors 20 to rotate outward to increase the retention force in the catheter body. For example, expansion of the strut 26 may cause an inward deflection of the inward apex 18. While ring 12 is expanding a slight rotation of anchors 20 may occur which may cause a torqued outward deflection of the leading anchor and a corresponding torqued outward deflection of the trailing anchor. With reference to FIG. 5C, if the depicted ring 12 is first expanded upon moving out of the hollow catheter body, the anchor 20 to the right of the midline C may be deflected inwardly toward the central axis of the catheter body but the anchor to the left 20 will be deflected outward to increase the retention force thereof. Thus, the plaque tack 10' may be retained in the catheter during such partial expansion. Due to this feature the plaque tack 10' can be uniformly placed, as discussed further below in Section II.B.8.

The out-of-cylinder nature of the bridges 14 and anchors 20 also provide benefits to the deployed state. In particular, in some embodiments in an expanded state, the plaque anchors 20 are disposed radially outwardly of a cylindrical surface formed by the rings 12. The degree of out-of-cylinder can depend on the application, but in general may be sufficient to space at least a portion of the cylindrical surface from the inner walls of the vasculature when deployed. As such, the anchors 20 or the anchors combined with the rings 12 can be configured as focal elevating elements, which are discussed below in SECTION III.

As the plaque tack 10' expands within a blood vessel, the struts will engage the vessel wall and/or plaque. It is anticipated that in most situations, at least some of the struts will be deformed in response to irregularities of shape within the blood vessel. At the same time, the bridges 14 are less deformable and thus will resist such deformation retaining a circular configuration. The outward forces that are applied by the strut members are transferred into those areas that are in contact with the blood vessel wall. In some cases, when the tack 10' conforms to an irregularly shaped blood vessel lumen, the rigid central anchors become the region for blood vessel contact. The cumulative outward force of the struts in the rings 12 are applied through the bridges 14 to the anchors. Adjacent struts share their load with the contact region pressing the blood vessel into an enlarged configuration, such as a conformed circle.

Such a configuration can provide benefits such as helping the plaque tack 10' to remain in place after delivery and allowing the plaque tack 10' to respond dynamically to the movement and pulsing of the blood vessel itself. In addition, this configuration can have the benefit of reducing cellular response and device fracture by limiting strut fatigue and associated micro friction loading at the tack-blood vessel interface.

In some embodiments, the bridge 14 can include one or more anchor. In some embodiments, the bridge can be formed entirely of anchors.

After deployment of the plaque tack 10', the surgeon has the option of placing an angioplasty balloon at the site of the tack and inflating the balloon to press the anchor or anchors 20 into the plaque and/or wall of the blood vessel.

6. Flat Midline Markers

As discussed above, the plaque tack 10' has one or more markers 22. In one embodiment, a series of radiopaque markers 22 can be located on the tack 10'. In some embodiments, the radiopaque markers 22 are at the midline C of the device. The radiopaque markers 22 can be disposed between the two circumferentially oriented sinusoidal members or rings 12.

In some embodiments, the radiopaque markers 22 (e.g., platinum or tantalum) can be disposed adjacent to the plaque anchors 20. The radiopaque markers 22 can have one of many different shapes or configurations. In some embodiments, the radiopaque markers 22 have a planar or flat structure. As shown in FIG. 5C, each marker 22 is coupled with, such as by being press-fit or riveted into, a circular eyelet producing a flat leveled surface with the eyelet. The markers 22 offer clear visibility of the tack 10' in the catheter delivery system and provide guidance to the clinician for accurate placement during the procedure.

According to certain delivery methods, due to the co-placement of the anchors 20 and the markers 22 at the bridges 14 between the sinusoidal rings 12, the markers 22 can offer a visible clue to the clinician of the point when the release of the device will take place. For example, once the markers 22 meet a marker strip located at the tip of a delivery catheter sheath the full device can be deployed.

7. Simultaneous Device Placement in the Vessel

The plaque tack 10' can be configured for simultaneous placement within a blood vessel. Simultaneous placement of the plaque tack 10' can be defined as the entire plaque tack 10' being released from the delivery catheter prior to any all of the distal apices of the plaque tack 10' contacting the blood vessel lumen where it is to be placed. This event can occur when the anchors 20 are completely uncovered by the catheter sheath allowing the entire plaque tack 10' to expand against the lumen wall of blood vessel. The struts 26, 27, 28, 29 can be free floating, e.g., spaced from the vessel wall or applying negligible force to the wall, such that they do not contact the lumen wall prior to simultaneous placement. For example, the anchors 20 may have the effect of spacing a portion or substantially all of the struts 26, 27, 28, 29 from the vessel wall. Other forms of focal elevating elements are discussed below that can be used to space the tack 10' from the lumen wall.

Simultaneous placement offers the clinician the ability to control placement up until the markers 22 and/or anchors 20 are uncovered which can generate a full expansion event (struts adjacent to or contacting the lumen wall). In some embodiments, the full expansion event does not occur until the anchors 20 are uncovered due mainly to internal forces of the tack 10' urging the anchors 20 to engage the delivery sheath described above.

Another benefit of simultaneous placement is the reduction of any inadvertent dragging or pushing of struts against or along the lumen surface during the placement of the plaque tack 10'. Due to the complexity and variation of disease, location of placement, and dissections morphology, the ability of the outer surface of the plaque tack 10' to contact the lumen wall all at the same time is dependant on the deployment circumstances. However, the ability of the plaque tack 10' to contact the lumen wall completely upon release from the catheter sheath within fractions of a second has been observed.

8. Low Slope Force Curve

Figure 6A:
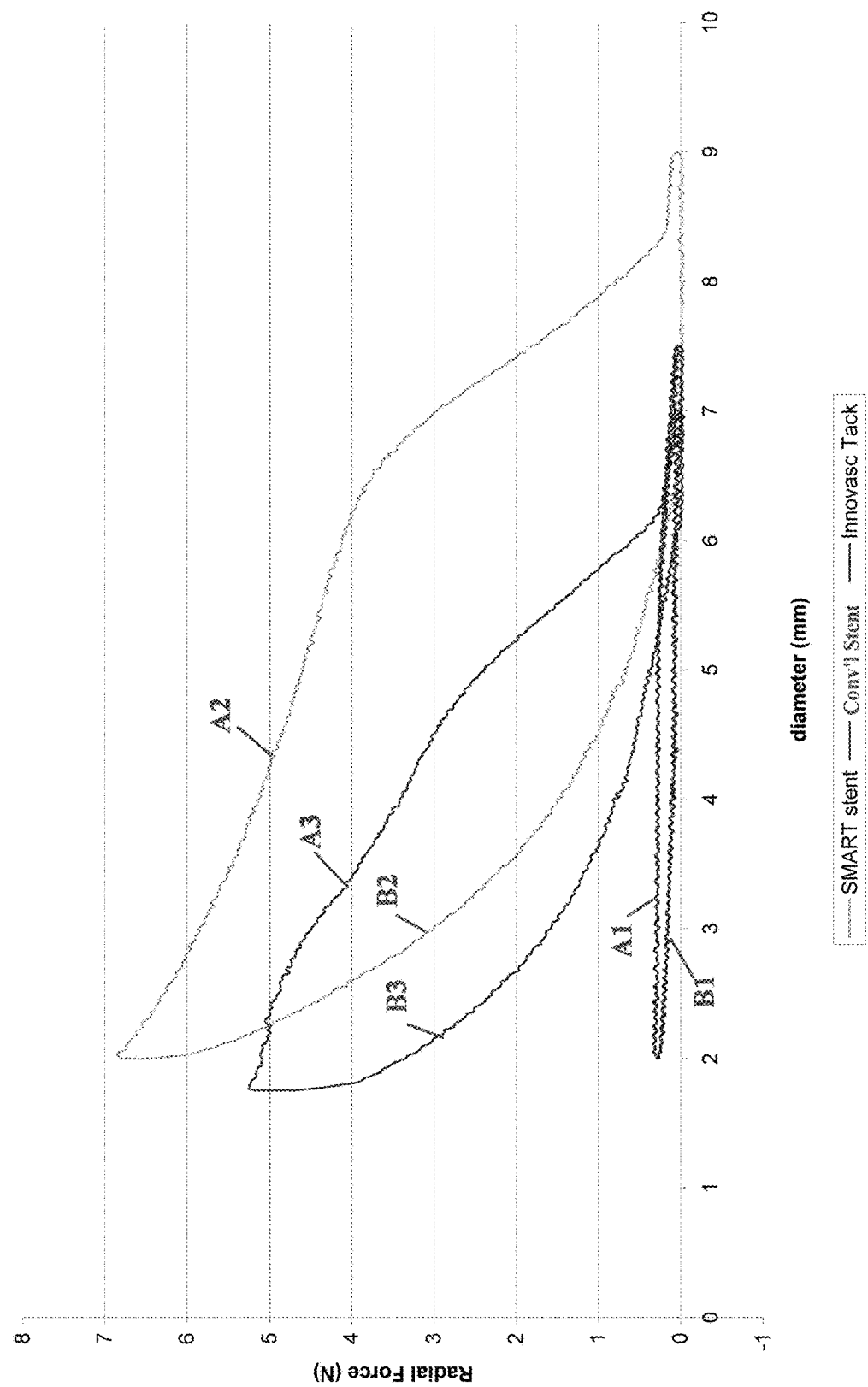
FIG. 6A is a chart comparing the expansion forces of a plaque tack to a stent.

Another unique aspect of the plaque tack 10' is that it can be configured with a force curve with an extended area having a low slope. A force curve, such as that illustrated in FIG. 6A, shows the amount of expansive force exerted by a self expanding plaque tack 10' or stent when moving from a compressed state to an expanded state. The expansion force of a device can be a factor in choosing the correct device to be placed in a particular blood vessel.

Still referring to FIG. 6A, the force curves of a SMART stent (i.e., a S.M.A.R.T.® Control transhepatic biliary stent by Cordis Corporation), another conventional stent, and a plaque tack having the wall pattern illustrated in FIG. 5A. The chart shows the radial force in Newtons (N) on the y-axis and the outer diameter of the device in millimeters (mm) on the x-axis. As the device is expanded or moved from the compressed state to the expanded state, the outer diameter increases. Because the devices are self expanding, they have a set amount of stored potential energy. When released, the potential energy is converted into kinetic energy as the internal forces try to restore the device to its expanded shape. The kinetic energy can then have an impact on the blood vessel when the device is implanted. Also, if the plaque tack 10' is not fully expanded a generally constant force will be applied to the vessel wall that corresponds to remaining potential energy stored in the tack 10'.

FIG. 6A shows a first dark line A1 showing the compression of a 7.5 mm plaque tack 10' from approximately 7.5 mm to approximately 2 mm of compressed diameter. After a gradual slope region between about 7.5 mm and about 6 mm, the slope of the force for each incremental reduction in diameter is greatly reduced, providing a narrow band of force required to fully compress the tack 10' from about 6 mm to about 2.0 mm. This portion of the force curve is very flat, meaning that the applied compression force does not greatly increase as the tack 10' approaches its fully compressed state. The force curve of the plaque tacks 10' upon expansion is illustrated by a dark lines B1 extending from 2.0 mm of compressed diameter to about 7.5 mm of expanded diameter. This portion of the curve can be thought of as the working portion, in which the force on the Y-axis is the force that the plaque tack 10' would apply to a vessel wall upon expansion. For example, if the plaque tack 10' were deployed in a vessel lumen having a bore of about 5.0 mm, the outward force of the tack 10' on the wall would be well under 1.0 Newton (N). Over a range of about 2 mm, the range of outward force is less than about 0.05 N+/−about 30%.

FIG. 6A shows in a dimmer line A2 the crimp performance of a SMART stent in a similar test. As discussed above in connection with other prior art stents, the SMART stent is a longer structure than the plaque tack 10'. In particular, the S.M.A.R.T.® stent tested was 40 mm long with a 8 mm unconstrained outer diameter, whereas the tack that was tested was 6 mm long with a 7.5 mm unconstrained outer diameter. However, it is believed that the comparison between the plaque tack 10' and the SMART stent illustrates a difference that would still manifest with a comparable length version of the SMART stent. As shown on the graph, the line B2 has a much higher crimp force in a range from just over 8 mm to about 6.5 mm. At about 6.5 mm, the slope of the crimp force decreases and the crimp force increases at a much slower rate. The outward force at the fully crimped state is much higher. Although the fully crimped state of the SMART stent corresponds to a smaller diameter, the crimp force for a comparable diameter is much higher on the SMART stent. Line B2 illustrates the working zone of the SMART stent that was tested. Line B2 shows the outward force over the range of expansion from about 2 mm to about 6 mm. As can be seen, the slope of line B2 is much greater at all points along its range between 2 mm and 6 mm. The practical effect of this higher slope is that the SMART stent is much more sensitive to changes in the bore size of the vessel into which the expanded plaque tack 10' is deployed.

As can be seen in FIG. 6A, in some embodiments, a low slope of the force curve can be essentially flat over about a 3 mm outer diameter expansion range. In other embodiments, a low slope of the force curve can be over a 2.5 mm outer diameter expansion range with a change in force of change less than 1 N. Factors in the ability of the tack to have a broad range where the radial forces change less than 1 N include the midline anchors, dual amplitude struts, and the varying strut thicknesses, discussed above.

FIG. 6A illustrates another conventional stent having a compression curve A3 and an expansion curve B3. The SMART stent is a widely used stent pattern. The curves A3, B3 represent another conventional stent design. Although the curves A3, B3 have lower peak compression force at the left-hand side of the curve, the slope is still dramatically higher over the range of use than is the tack illustrated by curve A1, B1.

The tack is radially self expandable through a range of at least about 2 mm, generally at least about 3 mm and typically through a range of at least about 4 mm or 5 mm, while exhibiting a radial expansion force of no more than about 5 N at any point throughout the range. In some embodiments, the maximum radial expansion force throughout the expansion range is no more than about 4 N and preferably is no more than about 3 N. In one embodiment, the tack is expandable over a range of at least about 3 mm (e.g., from about 3 mm to at least about 6 mm) and the radial expansion force is less than about 3 throughout that range. Generally the change in expansion force will be no more than about 3 N and preferably no more than about 2 N throughout the expansion range. In one embodiment, the expansion force drops from no more than about 2 N at 3 mm diameter to no more than about 1 N at 6 mm diameter. Typically the difference between the radial force of compression and the radial expansion force at any given diameter throughout the expansion range is no more than about 4 N, generally no more than about 3 N, preferably no more than about 2 N and in one embodiment is no more than about 1 N. In one implementation, the tack is expandable throughout a range which includes 3 mm through about 6.5 mm and the difference between the compression force and expansion force at each point along the compression/expansion range differs by no more than about 2 N and preferably by no more than about 1 N.

In general, the outward force of the plaque tack 10' is preferred to be as low as possible, while providing sufficient force to hold the plaque against the lumen wall through a wide range of luminal diameters. When force is elevated, e.g., by two to three times the sufficient holding force, adverse side effects can occur. These can include irritating the cells of the vessel wall that are in contact with the device, which can lead to re-stenosis. Although a very low force device is preferred for the typical treatment, higher force devices may be useful where loose plaque is found at calcified lesions.

One advantage to having a slow change in force as the device is expanding is the ability to predict the energy that the blood vessel experiences independent of the lumen diameter. Another value would be the reduction of necessary inventory for hospitals. For instance, it has been found that two part sizes of the tack 10' shown in FIGS. 5A-C can be used for plaque tacking treatments in blood vessels located throughout the leg, from hip to ankle. This is believed to be due in great part to the tack 10' having a slope of less than −0.3 N/mm.

C. Plaque Tack Design Parameters

One purpose of the plaque tack described herein, as distinct from traditional stenting, is to reduce the amount of implanted foreign material to a minimum while still performing focal treatment of the blood vessel condition so as to cause a minimum of blood vessel wall reaction and adverse post-treatment restenosis. The plaque tack is designed to have substantially less metal coverage and/or contact with the blood vessel surface, thereby inciting less acute and chronic inflammation (See FIG. 6B). Reduced contact area of implanted material against the blood vessel wall is correlated with a lower incidence of intimal hyperplasia and better long-term patency. Substantially reduced length along the axial distance of the blood vessel permits a more targeted treatment, correlates with less foreign body coverage of the blood vessel surface, avoids covering portions of the surface that are not in need of coverage, and correlates with both early and late improved patency of blood vessel reconstructions.

The plaque tack can be deployed only where needed to tack down plaque that has been disrupted by balloon angioplasty or other mechanisms. Rather than cover an entire area of treatment, the plaque tack can be placed locally and selectively, for example, not extending into normal or less diseased artery segments (See FIG. 6B). This permits the blood vessel to retain its natural flexibility because there is minimal to no scaffolding when a small profile tack is used locally or even when multiple tacks are spaced apart over the area of treatment. Still further reduction in the pressure profile can be achieved by using "points-of-contact" to achieve higher pressure at focal points and lifting the neighboring strut section away from the blood vessel wall to reduce the overall load of the outward pressure elsewhere on the tack strut structure.

One parameter for design of a plaque tack is having a tack axial length to expanded diameter (L/D) ratio of no more than about 2.0, often no more than about 1.5 and in some implementations no more than about 1. In one embodiment, the tack has about an L/D ratio of 0.8. That is, the length of the tack along the axis of the blood vessel is about equal to or less than the expanded diameter of the tack. The preferred plaque tack is thus shaped like an annular ring or band, whereas the typical stent is shaped like an elongated tube. The small-profile tack can thus be used locally for targeted treatment of disrupted regions of the blood vessel surface with a minimum of foreign material coverage or contact. Tests show that a plaque tack with an axial length/diameter ratio causes almost no biological reaction or subsequent blood vessel narrowing in comparison to a traditional stent where the axial length is greater than the diameter, and usually much greater. Tests indicate that device L/D≤1 results in a reduction in scaffolding much less than that of the typical stent and causes less arterial wall reaction. For application at sites of small dissection after balloon angioplasty, a plaque tack of minimal footprint may be used such as a single, thin ring-type tack with an L/D ratio in the range of 1/10 to 1/100.

Studies on stenting have shown that the axial length of a stent is correlated with a tendency for occlusion in multiple vascular territories. The more stent axial length that has been placed, the higher likelihood that the reconstruction will fail. The axial length of a stent is also directly linked to the frequency and tendency of the stent to break when placed in the superficial femoral artery. The medical literature indicates that the superficial femoral artery performs like a rubber band, and it is likely that changes to the natural elongation and contraction of the superficial femoral artery play a significant role in the failure mode of superficial femoral artery stents. In contrast, the small-profile plaque tack can be implanted only in local areas requiring their use, thereby enabling the blood vessel to retain its natural flexibility to move and bend even after the surface has undergone tacking. Multiple tacks may be implanted separated by regions free of metallic support, thereby leaving the artery free to bend more naturally.

Outward radial pressure exerted on the blood vessel wall can also be substantially reduced by the small-profile tack design, even when multiple tacks are used in a spaced-apart configuration. To minimize this outward force while still providing the required retention of dissections against the arterial wall, a series of anchor barbs or focal elevating elements can be utilized. The presence of these features applying focal pressure to the wall of the artery allows the rest of the tack to apply minimum outward force to the artery wall. The points which apply the pressure can be very focal, and this is where the most force is applied. The focal nature of the application of the pressure exerted by the tack also minimizes the structural effects of the device. Uniformly distributed anchors or focal elevating elements can provide a distribution of radial energy maximizing the tendency to form a circular lumen.

Another important parameter for design of a plaque tack is the ratio of Vessel Coverage Area (C) to Total Vessel Surface area (TVS). In one definition, the value C is the length of the prosthesis (e.g., stent or tack) times the average circumference of the vessel in which it is placed and the value TVS can be the length of the lesion or area requiring treatment times the same nominal circumference. This can also be simplified to a ratio of total length of the prosthesis when expanded to the nominal circumference divided by the length of the lesion in the vessel. These concepts can be applied to one tack device or when several spaced-apart tack devices are placed across the length of a blood vessel treatment area. Where multiple stents or tacks are used, a simplified ratio could be total non-overlapping length divided by lesion length or could be the sum of the length of the prostheses divided by the sum of the length(s) of the lesion(s). For a plaque tack, the C/TVS ratio is in the range of about 60% or less, whereas for a stent it can be 100% or more (if applied to overlap the treatment site).

For a focal lesion, the conventional treated vessel length is X+10 mm to 20 mm where X is the length of the lesion and the added length is adjoining on normal or less diseased artery proximal or distal to the lesion. In traditional stenting the entire treated vessel length would be covered with a stent. For example, in the case of a 2 cm lesion, the treated vessel length would be 3 to 4 cm (usually a single stent of this length would be selected), so that C/TVS is 150%-200%. In contrast, with tack placement about ½ of X would be covered, and none of the adjoining normal or less diseased artery would be treated. For example, in a 2 cm lesion, approximately 1 cm would be covered, so that the C/TVS ratio is about 60% or less. An advantageous aspect of this innovative approach is placement of bands only in regions of dissections requiring vascular tacking.

As described previously, in some embodiments, a tack device 10' is formed with rings or mesh bands 12 connected by longitudinal bridge members 14 (FIG. 5A). In the figure, the tack 10' is shown compressed for delivery in a blood vessel. When expanded, the diameter of the tack device can be about equal to the axial length of the tack device.

Figure 6B:
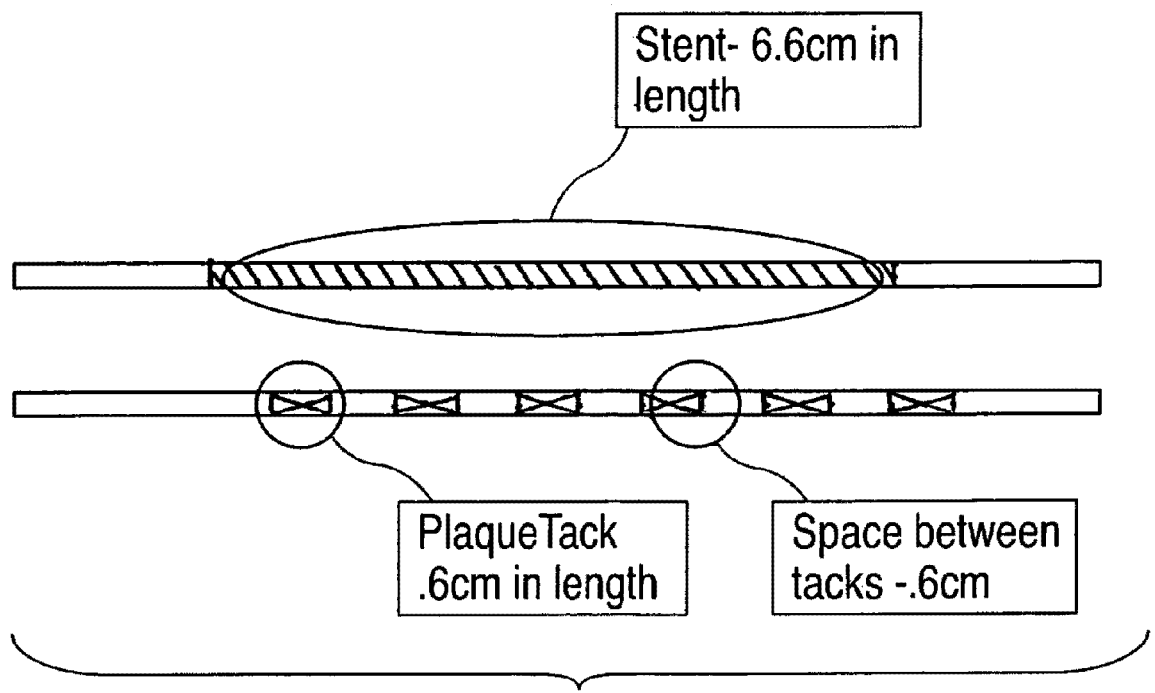
FIG. 6B illustrates the use of multiple plaque tacks which are spaced apart over the length of a treatment site as compared to a typical stent.
Figure 7A:
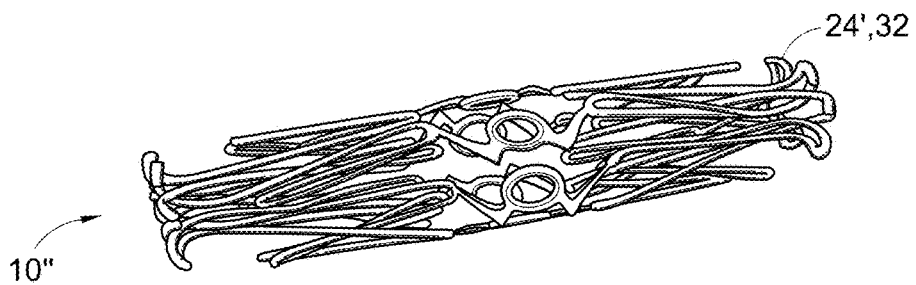
FIG. 7A shows another embodiment of a plaque tack in a fully compressed state.
Figure 7B:
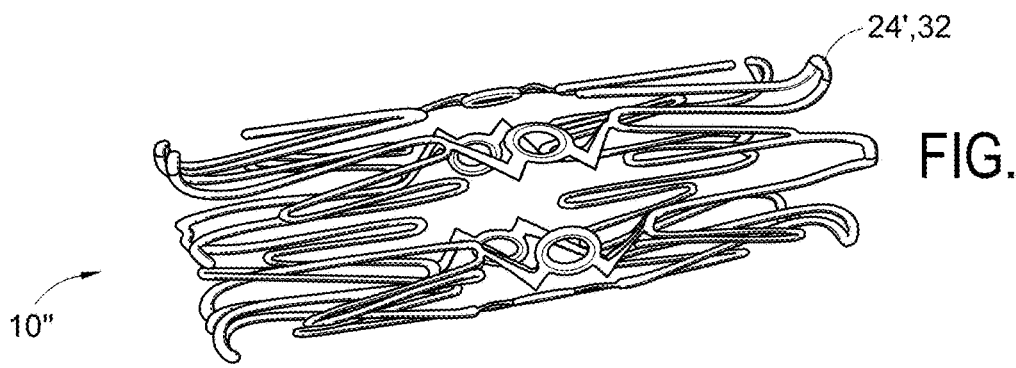
FIG. 7D shows the plaque tack in a fully expanded state and FIGS. 7B and 7C show the plaque tack in states of expansion between the fully compressed and expanded states.
Figure 7C:
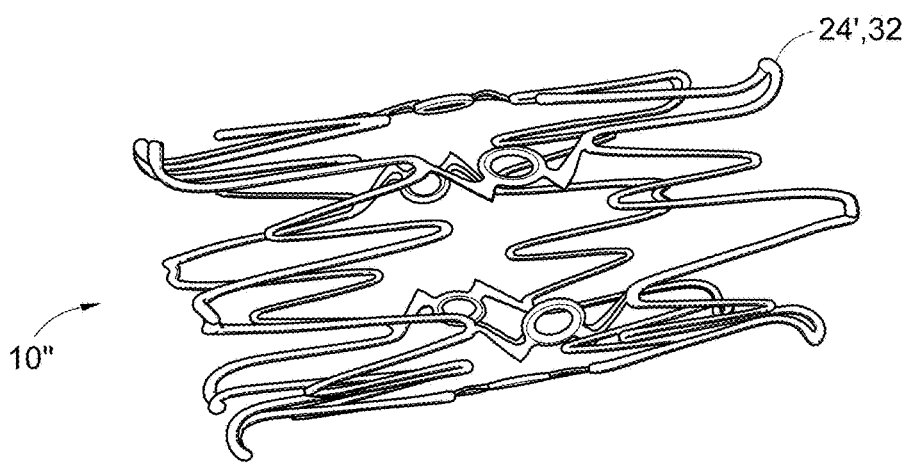
Figure 7D:
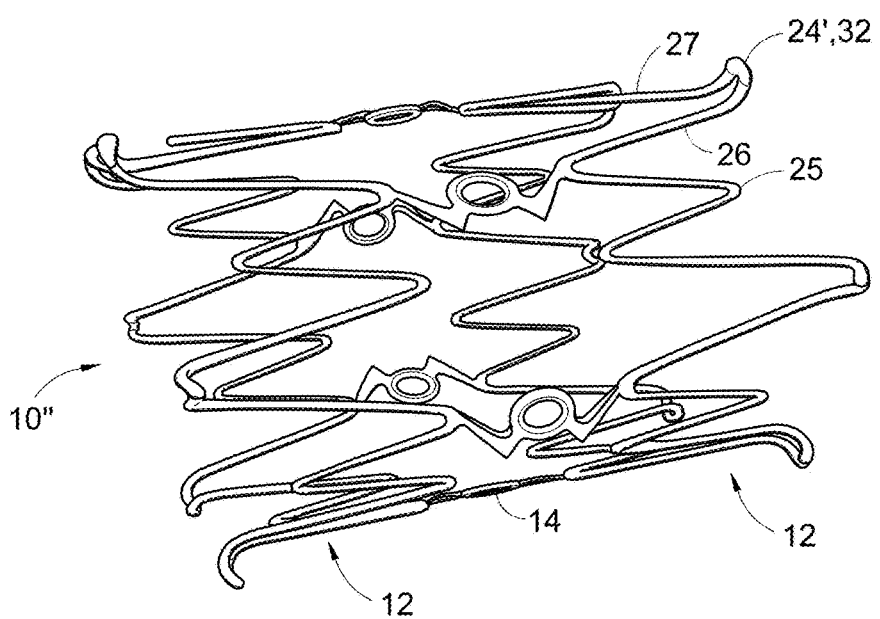

FIG. 6B illustrates the use of multiple tack devices which are spaced apart over a length of blood vessel at a treatment site as compared to a typical stent. Preferably, the spacing between tack devices is at least the axial length of the tack device. Note that the spacing between adjacent tack devices leaves untreated vessel area. A typical stent is shown in the upper part of the figure compared to the use of 6 spaced-apart tack devices at the bottom part of the figure. In this non-limiting example, the overall length of treatment area is 6.6 cm (the same length of the stent) while each band is shown as 6 mm long separated by 6 mm spaces. Therefore, the Vessel Coverage Area for the stent is the same as Total Vessel Surface area (=6.6 cm×0.6π, or 12.44 cm$^2$) which gives a C/TVS ratio of 100%. For the series of spaced-apart tack devices, C is equal to 6×0.6 cm×0.67π, or 6.78 cm², while TVS is 12.44 cm², therefore the C/TVS ratio is equal to 54.5%.

When two or more stents need to be employed over an extended length of treatment site, it has been a conventional practice to overlap adjoining stents to prevent kinking between stents. Due to the increased metal lattice, the region of overlap becomes highly rigid and noncompliant. This noncompliant doubly rigid region further limits the natural arterial flexibility and increases the tendency for restenosis. Stent fractures occur more frequently in the superficial femoral artery where this bending has a high frequency and are common when multiple stents are deployed and overlap. Stent fractures are associated with a higher risk of in-stent restenosis and re-occlusion. In contrast, the plaque tacks are designed to be applied in local areas and not to be overlapped. Optimal spacing is a minimum of 1 tack axial length apart for tacks. This permits the artery to maintain its flexibility, and only a half or less of the treated length of the artery will be covered with metal. It should be noted that in the case where restenosis occurs after tack placement the overlapping of the entire treated length with a stent still allows the stent to retain its patency. This is due to the repeated pattern of regions where no tacks are placed offering regions of relief and the artery to flex.

The literature in the industry has noted that important factors in stent design may be the ratio of Relative Metal Surface Area (RMS) and the number of longitudinal segments in the device structure, for example, as presented by Mosseri M, Rozenman Y, Mereuta A, Hasin Y, Gotsman M., "New Indicator for Stent Covering Area", in *Catheterization and Cardiovascular Diagnosis*, 1998, v. 445, pp. 188-192. More particularly, for a given metal surface area, a higher number of longitudinal segments (each of which is thinner) can reduce the size of the gap between adjacent segments, reducing the tendency for prolapse. As adapted from the RMS measure, an equation for Effective Metallic Interface (EMI) may be used to compare the embodiment of the tack device with longitudinal bridging members to a typical stent, as follows:

$$EMI = \frac{(1+n^2)C}{\sum_{s=1}^{x}(lw)_S}$$

Where x is the number of sections of metal, l is an individual metal section length, w is an individual metal section width, C is the vessel coverage area underneath the device (lumen surface), and n is the number of bridge members longitudinally connected between circumferentially oriented segments. The summation found in the denominator can be interpreted as the total metal surface area. The embodiment of the tack device with longitudinal bridging members has an EMI≤10, whereas the EMI of a typical stent would be several times greater. This low EMI is due to the nature of the tack design having a small foot-print and minimal longitudinal bridges while a stent typically has a large foot-print and would be a multiple several times that.

Figure 9:
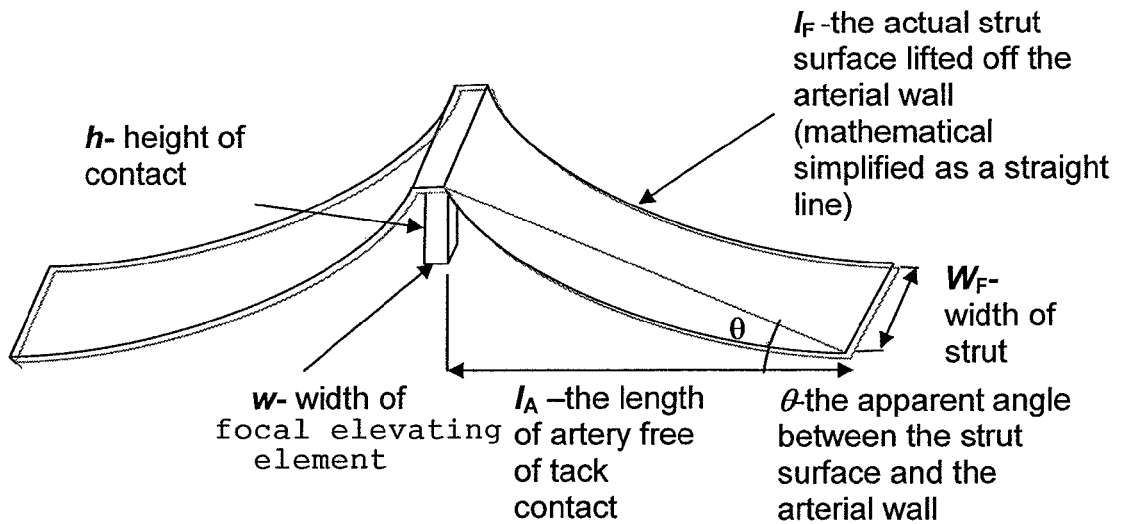
FIG. 9 is a schematic diagram illustrating the variables for computing the elevated tack surface due to the use of focal elevating elements in a plaque tack device.

To further reduce the EMI through the inclusion of lift-off-bump features (such as anchors, barbs, or focal elevating elements), an improved $EMI_F$ can be obtained for the Tack Effective Metal Interface as provided with floating elements (see FIG. 9). $EMI_F$ can be defined as:

$$EMI_F = \frac{C(1+(n-n_F)^2)}{\sum_{s=1}^{x}(lw-l_F w_F)_S}$$

Where all variables are the same as those in the EMI equation with the addition of $l_F$ is an individual metal section length that is not in contact with the artery (floating off the artery), and $w_F$ is the width of the same section. If no floating sections exist then $n_F=0$ and $l_F w_F=0$ and therefore $EMI_F=EMI$.

The inclusion of metal sections that are floating (floating length $l_F$, floating width $W_F$, and number of floating bridges $n_F$,) reduces the EMI further which is captured mathematically as a summation with negative variables in the $EMI_F$ equation.

The presence on the plaque tack of lift-off-bump features (such as anchors, barbs, or focal elevating elements) minimizes the pressure of the overall structure upon the blood vessel wall by transferring regional outward forces to focal pressure points, thereby applying a higher pressure at the focal points. The presence of the lift-off-bump features applying focal pressure to the artery wall allows the rest of the tack to apply minimum outward force to the artery wall. Wherever the lift-off-bump features are placed, the outward radial energy is maximized at that region, producing a slight outward bowing of the arterial wall. The outward bowing can be used for arterial shaping or molding, for example, 5 or more uniformly distributed focal points can be used to form a circular lumen. Circular lumens offer additional benefit from the standpoint of the vessel wall interaction, independent of the vascular injury.

In any of the embodiments herein described, the plaque tack device may be made from Nitinol, silicon composite (with or without an inert coating), polyglycolic acid, or some other superelastic material, as well as stainless steel, tantalum, a cobalt chromium alloy, bioabsorbable or bioresorbable materials (including bioabsorbable/bioresobable metals) or a polymer. The strip of material can be created from ribbon, round or rectangular wire or a sheet of material processed through photolithographic processing, laser or water cutting, chemical etching or mechanical removal of the final shape, or the use of bottom up fabrication, for instance chemical vapor deposition processes, or the use of injection modeling, hot embossing, or the use of electro or electroless-plating. It may be fabricated from metal, plastic, ceramic, or composite material.

The plaque tack device is designed to be inherently self-aligning, i.e., its mechanical installation can accommodate small misalignments. By reducing stress in the strut members while gripping the arterial wall in the center of the design, the tack self aligns with the arterial longitudinal axis. Design features that offer stress relief and provide uniform distribution of the unfolding struts include narrow spacing of the anchors, non-uniformly thick struts, and anchors heads that are angled to reduce device from springing forward during delivery. As discussed above, circumferentially oriented anchors located at each bridge member offer gripping force with the catheter tip and embedding features when lying on the artery wall. These design features serve to facilitate placing the tacks in specific locations within diseased blood vessels.

III. Improvement of Focal Elevating Elements

FIGS. 7A-D show a plaque tack 10″ that is similar to that of FIGS. 5A-C except as discussed below. In particular, the plaque tack 10" includes a feature that reduces the amount or character of interactions between the plaque tack 10" and the vasculature by elevating a portion of the plaque tack 10" off of the vessel wall when deployed.

Figure 8:
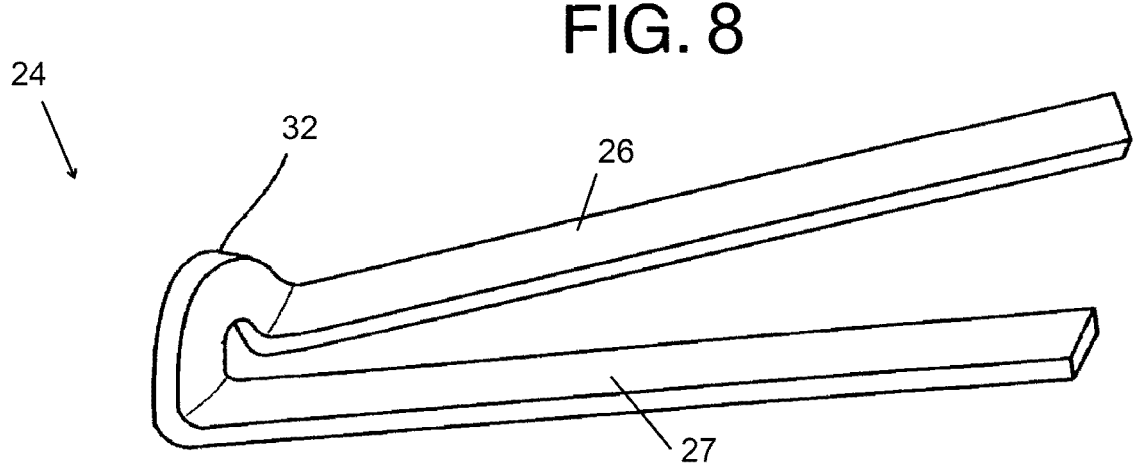
FIG. 8 is a schematic view of the focal elevating element of a plaque tack in FIGS. 7A-D.

In particular, the high outward apex 24' formed by the struts 26 and 27 is bent or turned upwards, or radially outwards, to form a focal elevating element (FEE) 32. FIG. 8 shows a schematic view of the FEE 32. In this embodiment, the high outward apex 24' is bent to form an angle with the struts 26 and 27. In this way the FEE 32 can help minimize the amount of the tack 10" that is in contact with the plaque and/or vessel wall while also localizing the forces at few points to more securely place the plaque tack 10". These as well as additional benefits will be described in more detail below.

A plaque tack devices may be provided with focal elevating elements on the annular periphery of the device. The focal elevating elements are distinguished from the anchors and barbs generally having greater plaque or arterial wall penetration to anchor or stabilize the tack in the blood vessel.

The focal elevating elements may or may not penetrate but still offer regional strut elevation and are preferably placed at apices of struts or periodically along (e.g., perpendicular to) strut lengths. For both anchors and focal elevating elements the size of the interface between the tack and the arterial wall is preferably equal to or shorter than the strut width in at least one direction. The focal elevating elements can be similar to anchors but either do not penetrate or penetrate the tissue only slightly, thereby minimizing the amount of material surface area in contact with the plaque, and offer a set of relief sections for the outward pressure of the tack device adjacent to the focal elevating elements, thereby minimizing the friction generated at the blood vessel wall.

The focal elevating elements can be formed and configured on the annular periphery of the tack device in a similar manner as described for the previous tack device embodiments and can include the raised contact sections in addition to anchors or sharp points. The contact sections can provide improved tacking characteristics in that they increase the contact forces at the contact sections by compressing the plaque at the contact regions and decrease the outward force at the sections neighboring the focal elevating element. This offers regional pressure relief in some sections and increase contact pressure at the bumps or sharp points collectively offering a reduction in trauma and cellular response of the blood vessel wall.

Because the tack device is held in place by its own pressure exerted on the blood vessel surface, it is susceptible to friction, including slight movement between the device and the vessel surface. Every time the organ moves (e.g., the leg during ambulation), the artery moves. It can be inferred that when the artery moves the working device sitting within the artery also moves but not necessarily every point of contact moves in synch with each other. Whenever there is even a small mismatch in movement between the artery and the device the artery and device rub against each other promoting cellular reaction and device failure. It has been deduced from experimental that this rubbing may irritate the endothelium causing an inflammatory response. In some embodiments, strategically placed focal elevating elements (FEEs) are implemented to reduce the overall regional friction load (thought to be a source of inflammation, cellular proliferation, and the healing response that leads to restenosis) of the area being held open.

As an example, a blood vessel such as the popliteal that is cyclically shortened and elongated is believed to have a cellular or tissue structures that elongate and compress in a direction parallel to the axis of the vessel. The natural behavior of this cellular or tissue structure involves a significant amount of local movement along this axial direction. If an implant to be placed in such a vessel is designed to contact the vessel wall in a direction transverse to this axial direction, the natural behavior of these tissues or cells will be greatly disrupted. For example, the tissue will be constrained and the natural movement will be greatly reduced. Also, rubbing can occur along the edges of the transversely contacting structure, resulting in friction and/or abrasion of the tissue and corresponding inflammation. FEEs, in contrast, reduce the disruption of the natural behavior of the tissue or cells. If incorporated into a tack device or other prosthesis, FEEs can focus the contact at zones that are spaced apart along a direction transverse to the predominant direction of motion (e.g., the axial direction in the case of the popliteal or similar vessel). Between these zones of focused contact corresponding to the FEEs, the interaction of the compressing and elongating tissue or cells with the structure of the implant is greatly reduced. In this in-between zone, the motion between the compressing and elongating tissue or cells can approach that of the tissue or cells before the implantation of the prosethesis. Raised sections produced by the FEEs limit the histological response of the tissue and also the fatigue of the device by limiting the contact between the device and the tissue.

Independent of the overall amount of contact and number of FEEs, the tack devices smooth the lumen wall, and allow more natural vessel movement. Where FEEs offer the greatest value is in there ability to reduce the amount of interaction between tissue or cells that move, elongate or compress, which can produce rubbing or friction to such tissue or cells. It is this highly localized movement or "micromovement" that increases the cellular response of the blood vessel surface to the foreign device.

The focal elevating elements are designed to reduce effective metal interface (EMI) by minimizing the overall material contact with the blood vessel surface. The focal elevating element (FEE) is preferably configured as a narrow, lifted feature with enough height to lift adjacent strut sections of the tack device off from contact with the arterial wall in order to reduce the surface area of foreign material in contact with the arterial wall. Reducing the contact burden is of particular value when the strut members are connecting circumferential rings or circumferentially oriented strut bands. Strut sections oriented against the natural grain of the cellular orientation that are in contact with the blood vessel walls can produce microfriction when they move or rub against the blood vessel walls. By reducing the foreign material contact area against the blood vessel wall, the tendency for production of microfriction contact is reduced.

Referring to FIG. 9, a schematic diagram illustrates some of the design assumptions for the use of focal elevating elements on a plaque tack device. In the figure, h refers to the height of the focal elevating element that is extended out of the blood vessel (note: the penetration depth of the focal elevating element that is anchored into the artery or plaque body is not included in this calculation), w refers to the width of the focal elevating element (at its base), and $l_F$ refers to the adjacent strut surface lifted off the arterial wall (mathematically simplified as a straight line). The struts adjacent to the focal elevating element may be fabricated with shape memory materials or designed as a compression wave providing compensation for lumen diameter variations. The strut forces adjacent to the focal elevating elements produce an outward bowing of the struts produced by the forces of the struts wanting to expand until they are in contact with the blood vessel wall. $l_A$ refers to the length of arterial wall that is kept out of contact with any adjacent strut structure by the focal elevating element.

One or more of the features labeled in FIG. 9 can be varied to provide advantageous FEE performance. For example, h can vary depending on the size of the delivery catheter for instance a 4Fr provides a h of up to 150 um. In certain embodiments, a tack with FEEs configured for delivery in a 4Fr catheter can have h of about 100 um or less. An example embodiment that can be deployed with a 4Fr delivery system has one more FEEs with h of about 75 um. Larger tacks with FEEs, e.g., configured for delivery in a 6Fr catheter can have an h of up to about 300 um and in some cases 225 um or less. An example embodiment that can be deployed with a 6Fr delivery system has one more FEEs with h of about 200 um. Still larger tacks with FEEs, e.g., configured for delivery via a 8Fr catheter, could have an h of up to 950 um while in certain embodiments FEEs of up to 500 um could be provided. An example embodiment that can be deployed with an 8Fr delivery system has one more FEEs with h of about 400 um.

Any of the foregoing dimensions of h may be combined with a variety of dimensions of W of the FEE. The W dimension would typically be the width of the strut but could be as little of 50% the strut width and may be between about 50% and about 100% the width of the struts at the location of the FEE. $I_f$ and $I_a$ are a function of W, the radial force of the system, the topography of the lumen, and the delivery device, e.g., varied if a balloon is used to press the device into the artery. If we just look at W (non elastic system) then $I_a$ may be about equal to the length of the strut. As outward force (both from the elastic nature of the metal and the balloon assist) increases then $I_a$ can be reduced, approaching 0. However, in various embodiments, $I_a$ is at least about 20 um.

The focal elevating elements may be formed as cylindrical, rectangular, linear, spherical, conical, tear dropped, pyramidal, or inclined elements on the annular periphery of the tack device. They can be formed by bending or stamping a section of the tack structure, by an additive process (such as by welding or annealing on a peripheral surface), by a subtractive process (such as by grinding or etching away surrounding material so that the bump element is higher than the surrounding surface), or by modifying small sections of the peripheral surface to be higher than the surrounding surface before or after sheet or tube cutting. For example, one method of modification of small sections of a mesh tack structure is by knotting, twisting, bending or weaving small sections of the wire mesh to produce raised elements from the mesh surface which are the interface with the artery wall of the tack devices.

Properly oriented and symmetrically positioned focal elevating elements can provide foci for expansion force. As the device exerts outward forces and the artery exerts inward forces, the focal elevating elements can be positioned at strategically located positions reducing the outward pressure of strut sections neighboring the focal elevating elements.

Both anchors and focal elevating elements can offer strategic advantages that include: the reduction in pressure burden across the tack struts by reducing the contact area and translating the outward forces to the anchors and focal elevating elements, minimizing surface contact which offers a reduction in the tendency of frictional loading driven by micro movement between the arterial wall and the tack strut, and the stabilization of anchoring the tack where the anchor or focal elevating element penetrates the vessel wall a fraction of the features height.

Figure 10:
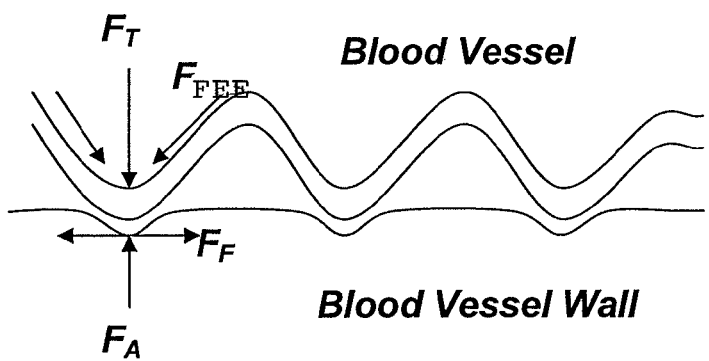
FIG. 10 illustrates use of a plaque tack with focal elevating elements for holding a plaque against a blood vessel wall.

Because the tack device is held in place by its own outward force pressure exerted on the plaque and blood vessel surface, it may be susceptible to friction, i.e., slight movement between the device and the vessel surface. FIG. 10 illustrates the forces at play between the tack's focal elevating elements and the arterial wall. $F_T$ is the circumferential force exerted by the tack device against the arterial walls force, $F_A$. $F_{FEE}$ is an additive circumferential force at the focal elevating element generated by the design and material choice and $F_F$ is the frictional force of the artery generated when the artery changes its orientation or shape due to body forces. Every time a body party moves, the blood vessels move slightly as well. The focal elevating elements can be strategically positioned to reduce local friction loading which may cause inflammation, cellular proliferation, or bodily response that leads to restenosis.

The number and locations of focal elevating elements can affect the overall Relative Metal Surface Area (RMS) which was explained previously. The focal elevating elements may be positioned along the lengths of the tack device surfaces such that a minimal amount of metal surface area is in contact with the artery wall. Focal elevating elements placed at bridges between circumferential strut rings or at the apices of strut sections of the tack device can offer a majority of arterial injury relief. When focal elevating elements are placed only at apices and bridges, the RMS of the strut members making up the concentric ring changes a little while the RMS of the bridges is reduced more significantly, due to the narrow length, offering relief of relative motion of the circumferentially oriented strut rings.

Figure 11:
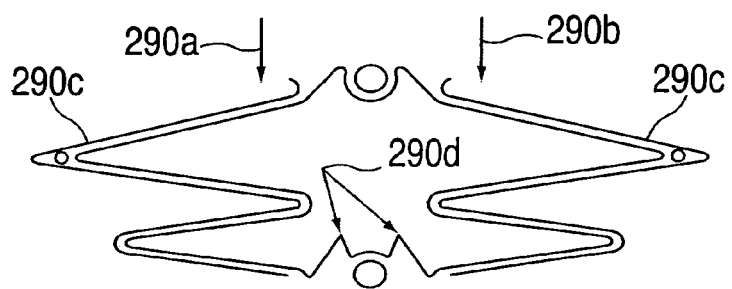
FIGS. 11 and 12 illustrate a variant use of focal elevating elements on a plaque tack.
Figure 12:
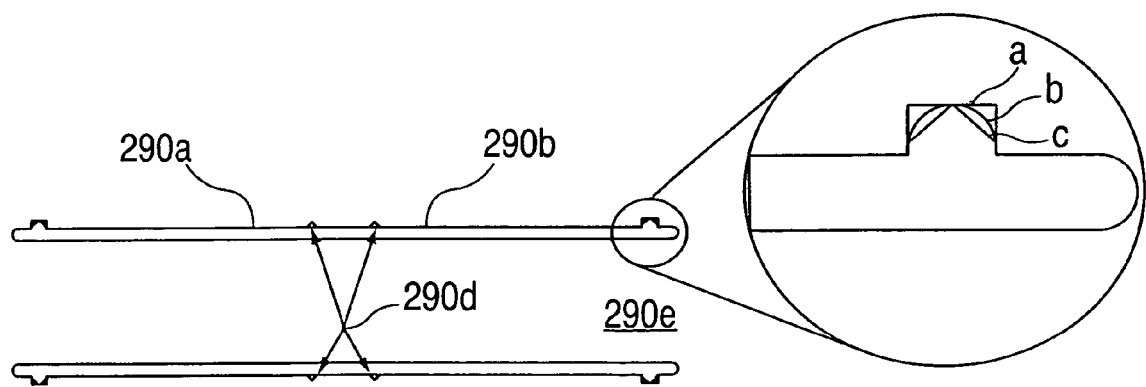

FIGS. 11 and 12 illustrate the use of focal elevating elements on a tack device of the type described above with respect to FIGS. 5A-C having two or more concentric ring sections joined by bridges in between. FIG. 11 shows a cell of two adjacent ring sections 290a and 290b with strut sections 290c and which are joined in the middle by bridges 290d. FIG. 12 shows the ring sections expanded under expansion force and opposing sets of focal elevating elements 290e deployed on opposite ends of the two adjacent ring sections 290a and 290b. An inset to the figure shows the round elevating element having a height raised from the strut surface.

Figure 13:
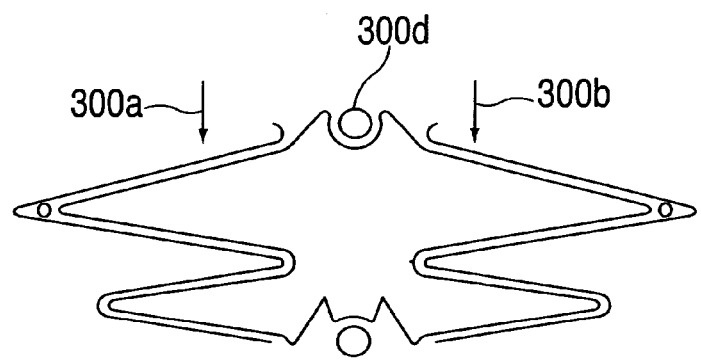
FIGS. 13 and 14 illustrate another variant of focal elevating elements on a plaque tack.
Figure 14:
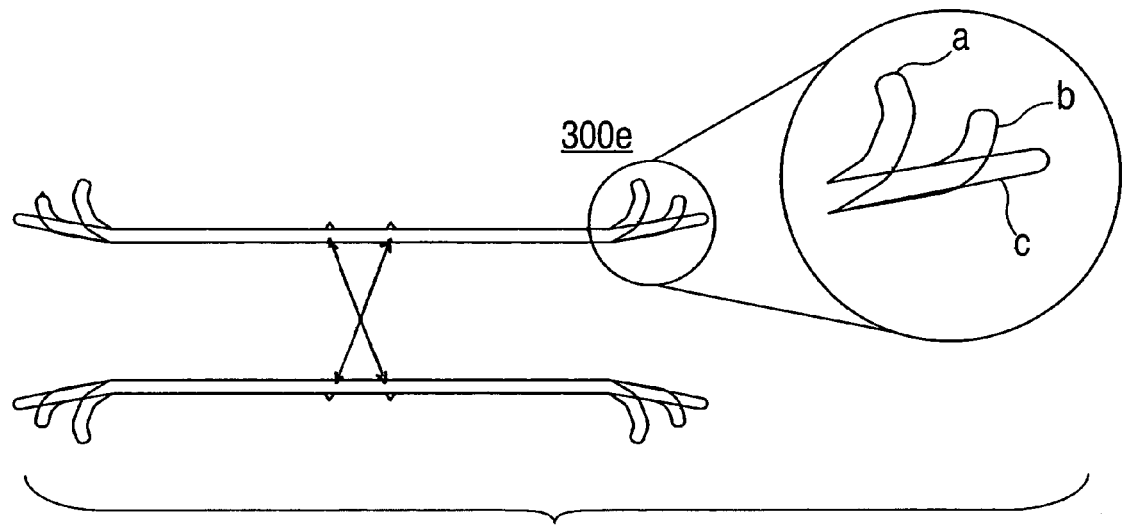

FIGS. 13 and 14 illustrate a cell of another variant of focal elevating elements formed on a tack device having two or more concentric ring sections 300a, 300b joined by bridges 300d in between. In this cell variant, the focal elevating elements 300e are formed by bending the sections of the strut (illustrated as the strut apex) out of the circumferential plane into varying degrees of tilt such as position "a", or position "b", up to a 90 degree vertical orientation shown in position "c" to form the elevating element.

Figure 15:
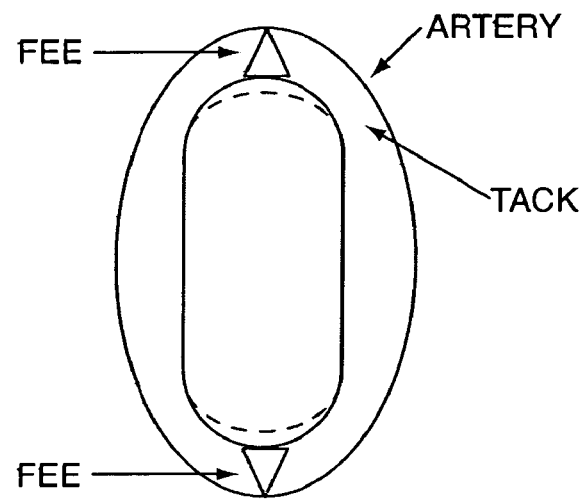
FIG. 15 illustrates the use of focal elevating elements to reshape artery walls into a desired cross-sectional shape.

Inherent in the use of shape memory alloys for the tack devices is the ability to conform to the shape of the blood vessel walls. Because the focal elevating elements can exert an expansion pressure on the blood vessel walls with a minimal risk of injury, they can be designed to reshape the blood vessel walls to a desired shape. FIG. 15 illustrates the focal elevating elements (FEE) positioned in diametrically opposite positions and formed with an extended height to reshape the artery walls into an ellipse cross-sectional shape which may better match the arterial cross section (such as an arterial branch) or expand the lumen to be more open in plaque-free areas.

Figure 16:
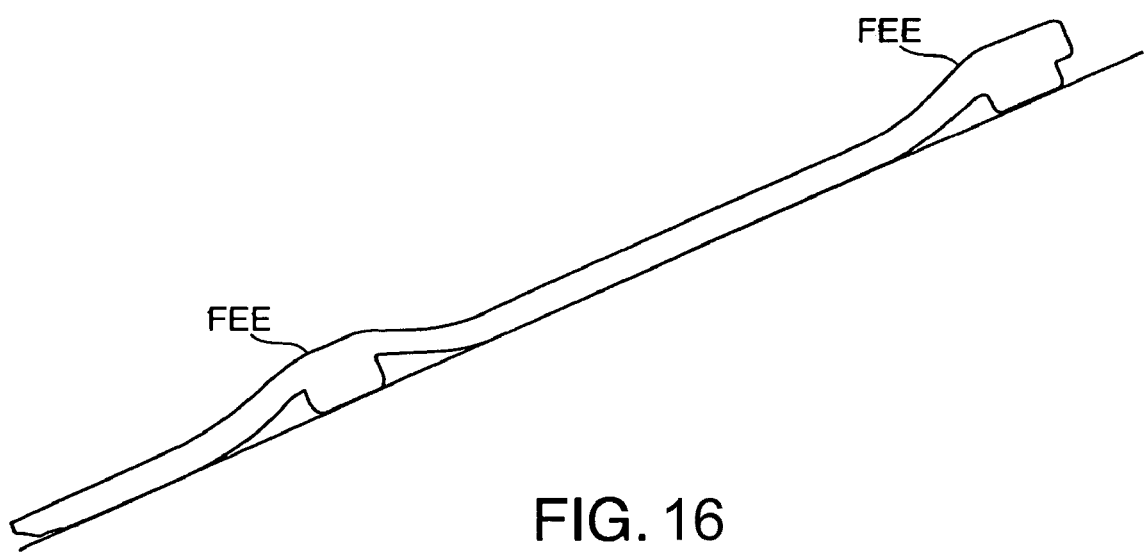
FIGS. 16-22 illustrate variations in forming and positioning focal elevating elements on the struts of a plaque tack.

FIG. 16 shows a side view of FEEs spaced along a strut length having a small area lifted off the arterial due to the height of the FEE lifting a short distance of the neighboring strut length. Outward forces generated by the design or material used allow for only a small section on either side of the FEE to be lifted off the blood vessel wall.

Figure 17:
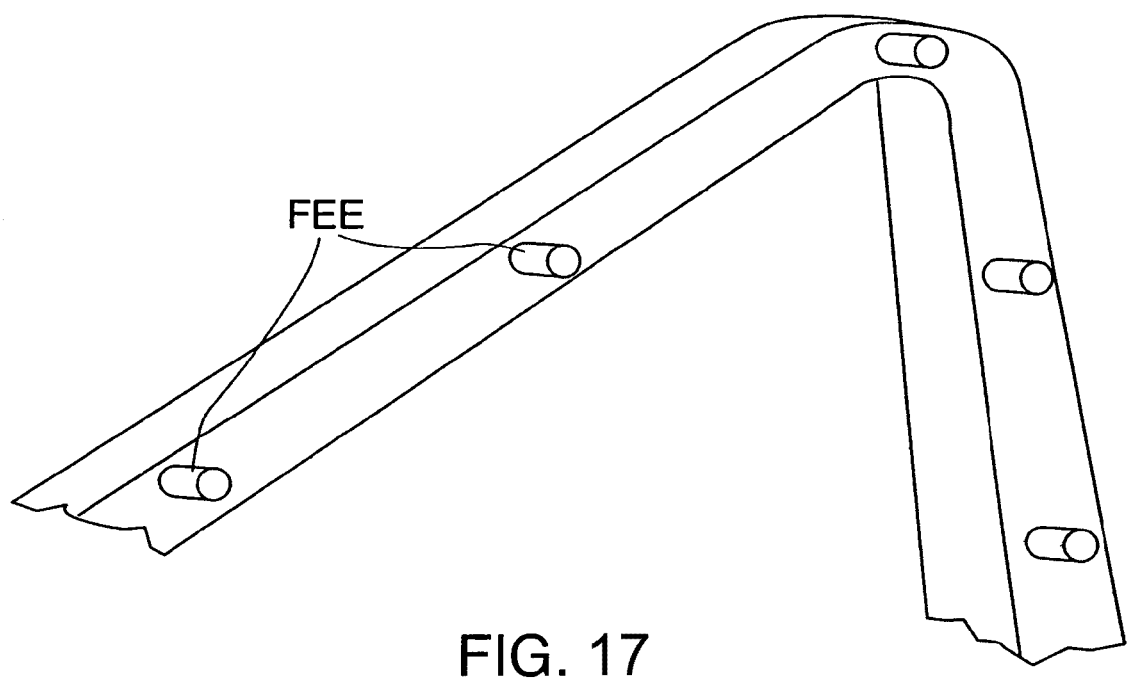
Figure 18:
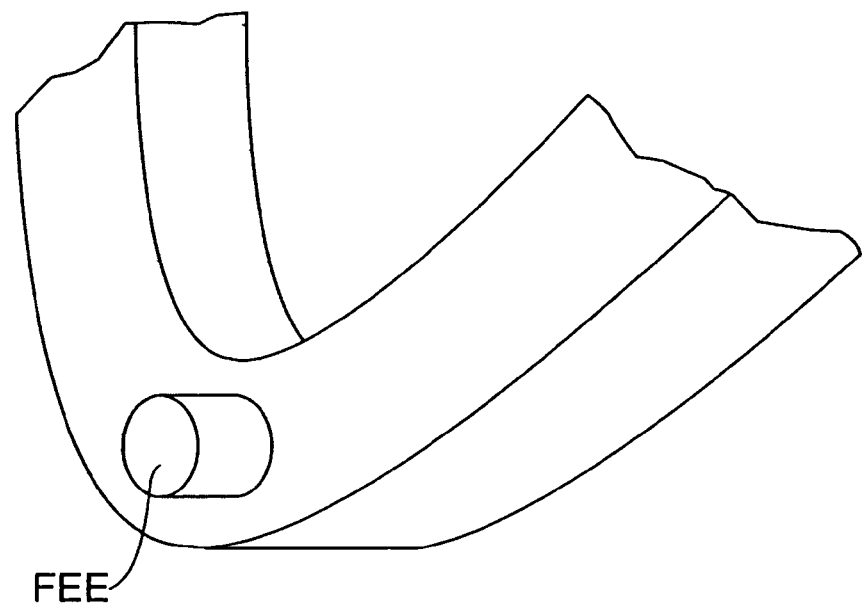
Figure 19:
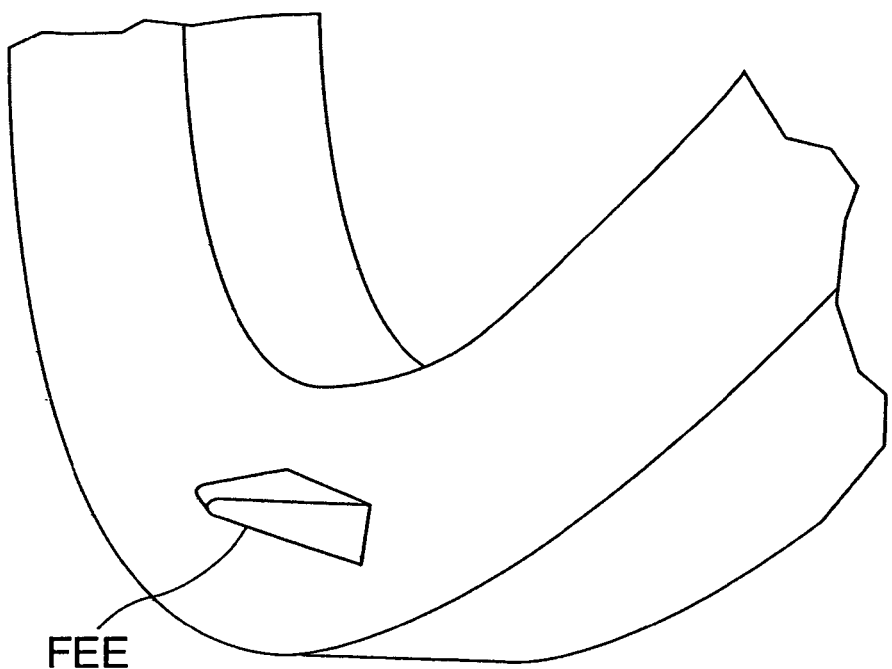
Figure 20:
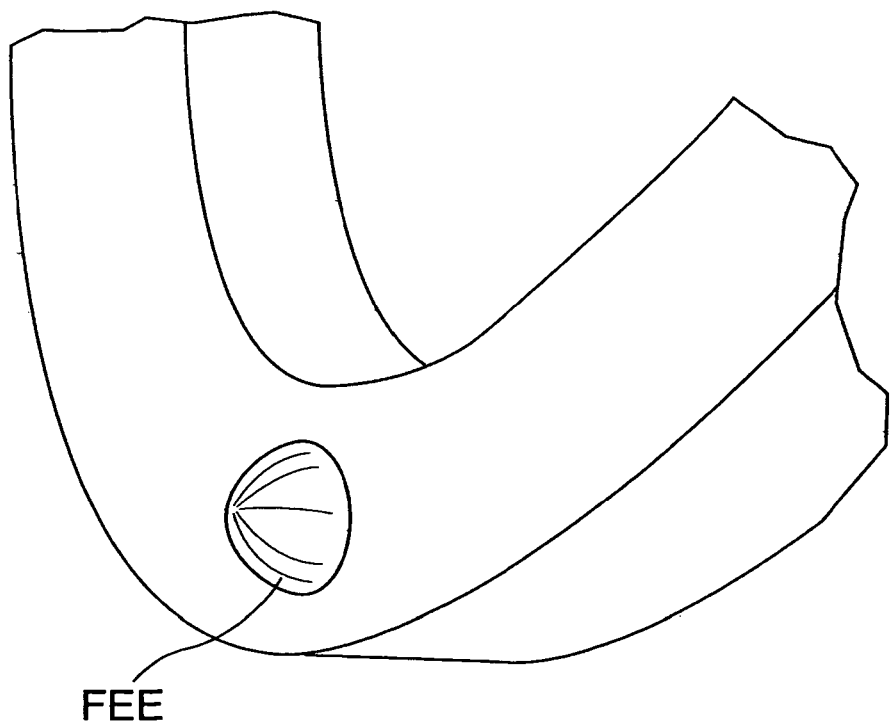
Figure 21:
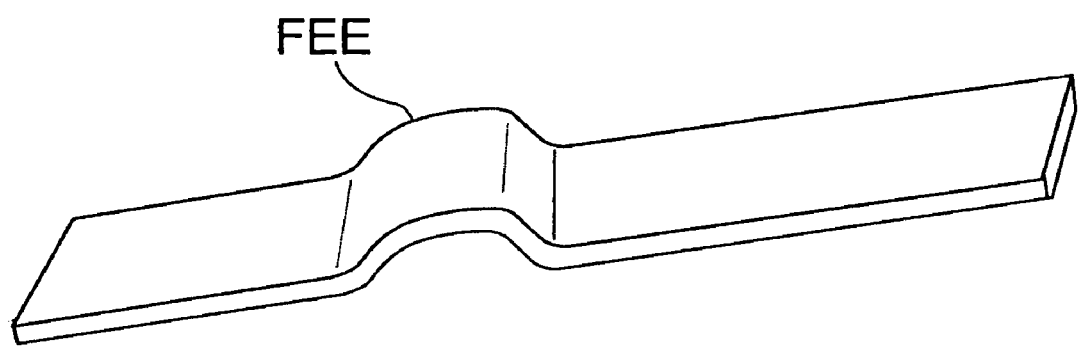
Figure 22:
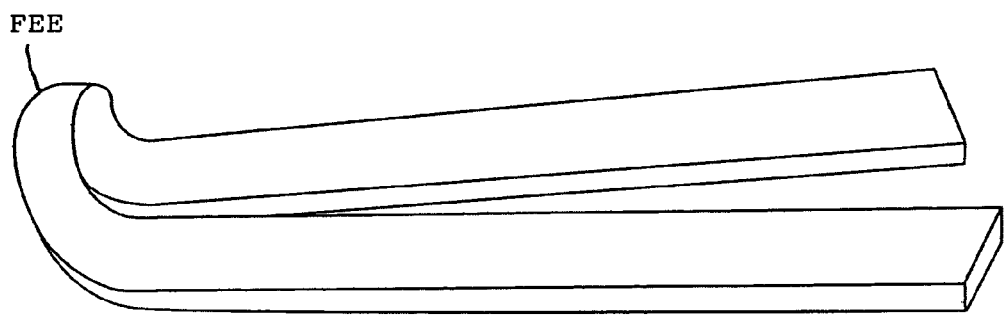

FIG. 17 illustrates a perspective view of a series of FEEs spaced along length of a strut section of a tack device. FIG. 18 illustrates a detailed view of a cylindrically shaped FEE placed at the apex of a strut section of the tack device. FIG. 19 illustrates a perspective view of a FEE formed as a pyramid shaped element at the apex of a strut section. FIG. 20 illustrates a perspective view of a FEE formed as a dome element at the apex of a strut section. FIG. 21 illustrates a perspective view of a FEE formed by bending the apex of a strut section upward. FIG. 22 illustrates a perspective view of a FEE formed by twisting a strut section (made from wire).

IV. Method and Devices for Delivering Plaque Tacks and Forming Intravascular Constructs In Situ A variety of delivery methodologies and devices that can be used to deploy plaque tacks, some of which are described below. For example, a plaque tack can be delivered into the blood vessel with an endovascular insertion. The delivery devices for the different embodiments of plaque tacks can be different or the same and can have features specifically designed to deliver the specific tack. The plaque tack and installation procedure may be designed in a number of ways that share a common methodology of utilizing an expansion force of the delivery mechanism (such as balloon expansion) and/or the expansion force of a compressible annular band to enable the tack to be moved into position in the blood vessel, then released, unfolded or unplied to an expanded state within the blood vessel.

Referring back to FIGS. 4-4D, a delivery device or catheter 11 with an outer sheath 13 is shown in a pre-delivery state. Multiple plaque tacks 10 can be compressed to be loaded onto the surface of the delivery device 11. The outer sheath 13 can then be advanced to cover the plaque tacks 10 in preparation for delivery. In some embodiments, the plaque tacks 10 are flash frozen in their compressed state to facilitate loading onto the delivery device. The tacks can extend in an array 10× over a given length of the delivery device.

It can be seen that the plaque tack 10 can be positioned in a patient's vasculature at a treatment site by the delivery device 11. The outer sheath 13 can be withdrawn or retracted to expose and release the plaque tack 10. The tack 10 can then be expanded in any suitable way, such as by being configured to self-expand or to be balloon expanded, as discussed herein.

Figure 23:
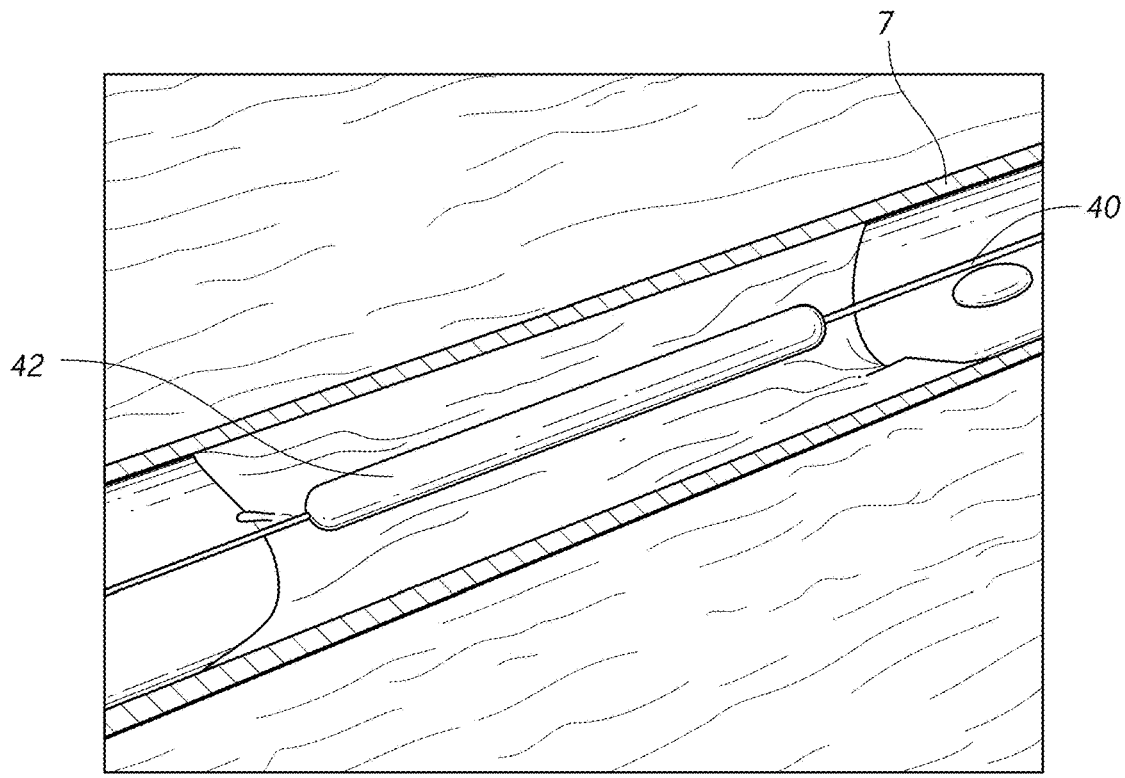
FIGS. 23-29 illustrate a method of delivery of a plaque tack into a blood vessel.
Figure 24:
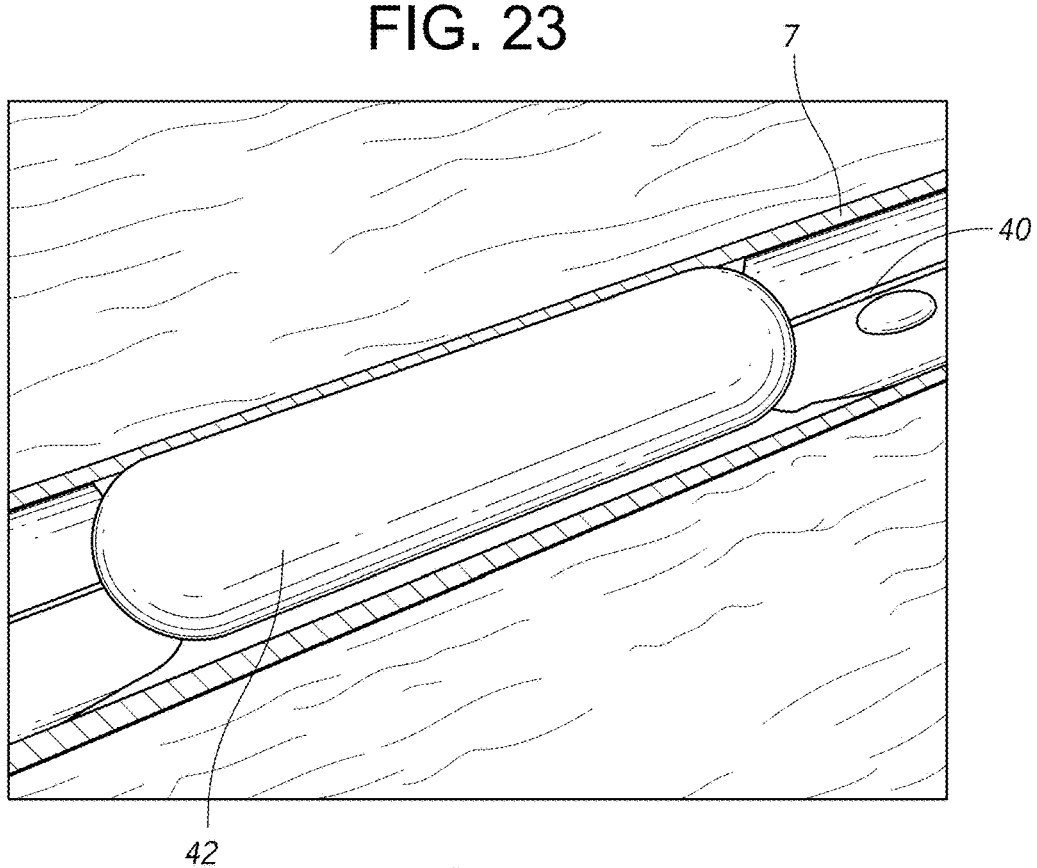

Turning now to FIGS. 23-31B, a method of delivery of one or more tack 10" will be described. As has been mentioned, an angioplasty procedure or other type of procedure can be performed in a blood vessel 7. The angioplasty may be performed on a diseased or obstructed portion of the blood vessel 7. As shown in FIG. 23, a guidewire 40 followed by an angioplasty balloon catheter carrying balloon 42 are advanced into a blood vessel 7 in a location containing an obstruction formed by plaque. The balloon 42 is inflated at the desired location to compress the plaque and widen the vessel 7 (FIG. 24). The balloon 42 can then be deflated and removed.

Figure 25:
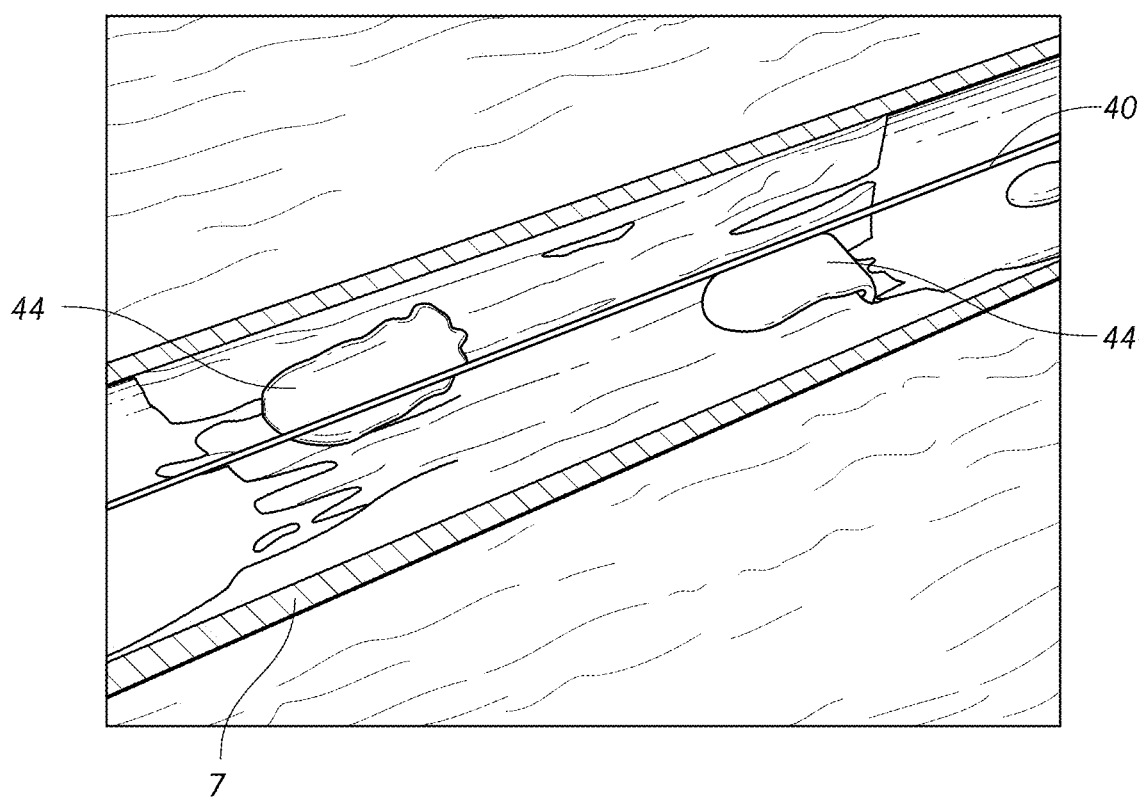

While widening the vessel 7, a dissection 44 of the plaque may be caused by the angioplasty (FIG. 25). A plaque tack or staple 10" can then be used to secure the plaque dissection 44 to the lumen wall 7.

Figure 26:
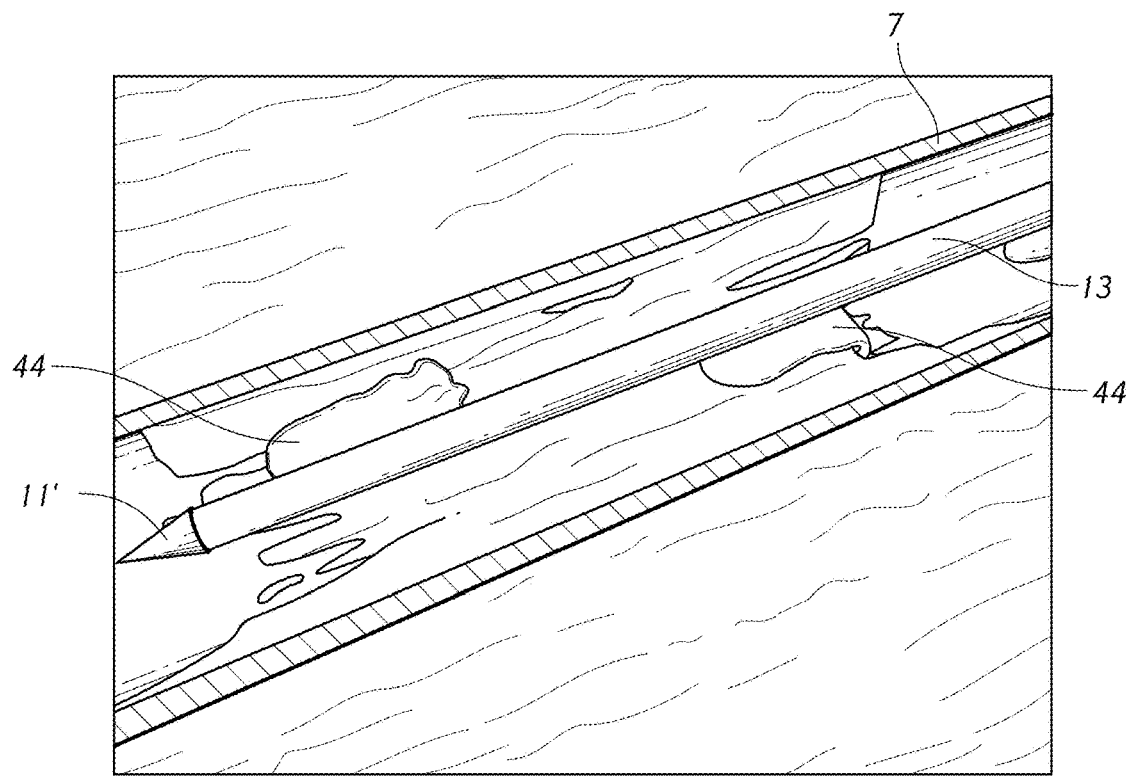
Figure 27:
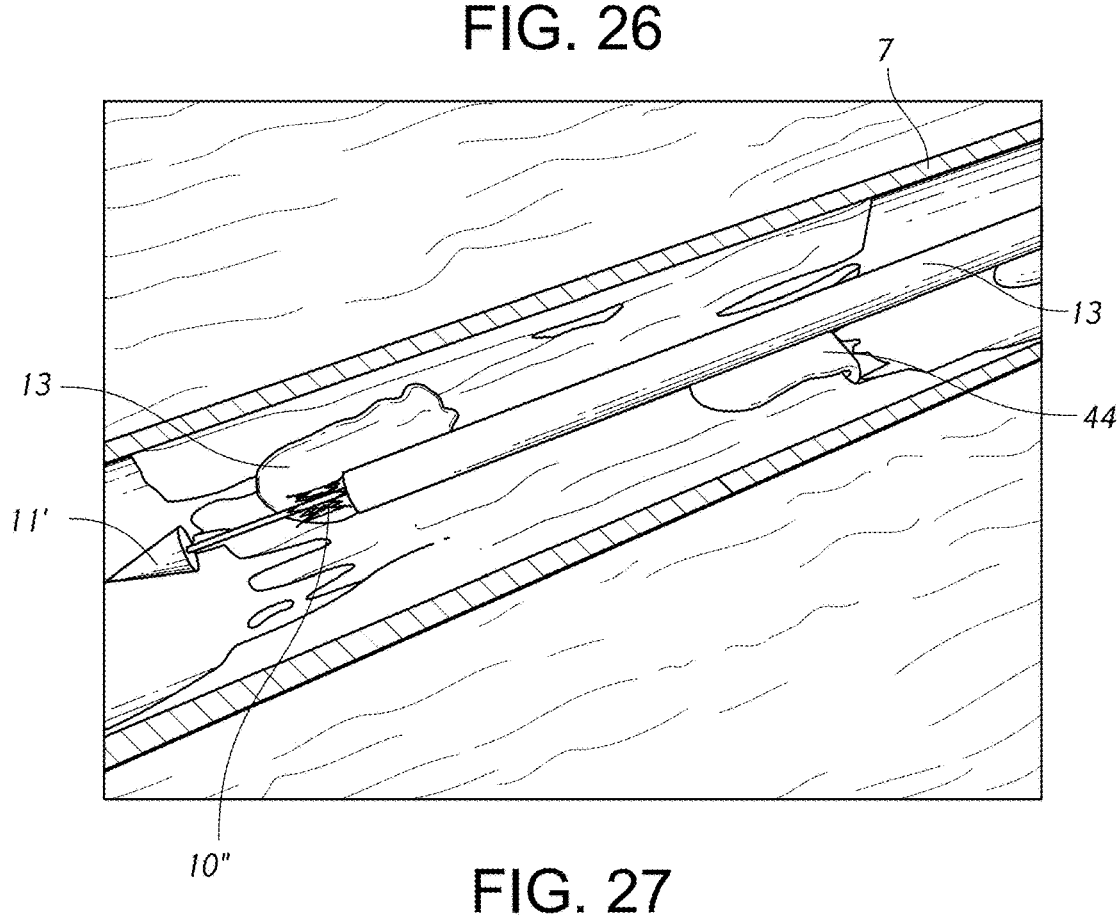

A delivery catheter 11' preloaded with one or more tacks 10" can be advanced along the guidewire 40 to the treatment site (FIG. 26). An outer sheath 13' can be withdrawn, exposing a portion of the plaque tack 10". As has been discussed, the outer sheath 13' can be withdrawn until a set point and then the position of the catheter within the vessel can be adjusted, if necessary, to ensure precise placement of the plaque tack 10" (FIG. 27). The set point can be for example, right before uncovering any of the tacks, uncovering a portion or all of a ring, uncovering a ring and an anchor, etc.

Figure 28:
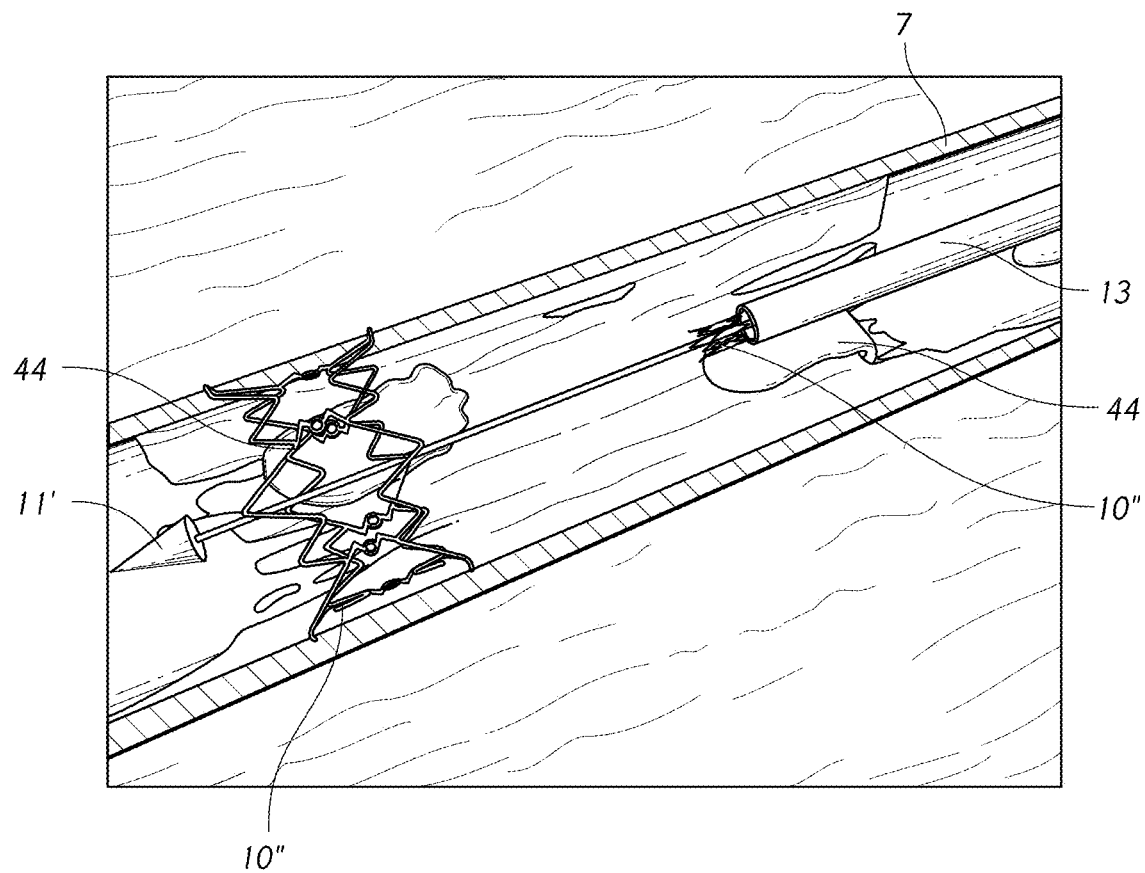

The tack 10" can then be released in the desired location in the lumen. As discussed previously, simultaneous placement can result upon release of some embodiments of the plaque tack 10". Additional plaque tacks 10" can then be placed as desired (FIG. 28). Upon placement of the second tack 10", an intravascular construct is formed in situ. 11. The in situ placement can be in any suitable vessel, such as in any peripheral artery. The construct need not be limited to just two tacks 10". In fact, a plurality of at least three intravascular tacks 10" (or any of the other tacks herein) can be provided in an intravascular construct formed in situ. In one embodiment each of the plurality of tacks has a length of no more than about 8 mm, e.g., about 6 mm in an uncompressed state. In one configuration, at least one of, e.g., each of, the tacks are spaced apart from an adjacent tack by at least about 4 mm. Although certain embodiments have a length of 8 mm or less, other embodiments can be longer, e.g., up to about 15 mm long. Also, neighboring tacks 10' be positioned as close as 2 mm apart, particularly in vessels that are less prone to bending or other movements. In one embodiment, each of the tacks has a relatively low radial force, e.g., having a radial expansion force of no more than about 4 N, and in some cases about 1 N or less. In some embodiments, tacks can be configured with as little as 0.25 N radial force.

While a three tack construct formed in situ may be suitable for certain indications, an intravascular construct having at least 5 intravascular tacks may be advantageous for treating loose plaque, vessel flaps, dissections or other maladies that are significantly more elongated (non focal). For example, while most dissections are focal (e.g., axially short), a series of dissections may be considered and treated as a more elongated malady.

In some cases, even shorter axial length tack can be used to treat even more spaced apart locations. For example, a plurality of tacks each having a length of no more than about 7 mm can be placed in a vessel to treat a tackable malady. At least some of, e.g., each of, the tacks can be spaced apart from an adjacent tack by at least about 5 mm. In some cases, it may be preferred to provide gaps between adjacent tacks that can range from about 6 mm to about 10 mm.

Figure 29:
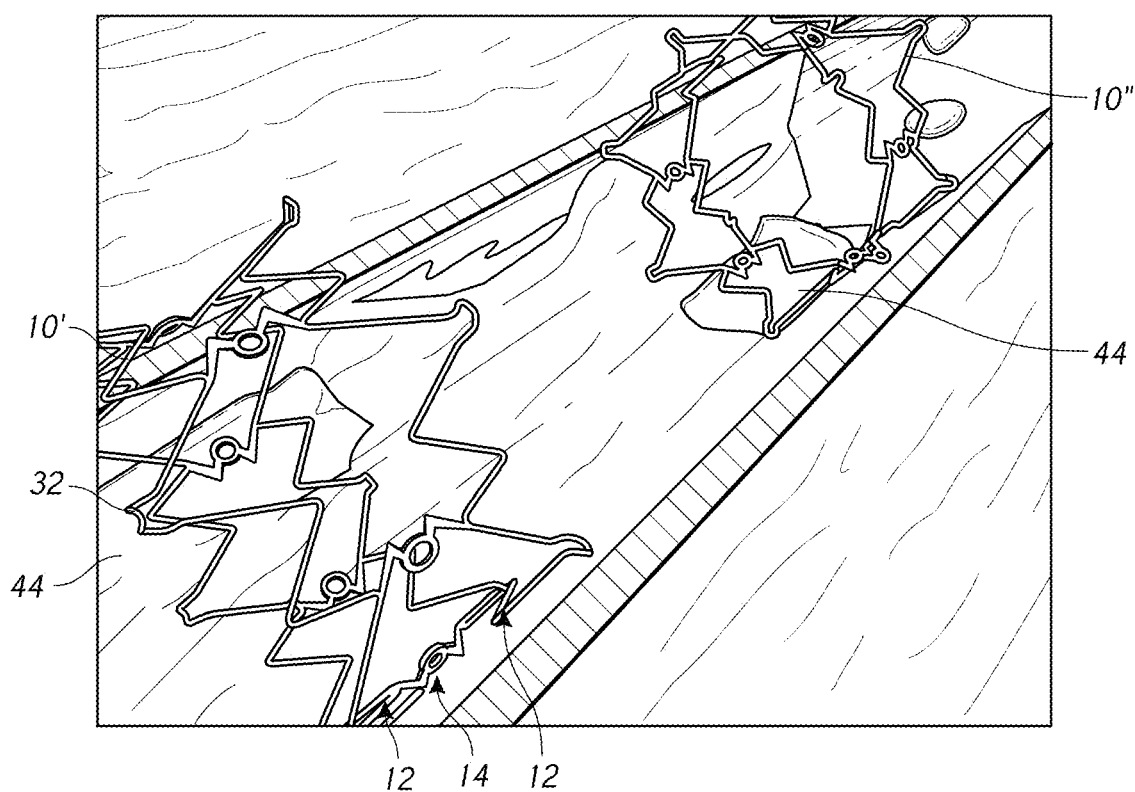

Optionally, once the plaque tacks 10" are in place, the angioplasty balloon can be returned to the treatment site and inflated to expand the plaque tacks 10" to the desired state of expansion. FIG. 29 shows the plaque tacks 10" in their final implanted state.

Figure 30A:
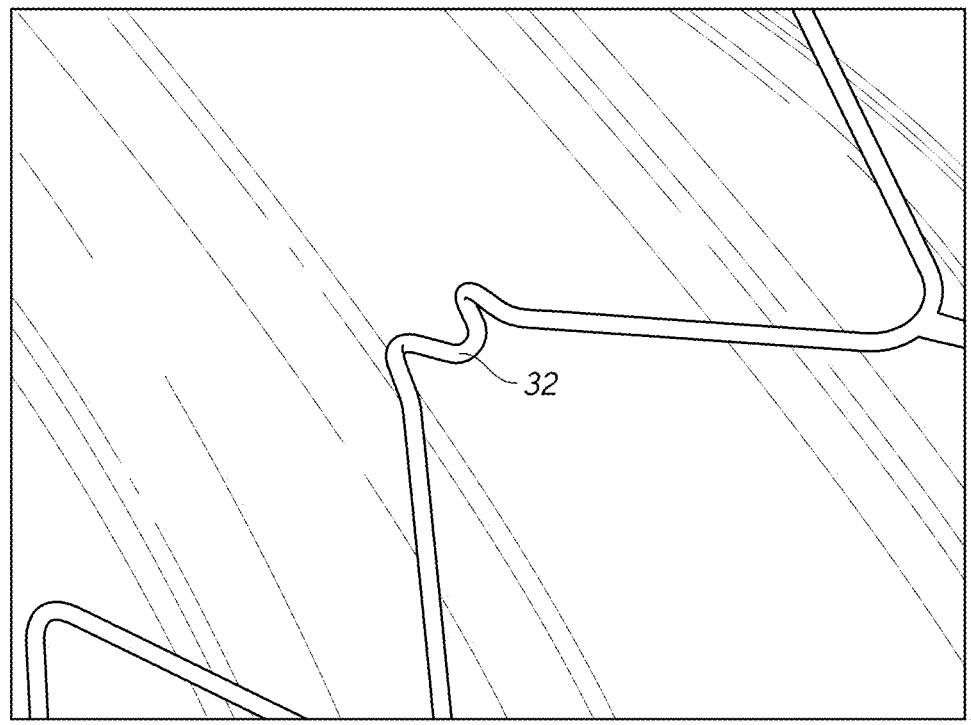
FIGS. 30A-B show a focal elevating element engaging plaque.
Figure 30B:
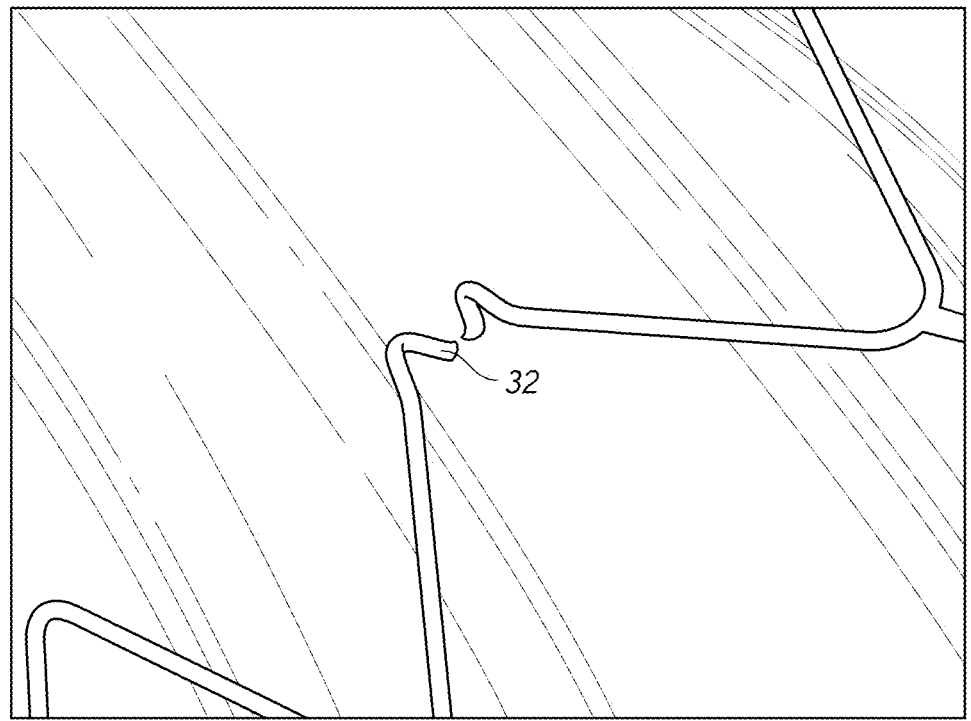
Figure 31A:
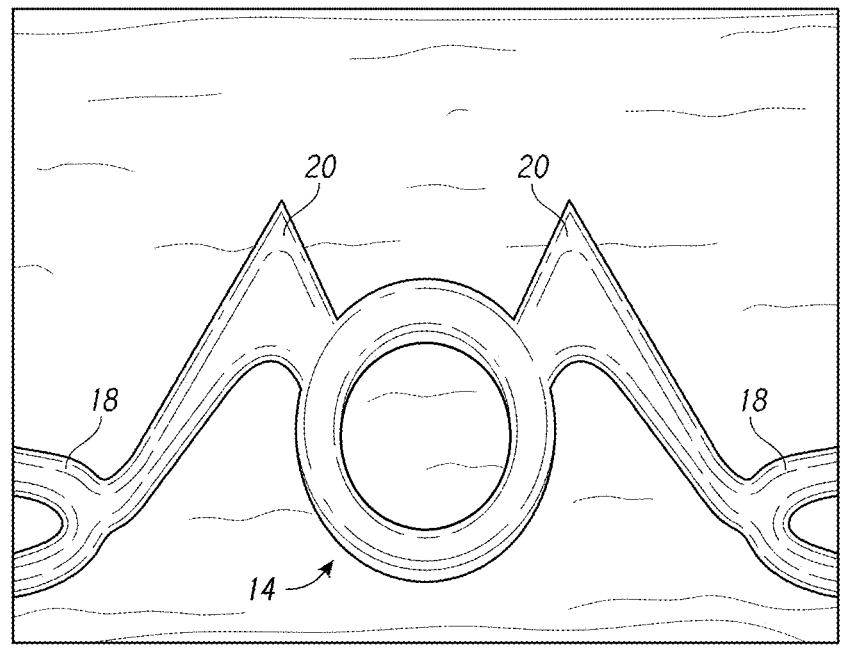
FIGS. 31A-B show anchors engaging plaque.
Figure 31B:
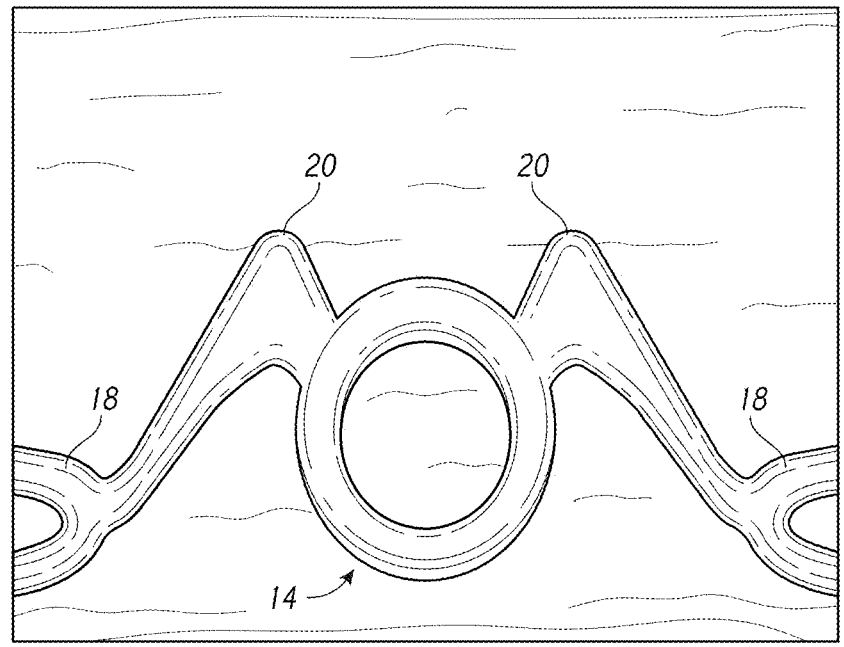

Referring to FIGS. 29, 30A, and 30B, it can be seen how the focal elevating elements 32 can both penetrate the plaque in the blood vessel wall and also minimize the contact area of the plaque tack 10" with the blood vessel wall. Similarly, FIGS. 29, 31A, and 31B illustrate the penetration of the anchors 20. It can also be seen that the position of the anchors 20 on the bridge 14 allow the anchors to protrude tangentially from the circular shape formed by the plaque tack 10". This beneficially allows the anchors 20 to engage the plaque or vessel wall while also minimizing the overall amount of contact by the plaque tack 10", similar to the focal elevating elements 32.

Use of Plaque Tack after Drug Eluting Balloon Angioplasty

The use of plaque tack devices can be combined with use of drug eluting balloon (DEB) angioplasty to manage post angioplasty dissection and avoid the need for stents. In DEB angioplasty, a drug-eluting balloon or a drug coated balloon is prepared in a conventional manner. The drug may be one, or a combination, of biologically active agents that are used for various functions, such as anti-thrombotic, anti-mitotic, anti-proliferative, anti-inflammatory, stimulative of healing, or other functions. The DEB is delivered on a guidewire across an area of blockage or narrowing in the blood vessel system. The DEB is inflated to a specific pressure and for a period of time consistent with the manufactures guidelines of use for treatment purposes, as it pertains the drug coating and the intended outcomes, then the DEB is deflated and removed. At this stage the medication from the DEB has been transferred to the wall of the blood vessel. Intravascular imaging by ultrasound is then used to assess the integrity of the artery and the smoothness of the blood vessel surface at the site where the balloon was inflated. The presence of damage along the surface may be indicated as dissection, elevation of plaque, disruption of tissue, irregularity of surface. The plaque tack is used to tack down the damaged, disrupted, dissected, or irregular blood vessel surface. This permits continuation of a "stent-free" environment even if damage to the blood vessel has occurred as a result of balloon angioplasty.

At this stage the medication from the DEB has been transferred to the wall of the blood vessel. Contrast is administered into the blood vessel under fluoroscopic guidance or another method such as intravascular ultrasound is used to assess the integrity of the artery and the smoothness of the blood vessel surface at the site where the balloon was inflated. In some cases, one or more of these completion studies will demonstrate the presence of damage along the surface at the site of the balloon inflation. This damage may include dissection, elevation of plaque, disruption of tissue, irregularity of surface.

The plaque tack delivery catheter is loaded with multiple tacks that may be placed at the discretion of the operator, and advanced over a guidewire in the blood vessel to the location where the dissection or disruption or irregularity has occurred. The location is specifically and carefully identified using angiography. The plaque tack(s) is or are deployed at the location(s) of the lesion. More than one tack may be placed to tack down a major dissection. If more than one tack is placed, it may be placed only according to the rules of proper spacing of tacks. That is, the tack should be at least one tack axial length apart. After placement of the tack, it may be further expanded into the wall of the blood vessel using a standard angioplasty balloon or a drug-eluting or drug coated balloon (either as a stand alone (separate) device or integral to the delivery system). The purpose of the tack is generally not to hold the blood vessel lumen open but to tack down the non-smooth or dissected surface of the blood vessel. This "touch-up strategy" permits the resolution of the damage created by the drug-eluting or drug coated balloon without resorting to stent placement and thereby maintaining a "stent-free" environment.

As a further measure, described above, the plaque tack device itself can be used to deliver medication to the blood vessel. In addition to the delivery of medication from the anchors, the tack can be coated with medication prior to tack placement. The purpose of this activity is to permit the tack to elute biologically active agent or agents that have positive effects on the blood vessel.

One or more of the tacks deployed in accordance with the present invention may be coated with or otherwise carry a drug to be eluted over time at the deployment site. Any of a variety of therapeutically useful agents may be used, including but not limited to, for example, agents for inhibiting restenosis, inhibiting platelet aggregation, or encouraging endothelialization. Some of the suitable agents may include smooth muscle cell proliferation inhibitors such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine, lipoxygenase inhibitors; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, colchicine, epothilones, endostatin, angiostatin, Squalamine, and thymidine kinase inhibitors; L-arginine; antimicrobials such astriclosan, cephalosporins, aminoglycosides, and nitorfuirantoin; anesthetic agents such as lidocaine, bupivacaine, and ropivacaine; nitric oxide (NO) donors such as lisidomine, molsidomine, NO-protein adducts, NO-polysaccharide adducts, polymeric or oligomeric NO adducts or chemical complexes; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; interleukins, interferons, and free radical scavengers; vascular cell growth promoters such as growth factors, growth factor receptor antagonists, transcriptional activators, and translational promoters; vascular cell growth inhibitors such as growth factor inhibitors (e.g., PDGF inhibitor—Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; Tyrosine kinase inhibitors, chymase inhibitors, e.g., Tranilast, ACE inhibitors, e.g., Enalapril, MMP inhibitors, (e.g., Ilomastat, Metastat), GP IIb/IIIa inhibitors (e.g., Intergrilin, abciximab), seratonin antagnonist, and 5-HT uptake inhibitors; cholesterol-lowering agents; vasodilating agents; and agents which interfere with endogeneus vascoactive mechanisms. Polynucleotide sequences may also function as anti-restenosis agents, such as p15, p16, p18, p19, p21, p27, p53, p57, Rb, nFkB and E2F decoys, thymidine kinase ("TK") and combinations thereof and other agents useful for interfering with cell proliferation. The selection of an active agent can be made taking into account the desired clinical result and the nature of a particular patient's condition and contraindications. With or without the inclusion of a drug, any of the tacks disclosed herein can be made from a bioabsorbable material. Various polymeric carriers, binding systems or other coatings to permit controlled release of active agent from the tack or its coating are well known in the coronary stent arts and not reproduced herein.

In summary, the plaque tack can be used for plaque retention following balloon angioplasty treatment of atherosclerotic occlusive disease while avoiding problems with the use of stents due to installing a large mass of foreign material in the body which may cause injury, inflammation, and/or provide sites for restenosis. In contrast with stents, the plaque tack device minimizes the material structure while only being installed at one or more plaque dissection sites that require retention. The focal elevating elements on the tack periphery minimizes the contact surface area of the plaque tack with the blood vessel walls and reduces the risk of causing plaque dissection or injury to the blood vessel walls. This approach offers clinicians the ability to perform a minimally invasive post-angioplasty treatment and produce a stent-like result without using a stent.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Additionally, it is contemplated that various aspects and features of the invention described can be practiced separately, combined together, or substituted for one another, and that a variety of combination and sub-combinations of the features and aspects can be made and still fall within the scope of the invention. Thus, it is intended that the scope of the present invention herein disclosed should not be limited by the particular disclosed embodiments described above, but should be determined only by a fair reading of the claims.

What is claimed is:

1. An endovascular implant comprising:
  a self-expanding frame comprising:
    a first circumferentially oriented ring comprising proximally facing apices and distally facing apices, the first circumferentially oriented ring defining a first end of the endovascular implant,
    a second circumferentially oriented ring comprising proximally facing apices and distally facing apices, the second circumferentially oriented ring defining a second end of the endovascular implant,
    a plurality of bridges connecting non-consecutive said proximally facing apices of the first circumferentially oriented ring to one circumferentially-adjacent said distally facing apex of the second circumferentially oriented ring,
    a length of the implant being no more than 15 mm, and
    an expanded diameter of the implant being between 1 mm and 10 mm;
  a plurality of cells between the first circumferentially oriented ring and the second circumferentially oriented ring and circumferentially between pairs of bridges of the plurality of bridges; and
  a radiopaque marker coupled to an eyelet on each bridge of the plurality of bridges, the eyelet at a midline of the implant, the radiopaque marker comprising at least one of tantalum or gold, the radiopaque marker configured to offer clear visibility of the endovascular implant in a catheter delivery system and to provide guidance to a clinician for accurate placement in a superficial femoral artery, an iliac artery, a popliteal artery, or a tibial artery during a medical procedure.

2. The implant of claim 1, wherein an outer surface of the radiopaque marker is disposed radially inside an outer surface of the implant.

3. An endovascular implant delivery system comprising:
  a catheter shaft;
  a plurality of self-expanding endovascular implants around the catheter shaft and spaced apart by a plurality of catheter shaft protrusions, each self-expanding endovascular implant of the plurality of self-expanding endovascular implants comprising the implant of claim 1; and
  a sheath around the catheter shaft.

4. The system of claim 3, wherein each self-expanding endovascular implant of the plurality of self-expanding endovascular implants is spaced apart from an adjacent each self-expanding endovascular implant of the plurality of self-expanding endovascular implants by at least about 4 mm in the endovascular implant delivery system.

5. The system of claim 3, wherein the plurality of self-expanding endovascular implants is at least five self-expanding endovascular implants.

6. An endovascular implant comprising:
  a first undulating ring comprising proximally facing apices;
  a second undulating ring comprising distally facing apices;
  a plurality of bridges connecting every-other said proximally facing apex of the first undulating ring to a circumferentially-adjacent said distally facing apex of the second undulating ring,
  a plurality of cells between the first undulating ring and the second undulating ring and between pairs of bridges of the plurality of bridges; and
  a radiopaque marker coupled to an eyelet;
  wherein a length of the implant is no more than 15 mm, and
  wherein the implant has an expanded diameter between 1 mm and 10 mm.

7. The implant of claim 6, wherein the radiopaque marker is configured to provide guidance for accurate placement during a medical procedure in a superficial femoral artery, an iliac artery, a popliteal artery, or a tibial artery.

8. The implant of claim 6, wherein the implant is self-expanding.

9. The implant of claim 6, wherein the first undulating ring at least partially defines a first end of the implant and wherein the second undulating ring at least partially defines a second end of the implant.

10. An endovascular implant delivery system comprising:
  a catheter shaft;
  a plurality of endovascular implants around the catheter shaft and spaced apart by a plurality of catheter shaft protrusions, each endovascular implant of the plurality of endovascular implants comprising the implant of claim 6; and
  a sheath around the catheter shaft.

11. The system of claim 10, wherein each endovascular implant of the plurality of endovascular implants is spaced apart from an adjacent each endovascular implant of the plurality of endovascular implants by at least about 4 mm in the endovascular implant delivery system.

12. The system of claim 10, wherein the plurality of endovascular implants is at least five endovascular implants.

13. An endovascular implant comprising:
  a first ring comprising a first set of inward apices;
  a second ring comprising a second set of inward apices; and
  a plurality of bridges connecting alternating circumferentially-adjacent inward apices of the first set of inward apices and the second set of inward apices, a plurality of cells between the first ring and the second ring;

wherein a length of the implant is no more than 15 mm, and wherein the implant has an expanded diameter between 1 mm and 10 mm, and wherein the length is about equal to or less than the expanded diameter.

14. The implant of claim 13, further comprising an eyelet.

15. The implant of claim 14, further comprising a radiopaque marker coupled to the eyelet.

16. The implant of claim 13, wherein the implant is self-expanding.

17. The implant of claim 15, wherein the radiopaque marker is configured to provide guidance to a clinician for accurate placement in a superficial femoral artery, an iliac artery, a popliteal artery, or a tibial artery during a medical procedure.

18. The implant of claim 13, wherein the first ring at least partially defines a first end of the implant and wherein the second ring at least partially defines a second end of the implant.

19. An endovascular implant delivery system comprising:
a catheter shaft;
a plurality of endovascular implants around the catheter shaft and spaced apart by a plurality of catheter shaft protrusions, each endovascular implant of the plurality of endovascular implants comprising the implant of claim 13; and
a sheath around the catheter shaft.

20. The system of claim 19, wherein each endovascular implant of the plurality of endovascular implants is spaced apart from an adjacent each s endovascular implant of the plurality of endovascular implants by at least about 4 mm in the endovascular implant delivery system.

21. The system of claim 19, wherein the plurality of endovascular implants is at least five endovascular implants.

* * * * *